US012565659B2

(12) United States Patent
Dixon et al.

(10) Patent No.: US 12,565,659 B2
(45) Date of Patent: *Mar. 3, 2026

(54) RECOMBINANT LAC POLYNUCLEOTIDES AND USES THEREOF TO INCREASE PRODUCTION OF C-LIGNIN IN PLANTS

(71) Applicant: UNIVERSITY OF NORTH TEXAS, Denton, TX (US)

(72) Inventors: Richard A. Dixon, Sulphur, OK (US); Fang Chen, Denton, TX (US); Chunliu Zhuo, Denton, TX (US)

(73) Assignee: UNIVERSITY OF NORTH TEXAS, Denton, TX (US)

( * ) Notice: Subject to any disclaimer, the term of this patent is extended or adjusted under 35 U.S.C. 154(b) by 21 days.

This patent is subject to a terminal disclaimer.

(21) Appl. No.: 18/594,315

(22) Filed: Mar. 4, 2024

(65) Prior Publication Data

US 2024/0263187 A1 Aug. 8, 2024

Related U.S. Application Data

(63) Continuation of application No. 17/528,375, filed on Nov. 17, 2021, now Pat. No. 11,959,089.

(60) Provisional application No. 63/114,834, filed on Nov. 17, 2020.

(51) Int. Cl.
*C12N 15/82* (2006.01)

(52) U.S. Cl.
CPC ..... *C12N 15/8255* (2013.01); *C12N 15/8218* (2013.01)

(58) Field of Classification Search
None
See application file for complete search history.

(56) References Cited

U.S. PATENT DOCUMENTS

2009/0183270 A1* 7/2009 Adams ............... C12N 15/8247
800/312

OTHER PUBLICATIONS

Wang, X. et al. Substrate Specificity of LACCASE8 Facilitates Polymerization of Caffeyl Alcohol for C-Lignin Biosynthesis in the Seed Coat of Cleome hassleriana, 2020, The Plant Cell, vol. 32: 3825-3845 with Supplemental Data. (Year: 2020).*

Chen F. et al. A polymer of caffeyl alcohol in plant seeds. 2012 Proceeding of the National Academies of Science. 109: 1772-1777. (Year: 2012).*

Tobimatsu, Y. et al. Coexistance but independent biosynthesis of catechyl and quaiacy/syringyl lignin polymers in seed coats. 2012, Plant Cell 25: 2587-2600. (Year: 2012).*

Chen F et al, Novel seed coat lignins in the Cactaceae: structure, distribution and implications for the evolution of lignin diversity, 2013, The Plant Journal, 73: 201-211. (Year: 2013).*

Guo H et al, Protein tolerance to random amino acid change, 2004, Proceedings of the National Academies of Science, 101:9205-9210. (Year: 2004).*

Chen F., et al., "A polymer of caffeyl alcohol in plant seeds", Proc. Natl. Acad. Sci. USA (2012), 109:1772-1777.

Li, Y., et al., "An 'ideal lignin' facilitates full biomass utilization", Sci. Adv. (2018), 4:eaau2968.

Nar, M., et al., "Superior plant based carbon fibers from electrospun poly-(caffeyl alcohol) lignin", Carbon (2016) 103:372-383.

Stone, M.L., et al. "Reductive catalytic fractionation of C-Lignin", ACS Sust. Chem. Eng. (2018) 6:11211-11218.

Tobimatsu, Y., et al., "Coexistence but independent biosynthesis of catechyl and quaiacyl/syringyl lignin polymers in seed coats", Plant Cell (2013) 25:2587-2600.

Zhuo, C., et al., "Enzymatic basis for C-lignin monomer biosynthesis in the seed coat of Cleome hassleriana", Plant J. (2019), 99:506-520.

Wang, X., et al., "Substrate specificity of LACCASE8 facilitates polymerization of caffeyl alcohol for C-Lignin biosynthesis in the seed coat of Cleome hassleriana", The Plant Cell (2020) 32: 3825-3845.

Chen, F., et al., "Novel seed coat lignins in the Cactaceae: structure, distribution and implications for the evolution of lignin diversity," The Plant Journal (2013), pp. 201-211.

Guo, H., et al. "Protein tolerance to random amino acid change," Proc Nat Acad Sci 2004 101:9205-9210.

Li et al. "Genome-wide identification and characterization of salvia miltiorrhiza laccases reveal potential targets for salvianolic acid B biosynthesis," Frontiers in Plant Science 2019 10:435.

* cited by examiner

*Primary Examiner* — Shubo Zhou
*Assistant Examiner* — Aleksandar Radosavljevic
(74) *Attorney, Agent, or Firm* — Thomas|Horstemeyer, LLP

(57) ABSTRACT

The disclosure provides recombinant LAC polynucleotides encoding a laccase (LAC) polypeptide capable of polymerizing caffeyl alcohol, vectors and cells including the recombinant LAC polynucleotide. The disclosure also provides transgenic plants including cells having the recombinant LAC polynucleotide of the present disclosure and methods of increasing production of C-lignin in a plant.

15 Claims, 23 Drawing Sheets

Specification includes a Sequence Listing.

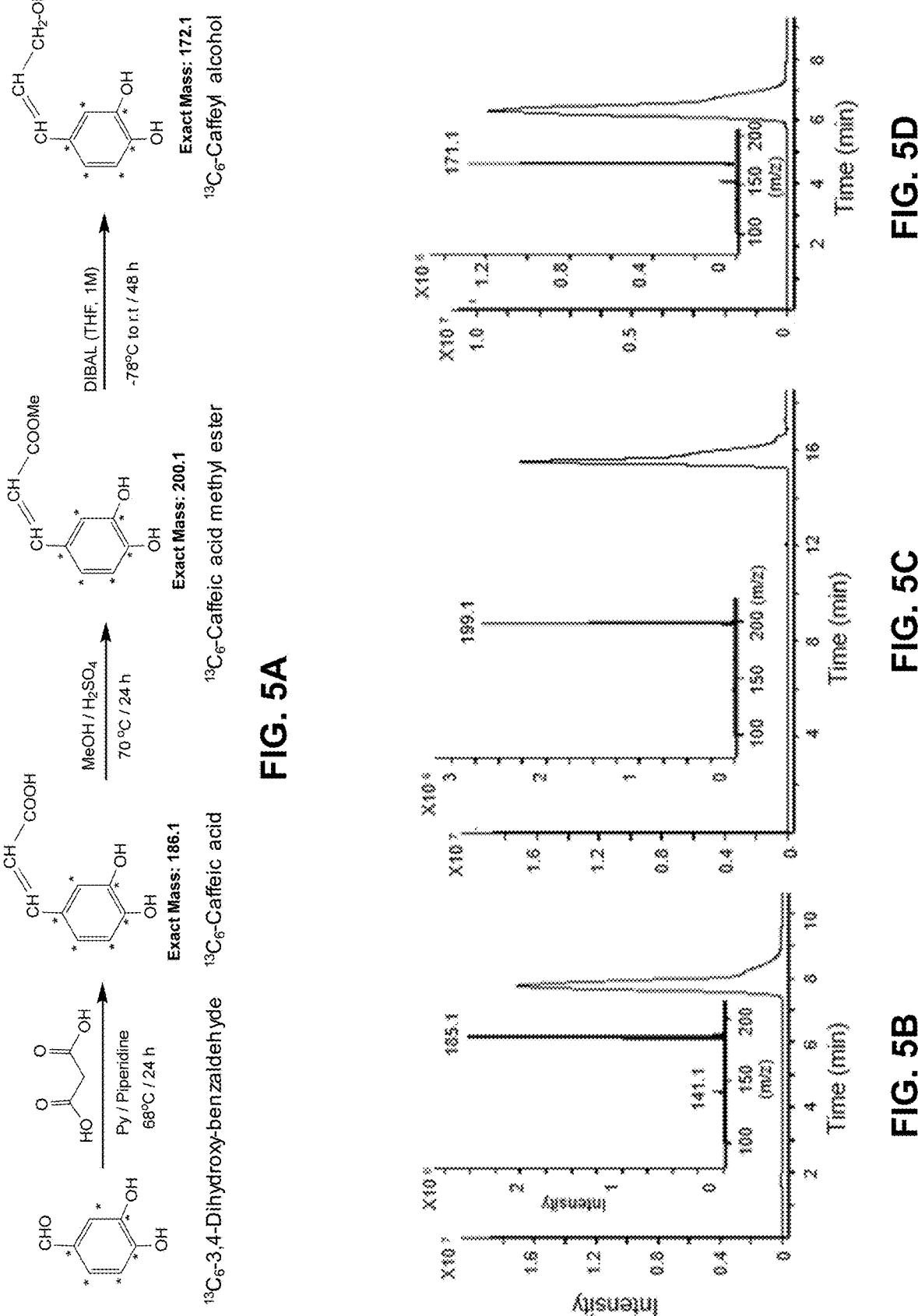

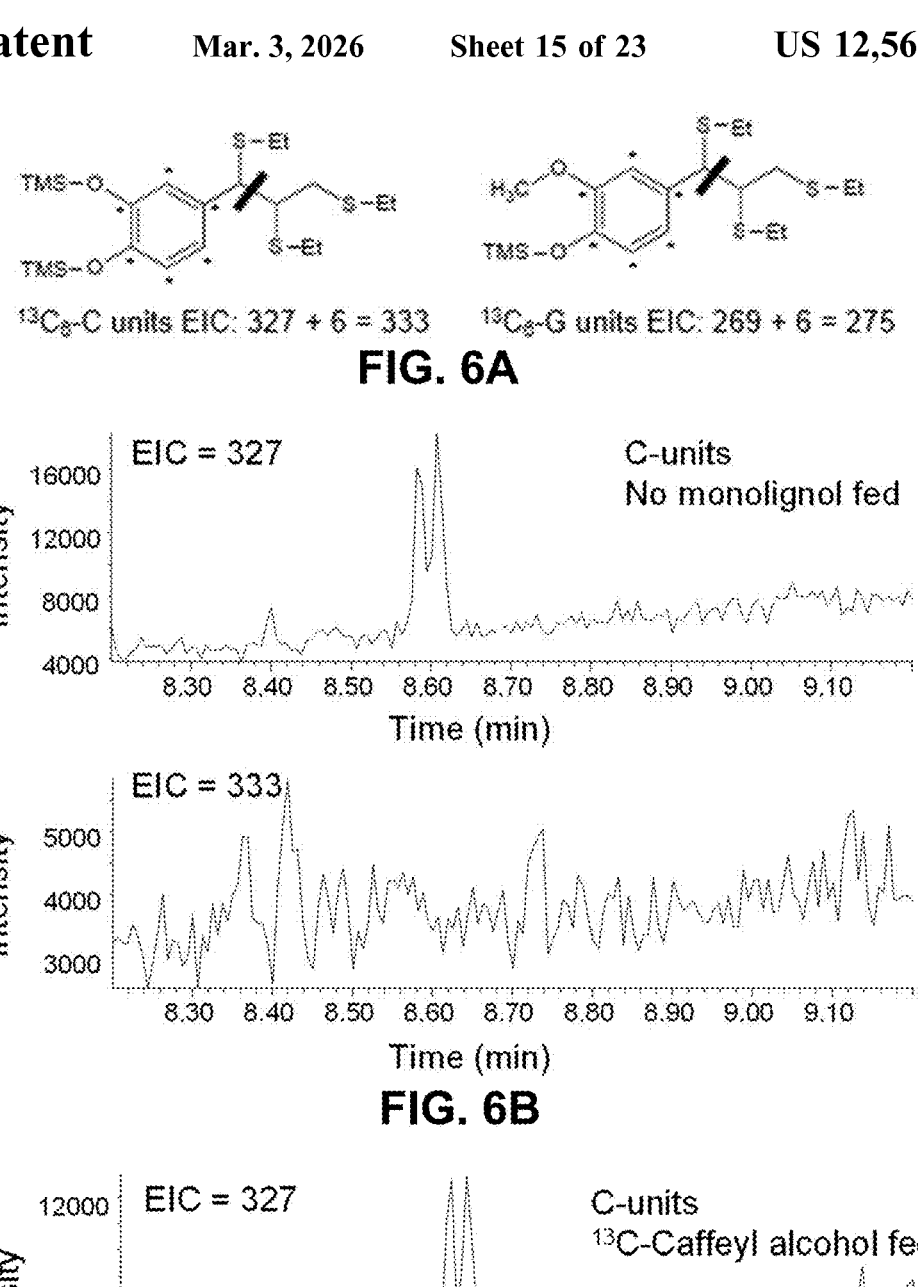
FIG. 6A
FIG. 6B
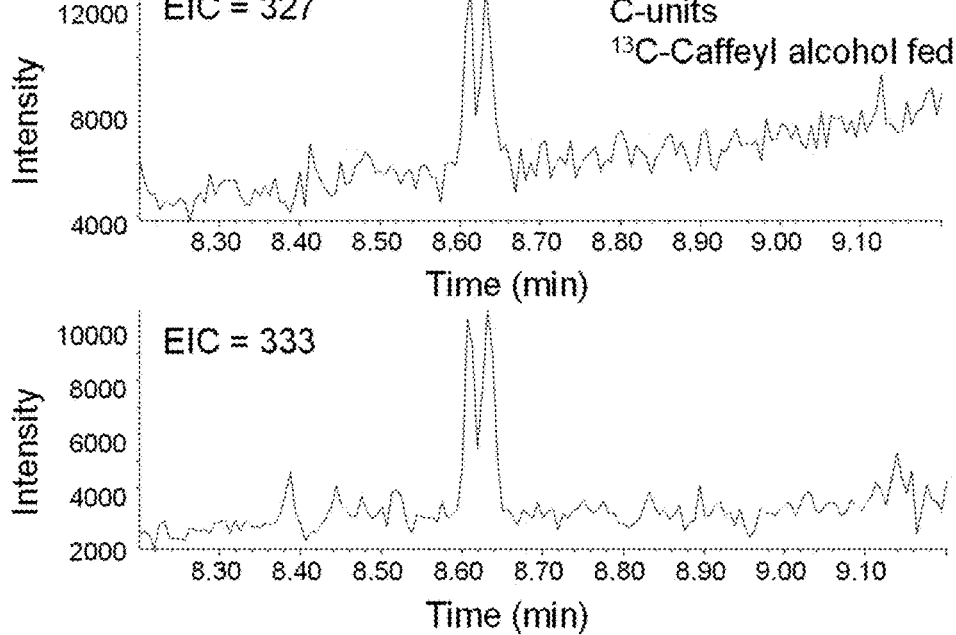
FIG. 6C

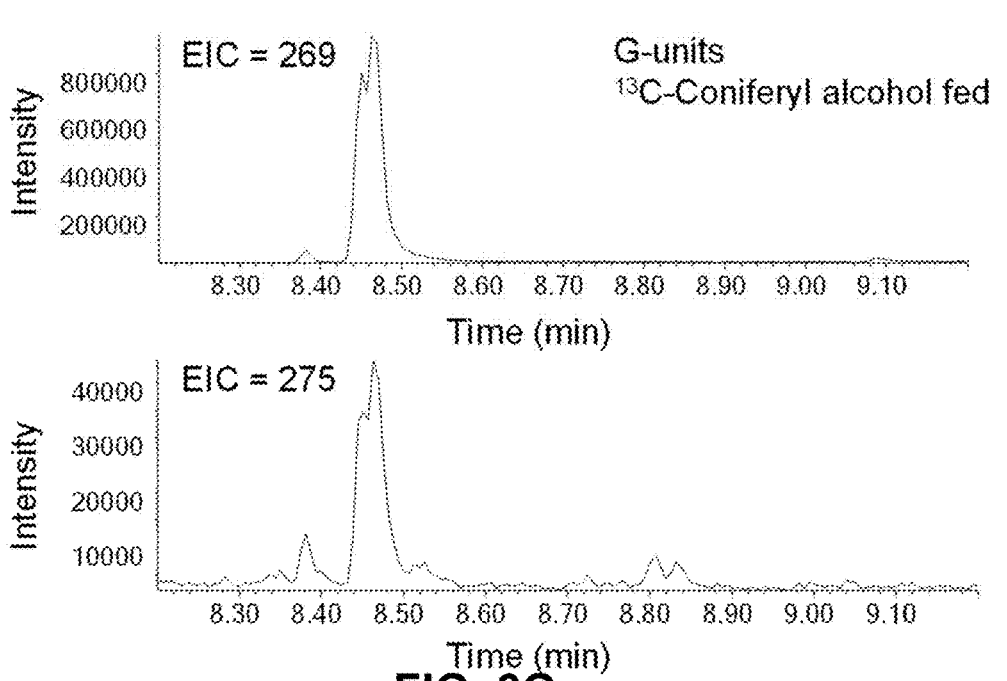
FIG. 6G
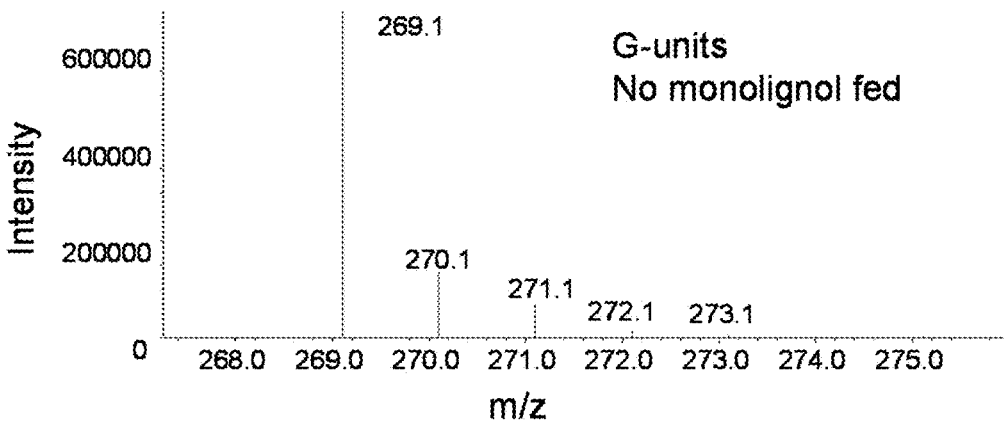
FIG. 6H
FIG. 6I

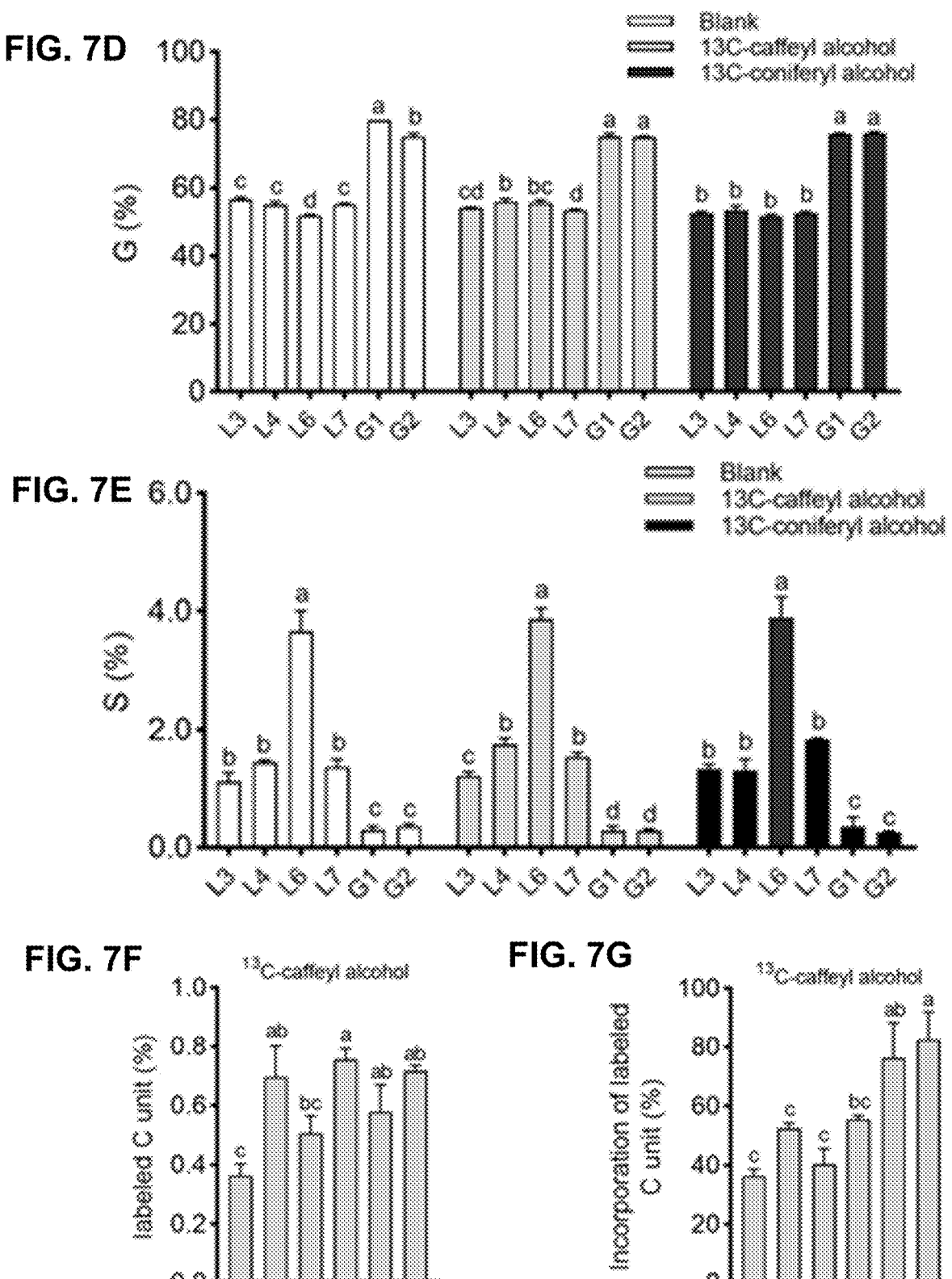

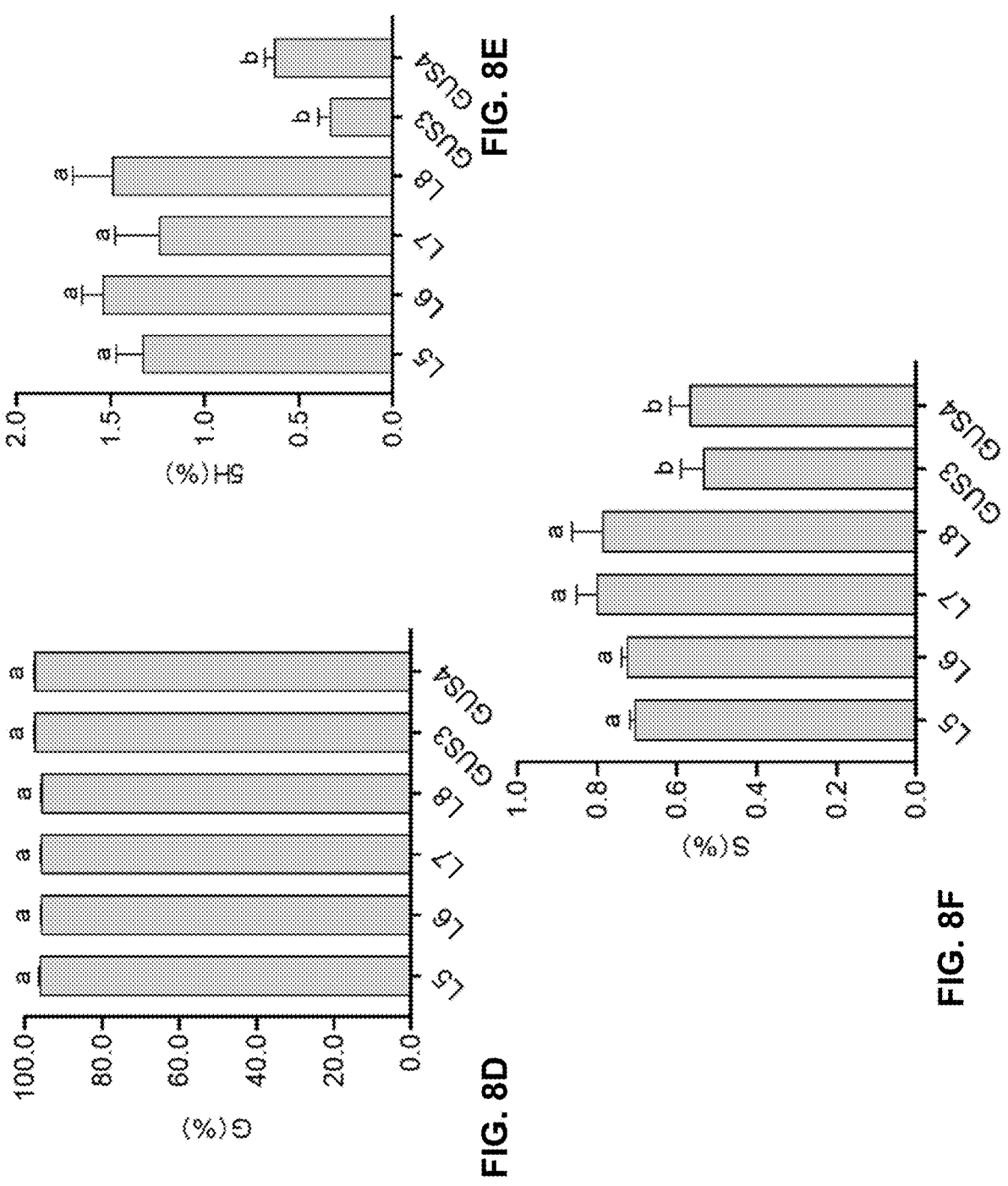

SEQUENCE LISTING

Sequence total quantity: 3
SEQ ID NO: 1        moltype = DNA  length = 3165
FEATURE             Location/Qualifiers
source              1..3165
                    mol_type = genomic DNA

```
                        organism = Cleome hassleriana
SEQUENCE: 1
aaaattgatt tattttatgc gatcggtata atattttttt ttaaaaaaaa acaaattata   60
aaagaagatt caccataaca tttcattacc ttcctccaag gcatcgtctc caagcccgaa  120
tatggccagt tttgagtgct ttctcatctg ctttgttctt atcctcctcc cttcttcttc  180
gtcgaaggct tatgcatctg tcgtcgaaca cactttcctt gtattactct cccacaatat  240
tttaatttta atttccagtc ttttttaacgt atggaaaaac tgtaaactga cggcgttagt  300
cgctcctgca ggtccaaaac ttcacggcga aaccgttgtg caaagagcag gtgataccga  360
cagttaacgg aagtcttccg ggtccgacgg taaacgtcag agagggagac acacttattg  420
ttcatgtcgt taacaactcc ccttttaacg tcaccattca ctggtaaatc cattcatcac  480
atacgattat agggtcgttt atagttatta gcatgaataa ggagttacta agaatctgtg  540
attatgctat taattagtct tgttttttcca cgtttcttga ttctatatag gcatggagtg  600
tttcagttga tgagtgcgtg gatggatgga acagatatga taacacaata tccgatccga  660
ccggaagata ggttcactta taagtttaac gtcacaggac aagaaggtac gctgcactgg  720
cacgcacatg tcgttaacct acgcgccacc ctgcacggtg ctcttgtcat ccgtcctcga  780
gctggtcggc cttatccttt tcccgaaccc tatgaagaag ctctcatcat tctcggtcgg  840
catatataca tacatataca tatgtatata tacatataat attttcatac ccaatgaatc  900
gtatatgaaa atccatatat tgattcggga aaacttttcg aatcgatgca gaacaatggt  960
ggaacaccga tatcgaaaat ctccaactaa ggcccgctcc tctttcagat gcctacctca 1020
tcaacggatt agcaggagat tcattcgatt gctcgcggaa tagtgagtga aaataaaaac 1080
atatataagt ctcatccgat tcacaaattc atatattcaa agcttctttt tttttttttg 1140
catctagaaa tgtttaaact agaggtggta caaggaaaaca ggtacttgct aaggatcata 1200
aacgcagcac ttaactcaca tctattcttc aagatagcga accattcctt gcgagtcgtg 1260
gccttagacg ccgtctacac gaatccttac gttaccgaca tcgttgtcct aacgccagga 1320
cagaccgtag acgcacttct ccatgcagac caaaccctag gctcatacta catgaccact 1380
cagctttacg tcagcgccac aggccagcca ttccccgaca aaacccctag caatgctctc 1440
gttgtctacc aaggtgccac gtcatcgtcc cgcgccatgc catcgttgcc cgacgtgacg 1500
gatacgcaga cagcgtatag attctcctcg agtatcaccg gccttgtcag tgggccccat 1560
tggaggccgg tgcctcgcaa cgtggacgag aggatgttta tgaccatggg gttaggtctt 1620
gagcaatgtc caccgagcat gcagtgtccc ggactgtacg gacaacaatt cgcaggctcg 1680
ctgaacaacc gctcgttcga aaatcccaag acatttccca tgcaagaggc ttatttctac 1740
aacatatccg gagtgtactc cgacgatttt cccaatcaac cgccgataaa attcgattac 1800
acgaatttta acgttagtac ggattacgag taccggatgt tgtttcccga gagattaacg 1860
agcgcgaaga tcttaaaatt caattcgacg gtcgagatcg ttctgcaaaa cacggcgatg 1920
atcacagcgg aaagtcaccc gatgcacctt cacgggttca atttccatgt gttgggtcaa 1980
gggttcggca actatgaacc gagccgagac gtgggaaagc tgaacttggt taacccgcag 2040
atgcgtaaca ccatcggtgt gccgcccggt ggatgggttg tcctcagatt cgtggccaat 2100
aacccgggtt agagatttaa catatgattc tagtttctat caaatatatt attaattaag 2160
aaaatatcaa ttaaaataca caattttccc gcataattat gctaactatt tcaaactttc 2220
agataaatga ttaaacgttc aaattgttac ttgatttctg tctcgaaata gtacatttttc 2280
aaaatatcga ccaaccatta tttccttctc gatcgctgtg gtttggtggt agtgtaatat 2340
cttgagaatt catatatttg ttatatgaaa ttttttttaat tgttagcgat tcaacatatg 2400
attctagttt ctatcaaata tattaattaa tacataaaa tatacattttt 2460
tttaaaaaaa aatatatcat tttttttcaa aacattcaaa atgtagacca accgttgttt 2520
aaccccatta ttttattctc accggcttct aaatgatgtt attgttctaa taaaaattcg 2580
gtaatatttt gagagttcac atatttattt atatgaaaaa tttaattaca tagataccta 2640
tattaaaact agttttatata cttaattagg attttttttg acaacttatg tcatacttac 2700
taagttttgt tttgttaatt agttagaaaa gttgtgaaat atgagaacta atctttgata 2760
tatacgaacc gtgtaggtgt gtggatgttc cattgtcaca tggatgcaca tttgccgtac 2820
ggaataatta tggctttcat cgtccaaaac ggaccacatc cggcgaccag cttgccgccg 2880
ccgccgttgg atcatctcga atgttgtcgg gacgccgaaa tctataacca tcctacgtac 2940
gaccaatatt aattcctcct cctagataga aagagcagat aaaaaaataa catttgtgaa 3000
tattctcctt cccctaacac ctgtgattca accggttctc tggaaggttt taatgctgca 3060
gttagggttt ggaagcttct atcggttatt aaattgtctc tatgggttga agaccattgc 3120
agattggttt ggtttctgca atctatcgaa cctcatcgac tgtga            3165

SEQ ID NO: 2              moltype = DNA   length = 1743
FEATURE                  Location/Qualifiers
misc_feature            1..1743
                         note = cDNA for ChLac8 from C. Hassleriana
source                   1..1743
                         mol_type = other DNA
                         organism = synthetic construct
SEQUENCE: 2
atggccagtt ttgagtgctt tctcatctgc tttgttctta tcctcctccc ttcttcttcg   60
tcgaaggctt atgcatctgt cgtcgaacac actttccttg tccaaaactt cacggcgaaa  120
ccgttgtgca aagagcaggt gataccgaca gttaacggaa gtcttccggg tccgacggta  180
aacgtcagag agggagacac acttattgtt catgtcgtta acaactcccc ttttaacgtc  240
accattcact ggcatggagt gtttcagttg atgagtgcgt ggatggatgg aacagatatg  300
ataacacaat atccgatccg accggaagat aggttcactt ataagtttaa cgtcacagga  360
caagaaggta cgctgcactg gcacgcacat gtcgttaacc tacgcgccac cctgcacggt  420
gctcttgtca tccgtcctcg agctggtcgg ccttatcctt tcccgaaccc tatgaagaa  480
gctctcatca ttctcgaaca atggtggaac accgatatcg aaaatctcca actaaggccc  540
gctcctcttt cagatgccta cctcatcaac ggattagcag gagattcatt cgattcatca  600
cggaataaaa tgtttaaact agaggtggta caaggaaaac ggtacttgct aaggatcata  660
aacgcagcac ttaactcaca tctattcttc aagatagcga accattcctt gcgagtcgtg  720
gccttagacg ccgtctacac gaatccttac gttaccgaca tcgttgtcct aacgccagga  780
cagaccgtag acgcacttct ccatgcagac caaaccctag gctcatacta catgaccact  840
cagctttacg tcagcgccac aggccagcca ttccccgaca aaaccctagc caatgctctc  900
```

```
gttgtctacc aaggtgccac gtcatcgtcc cgcgccatgc catcgttgcc cgacgtgacg   960
gatacgcaga cagcgtatag attctcctcg agtatcaccg gccttgtcag tgggccccat  1020
tggaggccgg tgcctcgcaa cgtggacgag aggatgttta tgaccatggg gttaggtctt  1080
gagcaatgtc caccgagcat gcagtgtccc ggactgtacg gacaacaatt cgcaggctcg  1140
ctgaacaacc gctcgttcga aaatcccaag acatttccca tgcaagaggc ttatttctac  1200
aacatatccg gagtgtactc cgacgatttt cccaatcaac cgccgataaa attcgattac  1260
acgaattta acgttagtac ggattacgag taccggatgt tgtttcccga gagattaacg  1320
agcgcgaaga tcttaaaatt caattcgacg gtcgagatcg ttctgcaaaa cacggcgatg  1380
atcacagcgg aaagtcaccc gatgcacctt cacgggttca atttccatgt gttgggtcaa  1440
gggttcggca actatgaacc gagccgagac gtgggaaagc tgaacttggt taacccgcag  1500
atgcgtaaca ccatcggtgt gccgcccggt ggatggggttg tcctcagatt cgtggccaat  1560
aacccgggtg tgtggatgtt ccattgtcac atggatgcac atttgccgta cggaataatt  1620
atggctttca tcgtccaaaa cggaccacat ccggcgacca gcttgccgcc gccgccgttg  1680
gatcatctcg aatgttgtcg ggacgccgaa atctataacc atcctacgta cgaccaatat  1740
taa                                                                1743
```

```
SEQ ID NO: 3               moltype = AA  length = 580
FEATURE                    Location/Qualifiers
source                     1..580
                           mol_type = protein
                           organism = Cleome hassleriana
SEQUENCE: 3
MASFECFLIC FVLILLPSSS SKAYASVVEH TFLVQNFTAK PLCKEQVIPT VNGSLPGPTV   60
NVREGDTLIV HVVNNSPFNV TIHWHGVFQL MSAWMDGTDM ITQYPIRPED RFTYKFNVTG  120
QEGTLHWHAH VVNLRATLHG ALVIRPRAGR PYPFPEPYEE ALIILEQWWN TDIENLQLRP  180
APLSDAYLIN GLAGDSFDCS RNKMFKLEVV QGKRYLLRII NAALNSHLFF KIANHSLRVV  240
ALDAVYTNPY VTDIVVLTPG QTVDALLHAD QTLGSYYMTT QLYVSATGQP FPDKTLANAL  300
VVYQGATSSS RAMPSLPDVT DTQTAYRFSS SITGLVSGPH WRPVPRNVDE RMFMTMGLGL  360
EQCPPSMQCP GLYGQQFAGS LNNRSFENPK TFPMQEAYFY NISGVYSDDF PNQPPIKFDY  420
TNFNVSTDYE YRMLFPERLT SAKILKFNST VEIVLQNTAM ITAESHPMHL HGFNFHVLGQ  480
GFGNYEPSRD VGKLNLVNPQ MRNTIGVPPG GWVVLRFVAN NPGVWMFHCH MDAHLPYGII  540
MAFIVQNGPH PATSLPPPPL DHLECCRDAE IYNHPTYDQY              580
```

RECOMBINANT LAC POLYNUCLEOTIDES AND USES THEREOF TO INCREASE PRODUCTION OF C-LIGNIN IN PLANTS

CROSS-REFERENCE TO RELATED APPLICATIONS

This application is a continuation of copending application Ser. No. 17/528,375, filed Nov. 17, 2021, which claims the benefit of and priority to U.S. Provisional Patent Application No. 63/114,834, filed on Nov. 17, 2020, the contents of which are incorporated by reference herein in their entireties.

STATEMENT REGARDING FEDERALLY SPONSORED RESEARCH OR DEVELOPMENT

This invention was made with Government support under grant 1456286, awarded by the National Science Foundation. The Government has certain rights in the invention.

This invention was made with Government support under grant DE-AC05-00OR22725, awarded by the US Department of Energy. The Government has certain rights in the invention.

SEQUENCE LISTING

This application contains a sequence listing filed in ST.26 format entitled "921402-1071 Sequence Listing" created on Jan. 3, 2024, and having 9,375 bytes. The content of the sequence listing is incorporated herein in its entirety.

BACKGROUND

Lignin is the second most abundant biological polymer on earth, after cellulose, and is a major functional component of plant cell walls. Since lignin is also a major byproduct of industrial processes (such as biofuel production) that use cellulosic biomass, there is interest in downstream uses of lignin byproducts. Catechyl lignin (C-lignin) is a unique form of naturally-occurring lignin formed from polymerization of caffeyl alcohol. A linear homopolymer of caffeyl alcohol, C-lignin is found in the seed coats of diverse plant species. Its properties and unique structure make it a potentially valuable natural source of carbon fibers and high-value chemicals.

Unfortunately, the natural production of C-lignin by plants is limited, sometimes being produced in only certain plant tissues (such as seed coats). Its production is also often temporally restricted, thereby limiting possible natural sources of C-lignin. A desire to engineer plants, such as biomass crops, to introduce or produce increased amounts of C-lignin has led to an interest in elucidating the mechanism of in planta polymerization of caffeyl alcohol, which has remained unclear.

SUMMARY

In various aspects described herein, recombinant LAC polynucleotides encoding a laccase (LAC) polypeptide capable of polymerizing caffeyl alcohol are provided, as well as vectors, cells, and transgenic plants including the recombinant LAC polynucleotide. Methods of increasing production of C-lignin in plants using the recombinant LAC polynucleotides, vectors, cells and plants of the present disclosure are also provided.

In some aspects described herein, the present disclosure provides recombinant polynucleotides including: a LAC polynucleotide encoding a laccase (LAC) polypeptide capable of polymerizing caffeyl alcohol, the LAC polynucleotide having a sequence that is about 50-100% identical to LAC8 from *Cleome hassleriana* (ChLAC8) having SEQ ID NO: 1; and at least one heterologous polynucleotide sequence operatively linked to the LAC polynucleotide. According to some aspects, the LAC polynucleotide encodes a polypeptide having 80-100% sequence identity to LAC8 from *Cleome hassleriana* (ChLAC8) having SEQ ID NO: 3 and having a glutamine residue in an active site position of the polypeptide configured to be in substantial proximity to interact with a 3 hydroxyl group of a caffeyl alcohol bound in an active site of the polypeptide. Also provided are vectors and/or cells including the recombinant LAC polynucleotide of the present disclosure.

According to some aspects of the present disclosure, recombinant polynucleotides that encode laccase (LAC) polypeptide capable of polymerizing caffeyl alcohol are provided, where the recombinant polynucleotide includes a LAC polynucleotide having a sequence that is about 80-100% identical to the cDNA for LAC8 from *Cleome hassleriana* (ChLAC8) having SEQ ID NO: 2.

Aspects of the present disclosure also include transgenic plants including a plurality of plant cells where one or more of the cells includes a recombinant LAC polynucleotide of the present disclosure. According to some aspects, the transgenic plants of the present disclosure cane express an increased amount of LAC polypeptides capable of polymerizing caffeyl alcohol, as compared to a corresponding non-transgenic control plant.

Further aspects of the present disclosure include methods of increasing production of C-lignin in a plant by providing a plant having one or more cells comprising the recombinant LAC polynucleotide of the present disclosure, and growing the plant in the presence of caffeyl alcohol. According to aspects, the recombinant LAC polynucleotide is integrated into the genome of the one or more cells or housed on a vector in the one or more cells, such that the recombinant polynucleotide is expressed in the one or more plant cell and is overexpressed in the plant relative to a wild-type plant, such that the plant produces C-lignin. In such embodiments, the caffeyl alcohol can be externally provided, synthesized by the plant, or both Other systems, methods, features, and advantages of the LAC polynucleotides, vectors, cells, and transgenic plants of the present disclosure and methods of increasing production of C-lignin in plants will be apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Further aspects of the present disclosure will be more readily appreciated upon review of the detailed description of its various embodiments, described below, when taken in conjunction with the accompanying drawings. The components in the drawings are not necessarily to scale, emphasis instead being placed upon clearly illustrating the principles of the present disclosure. Moreover, in the drawings, like reference numerals designate corresponding parts throughout the several views.

FIG. 1A is a hierarchical clustering analysis of transcript levels of 32 ChLAC *Cleome* genes in different tissues and different stages of seed development. FPKM values (transcript levels) were transformed to log 2(FPKM+1) for color scaling. The heatmap was drawn using the 'pheatmap' package in R software. The heatmap also shows the transcript levels of ChCAD5 (involved in C-lignin biosynthesis), ChCOMT1/2 and ChCoAOMT1/5 (encoding enzymes of G-lignin biosynthesis down-regulated at the onset of C-lignin biosynthesis), and ChANR (associated with condensed tannin biosynthesis).

FIG. 1B illustrates a gene structure analysis of ChLAC8 showing that ChLAC8X1, ChLAC8X2 and ChLAC8X3 arise from the same gene locus (LOC104823484) due to alternative splicing. The red box shows the third intron where the alternative splicing event takes place.

FIG. 1C is a graph illustrating transcription levels of the three ChLAC8 transcript variants. DAP=days after pollination for seed coat samples.

FIG. 1D illustrates a phylogenetic tree of laccases from *C. hassleriana* and other plants. The tree was constructed using MEGA 7.0 software with neighboring-joining phylogeny testing and 1000 bootstrap replicates, showing *Cleome* ChLACs, AtLACs from *Arabidopsis*, and the *Medicago* laccases (MtLACs). The functionally characterized AtLACs (AtLAC4, 11, 15 and 17) are indicated by triangles. The ChLAC8 characterized in this study is marked by a circle. The accession numbers of the laccases are given below.

FIGS. 2A-2F illustrate HPLC chromatograms of reactions of ChLAC8 with caffeyl alcohol (FIGS. 2A, 2B, peak1), coniferyl alcohol (FIGS. 2C, 2D, peak 2) and sinapyl alcohol (FIGS. 2E, 2F, peak 3). FIGS. 2A, 2C and 2E show reactions incubated without recombinant enzyme, and FIGS. 2B, 2D and 2F show reactions 30 min after incubation with recombinant ChLAC8.

FIGS. 2G-L show extracted ion chromatograms (EICs), scanned at m/z=329 for the dimer of caffeyl alcohol (FIG. 2H, peak 5), m/z=357 for the dimer of coniferyl alcohol (FIGS. 2I, 2J), or m/z=417 for the dimer of sinapyl alcohol (FIG. 2L, peak 7). (−) Indicates control assays without ChLAC8. No dimers were detected in the corresponding control reactions (FIG. 2G, peak 4; FIGS. 2I, K, peak 6) or the reaction of ChLAC8 toward coniferyl alcohol (FIG. 2J).

FIG. 3A illustrates a modeled structure of ChLAC8 with sinapyl alcohol docked into the active site. FIG. 3B shows active site residues showing binding of caffeyl alcohol. FIG. 3C shows active site residues showing binding of sinapyl alcohol. FIG. 3D illustrates active site residues showing binding of coniferyl alcohol. Caffeyl alcohol, sinapyl alcohol and coniferyl alcohol are shown as a stick model. Some key protein residues in the active site and binding pocket are labeled and shown as stick models, and T1 Cu is shown as a sphere model. The predicted hydrogen bonds are indicated by dashed lines.

FIGS. 4A-4C are color digital images illustrating visible phenotypes of ChLAC8 downregulated and null-segregant plants. Plants grown in the greenhouse for 2 months (FIG. 4A), 3 months (FIG. 4B) and 4 months (mature flowering plants (FIG. 4C). FIG. 4 D is a color digital image illustrating seed coat phenotypes at 8, 12, 16 and 20 DAP. FIG. 4E is a graph illustrating transcription levels of ChLAC8 in the seed coats at 16 days after pollination. The graph of FIG. 4F illustrates the C/G ratio in the seed coat at 20 and 24 DAP as determined by thioacidolysis. FIG. 4G illustrates lignin content in the seed coat at 20 and 24 DAP as determined by thioacidolysis. Two independent $T_2$ transgenic lines (9, 27) were analyzed and compared with null segregant plants. Approximately 2 mg dry weight of seed coats were used for thioacidolysis analysis per replicate. Data are means±SE derived from three biological replicates. Filled in circles, triangles and squares represent individual data points. The asterisks indicate significant differences at the P≤0.05* or P≤0.01** level by unpaired two-tailed Student's t-test.

FIGS. 5A-5G provide illustration of the scheme for the synthesis of $^{13}$C6-caffeyl and $^{13}$C6-coniferyl alcohols. FIG. 5A illustrates a scheme for the synthesis of $^{13}$C6-caffeyl alcohol.

FIGS. 5B-D illustrate LC-MS/MS analysis of $^{13}$C6-caffeic acid (FIG. 5B), $^{13}$C6-caffeic acid methyl ester (FIG. 5C) and $^{13}$C6-caffeyl alcohol (FIG. 5D). FIG. 5E illustrates a scheme for the synthesis of $^{13}$C6-coniferyl alcohol. (FIGS. 5F, 5G) LC-MS/MS analysis of $^{13}$C6-ferulic acid ethyl ester (FIG. 5F) and $^{13}$C6-coniferyl alcohol (FIG. 5G).

FIGS. 6A-6I illustrate use of thioacidolysis to reveal lignin labeling in the $^{13}$C monolignol feeding experiments.

FIG. 6A illustrates a labeling pattern, structures and masses of monolignol fragments obtained after thioacidolysis from lignin extracted from tissues fed with labeled $^{13}$C6-caffeyl alcohol or $^{13}$C6-coniferyl alcohol. The thiol group (—SEt) displaces the α-hydroxyl, α-ether, and β-aryl groups during thioacidolysis. The bar indicates the cleavage at the C7-C8 bond during the MS analysis, resulting in the primary fragments at m/z 327 and 269 from the benzylic cation of the trimethylsilylated (TMS) derivatives of unlabeled monolignols and at m/z 333 and 275 of the TMS derivatives of $^{13}$C$_6$-labeled monolignols.

FIGS. 6B, 6C, FIG. 6F, 6G illustrate extracted ion chromatograms (EICs) showing $^{13}$C-labeled and unlabeled monolignol thioacidolysis products after separation during GC. Double peaks in the EICs represent the presence of threo- and erythro-isomers of the tri-thioetherates shown in (FIG. 6A). EICs of transgenic *Medicago* hairy root line L6 are deployed here as an example. The no-monolignol-fed sample (FIGS. 6B, 6F) showed a clear doublet corresponding to the m/z of the unlabeled thioacidolysis products, with no doublet at the m/z of the labeled products. Lignin from samples that were fed with $^{13}$C$_6$-caffeyl (FIG. 6C) or $^{13}$C$_6$-coniferyl (FIG. 6G) alcohol could incorporate labelled precursors exhibited both M+6 and unlabeled monolignol-derived products.

FIGS. 6D, 6E, 6H, 6I are traces showing the relative abundance of $^{13}$C-labeled and unlabeled monolignol thioacidolysis products after fragmentation during MS. Traces correspond to the monolignol thioacidolysis product peaks shown in FIGS. 6B, 6C, 6F and 6G. Samples that were fed with $^{13}$C$_6$-caffeyl (FIG. 6E) or $^{13}$C$_6$-coniferyl (FIG. 6I) alcohols showed an increased ratio of M+6 monolignol-derived fragmentation products to the unlabeled ions.

FIGS. 7A-7I are a series of graphs illustrating incorporation of exogenous monolignols into lignin of *M. truncatula* comt mutant hairy root cultures expressing ChLAC8. FIG. 7A shows ChLAC8 transcript levels as determined by qRT-PCR, expressed relative to Tubulin as a housekeeping gene. FIGS. 7B-7E illustrate lignin monomer thioacidolysis yields for hydroxyphenyl (FIG. 7A), caffeyl (FIG. 7B), guaiacyl (FIG. 7C), and syringyl (FIG. 7D) lignin units in the hairy roots. The yields for 5-hydroxyguaiacyl units were under the limit of quantification. Values shown are percentages of total lignin units in hairy root tissues.

FIGS. 7F, 7H illustrate lignin monomer thioacidolysis yields for labeled caffeyl (FIG. 7F) and guaiacyl (FIG. 7H) units in the hairy roots when $^{13}$C6-caffeyl (FIG. 7F) or $^{13}$C6-coniferyl (FIG. 7G) alcohols were applied, respectively. No labeled guaiacyl (FIG. 7F) or syringyl (FIG. 7H) units were detected. Values shown are percentages of total lignin units in hairy root tissues.

FIGS. 7G, 7I illustrate the percentage incorporation of $^{13}$C6-caffeyl (FIG. 7G) or $^{13}$C6-coniferyl (FIG. 7I) alcohols into caffeyl (FIG. 7G) and guaiacyl (FIG. 7I) units of lignin. Hairy root sections were incubated with 100 μM $^{13}C_6$-caffeyl alcohol or $^{13}C_6$-coniferyl alcohol for 2 days prior to extraction of lignin and analysis by thioacidolysis. Four independent lines expressing ChLAC8 (L) were analyzed and compared with two lines expressing GUS (G), all in the comt mutant background. For each biological replicate, approximately 100 mg of hairy root cultures harvested from one tissue culture dish was put into one well. Data are means of three biological replicates (after averaging two analytical replicates). Error bars indicate standard deviations. The different letters above the bars represent statistically significant differences determined by one-way ANOVA (Duncan, $p \leq 0.05$) with SPSS Statistics (version 22; IBM).

FIGS. 8A-8F are a series of graphs illustrating lignin composition in stems of *Arabidopsis thaliana* comt mutant expressing ChLAC8. FIG. 8A illustrates ChLAC8 transcript levels in inflorescence stems as determined by qRT-PCR, expressed relative to Tubulin as a housekeeping gene. FIGS. 8AB-8F illustrate lignin monomer thioacidolysis yields for hydroxyphenyl (FIG. 8B), caffeyl (FIG. 8C), guaiacyl (FIG. 8D), 5-hydroxyguaiacyl (FIG. 8E), and syringyl (FIG. 8F) units in inflorescence stems. Values shown are percentages of total lignin units in stem tissues. Four independent homozygous $T_3$ transgenic lines expressing ChLAC8 (L) were analyzed and compared with two lines expressing GUS (G), all in the comt mutant background. For each biological replicate, the inflorescence stems were harvested from three plants. Data are means of three biological replicates (after averaging two analytical replicates). Error bars indicate standard deviations. The different letters above the bars represent statistically significant differences determined by one-way ANOVA (Duncan, $p \leq 0.05$) with SPSS Statistics (version 22; IBM).

FIGS. 9A-9C illustrate lignin monomer thioacidolysis yields for hydroxyphenyl (FIG. 9A), caffeyl (FIG. 9B), and guaiacyl (FIG. 9C) units. The yields for 5-hydroxyguaiacyl and syringyl units were under the limit of quantification. Values shown are percentages of total lignin units in stem tissues. FIG. 9D illustrates the percentage incorporation of $^{13}$C6-caffeyl alcohol into caffeyl units. No labeled guaiacyl, 5-hydroxyguaiacyl, or syringyl units were detected. Cut stems were incubated with 100 μM $^{13}$C6-caffeyl alcohol for 2 days prior to extraction of lignin and analysis by thioacidolysis. Four independent lines expressing ChLAC8 (L) were analyzed and compared with two lines expressing GUS (G), all in the comt mutant background. For each biological replicate, five stem fragments were harvested. Data for lignin composition are means of three biological replicates (after averaging two analytical replicates). Error bars indicate standard deviations. The different letters above the bars represent statistically significant differences determined by one-way ANOVA (Duncan, $p \leq 0.05$) with SPSS Statistics (version 22; IBM).

DETAILED DESCRIPTION

Figure 1A:
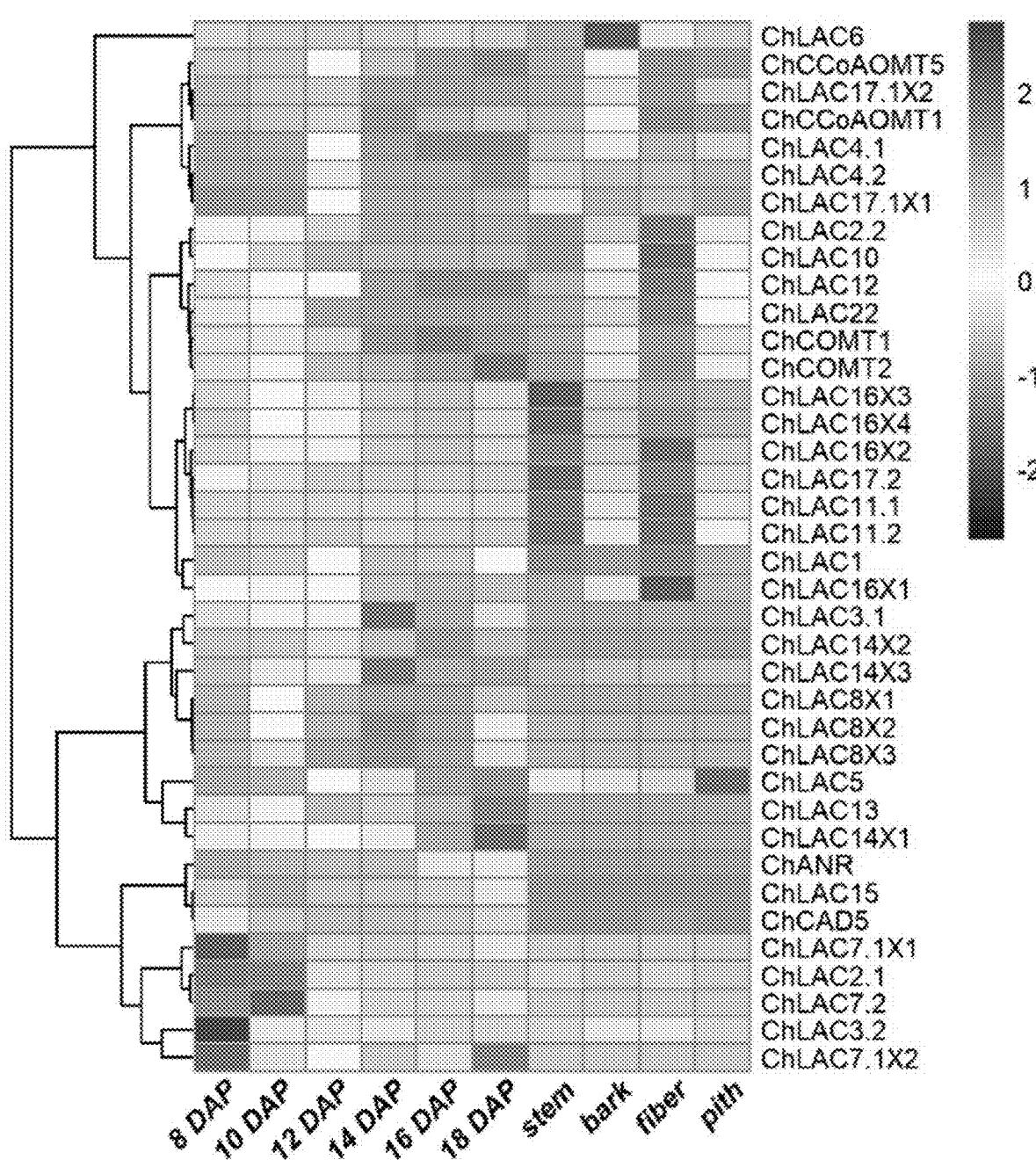
FIGS. 1A-1D illustrate transcript level profiles and phylogenetic analysis of laccases derived from *C. hassleriana*.

Before the present disclosure is described in greater detail, it is to be understood that this disclosure is not limited to particular embodiments described, and as such may, of course, vary. It is also to be understood that the terminology used herein is for the purpose of describing particular embodiments only and is not intended to be limiting.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are cited to disclose and describe the methods and/or materials in connection with which the publications are cited. Any such publications and patents that are herein incorporated by reference, as noted, are incorporated as if each individual publication or patent were specifically and individually indicated to be incorporated by reference. Such incorporation by reference is expressly limited to the methods and/or materials described in the cited publications and patents and does not extend to any lexicographical definitions from the cited publications and patents. Any lexicographical definition in the publications and patents cited that is not also expressly repeated in the instant application should not be treated as such and should not be read as defining any terms appearing in the accompanying claims. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Where a range is expressed, a further aspect includes from the one particular value and/or to the other particular value. Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure. For example, where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In addition, the phrase "about 'x' to 'y'", where 'x' and 'y' are numerical values, includes "about 'x' to about 'y'".

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further aspect. For example, if the value "about 10" is disclosed, then "10" is also disclosed.

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range.

As used herein, "about," "approximately," "substantially," and the like, when used in connection with a numerical variable, can generally refers to the value of the variable and to all values of the variable that are within the experimental error (e.g., within the 95% confidence interval for the mean) or within +/−10% of the indicated value, whichever is greater. As used herein, the terms "about," "approximate," "at or about," and "substantially" can mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

Embodiments of the present disclosure will employ, unless otherwise indicated, techniques of molecular biology, microbiology, genetic engineering, organic chemistry, biochemistry, physiology, cell biology, plant physiology, plant pathology, and the like, which are within the skill of the art. Such techniques are explained fully in the literature.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only and is not intended to be limiting. It is also possible in the present disclosure that steps can be executed in different sequence where this is logically possible unless the context clearly dictates otherwise.

Prior to describing the various embodiments, the following definitions are provided and should be used unless otherwise indicated.

Definitions

In describing and claiming the disclosed subject matter, the following terminology will be used in accordance with the definitions set forth below.

It must be noted that, as used in the specification and the appended claims, the singular forms "a," "an," and "the" include plural referents unless the context clearly dictates otherwise. Thus, for example, reference to "a cell" includes a plurality of cells. In this specification and in the claims that follow, reference will be made to a number of terms that shall be defined to have the following meanings unless a contrary intention is apparent.

As used herein, the following terms have the meanings ascribed to them unless specified otherwise. In this disclosure, "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above) that do not materially affect the basic and novel characteristic(s) of the compositions or methods, compared to those of the corresponding compositions or methods disclosed herein. "Consisting essentially of" or "consists essentially" or the like, when applied to methods and compositions encompassed by the present disclosure have the meaning ascribed in U.S. Patent law, allowing for the presence of more than that which is recited so long as basic or novel characteristics of that which is recited is not changed by the presence of more than that which is recited, but excludes prior art embodiments.

As used herein, "cDNA" refers to a DNA sequence that is complementary to a RNA transcript in a cell. It is a man-made molecule. Typically, cDNA is made in vitro by an enzyme called reverse-transcriptase using RNA transcripts as templates.

As used herein with reference to the relationship between DNA, cDNA, mRNA, RNA, protein/peptides, and the like "corresponding to" or "encoding" (used interchangeably herein) refers to the underlying biological relationship between these different molecules. As such, one of skill in the art would understand that operatively "corresponding to" can direct them to determine the possible underlying and/or resulting sequences of other molecules given the sequence of any other molecule which has a similar biological relationship with these molecules. For example, from a DNA sequence an RNA sequence can be determined and from an RNA sequence a cDNA sequence can be determined.

As used herein, "deoxyribonucleic acid (DNA)" and "ribonucleic acid (RNA)" can generally refer to any polyribonucleotide or polydeoxyribonucleotide, which may be unmodified RNA or DNA or modified RNA or DNA. RNA can be in the form of non-coding RNA such as tRNA (transfer RNA), snRNA (small nuclear RNA), rRNA (ribosomal RNA), anti-sense RNA, RNAi (RNA interference construct), siRNA (short interfering RNA), microRNA (miRNA), or ribozymes, aptamers, guide RNA (gRNA) or coding mRNA (messenger RNA).

As used herein, "DNA molecule" can include nucleic acids/polynucleotides that are made of DNA.

As used herein, the term "encode" refers to principle that DNA can be transcribed into RNA, which can then be translated into amino acid sequences that can form proteins.

As used herein, "expression" refers to the process by which polynucleotides are transcribed into RNA transcripts. In the context of mRNA and other translated RNA species, "expression" also refers to the process or processes by which the transcribed RNA is subsequently translated into peptides, polypeptides, or proteins. In some instances, "expression" can also be a reflection of the stability of a given RNA. For example, when one measures RNA, depending on the method of detection and/or quantification of the RNA as well as other techniques used in conjunction with RNA detection and/or quantification, it can be that increased/decreased RNA transcript levels are the result of increased/decreased transcription and/or increased/decreased stability and/or degradation of the RNA transcript. One of ordinary skill in the art will appreciate these techniques and the relation "expression" in these various contexts to the underlying biological mechanisms.

As used herein, "gene" can refer to a hereditary unit corresponding to a sequence of DNA that occupies a specific location on a chromosome and that contains the genetic instruction for a characteristic(s) or trait(s) in an organism. The term gene can refer to translated and/or untranslated regions of a genome. "Gene" can refer to the specific sequence of DNA that is transcribed into an RNA transcript that can be translated into a polypeptide or be a catalytic RNA molecule, including but not limited to, tRNA, siRNA, piRNA, miRNA, long-non-coding RNA and shRNA.

As used herein, "identity," can refer to a relationship between two or more nucleotide or polypeptide sequences, as determined by comparing the sequences. In the art, "identity" can also refer to the degree of sequence relatedness between nucleotide or polypeptide sequences as determined by the match between strings of such sequences. "Identity" can be readily calculated by known methods, including, but not limited to, those described in (Computational Molecular Biology, Lesk, A. M., Ed., Oxford University Press, New York, 1988; Biocomputing: Informatics and Genome Projects, Smith, D. W., Ed., Academic Press, New York, 1993; Computer Analysis of Sequence Data, Part I, Griffin, A. M., and Griffin, H. G., Eds., Humana Press, New Jersey, 1994; Sequence Analysis in Molecular Biology, von Heinje, G., Academic Press, 1987; and Sequence Analysis Primer, Gribskov, M. and Devereux, J., Eds., M Stockton Press, New York, 1991; and Carillo, H., and Lipman, D., SIAM J. Applied Math. 1988, 48: 1073. Preferred methods to determine identity are designed to give the largest match between the sequences tested. Methods to determine identity are codified in publicly available computer programs. The percent identity between two sequences can be determined by using analysis software (e.g., Sequence Analysis Software Package of the Genetics Computer Group, Madison Wis.) that incorporates the Needelman and Wunsch, (J. Mol. Biol., 1970, 48: 443-453,) algorithm (e.g., NBLAST, and XBLAST). The default parameters are used to determine the identity for the polypeptides of the present disclosure, unless stated otherwise.

As used herein, "nucleic acid," "nucleotide sequence," and "polynucleotide" can be used interchangeably herein and can generally refer to a string of at least two base-sugar-phosphate combinations and refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, polynucleotide as used herein can refer to triple-stranded regions comprising RNA or DNA or both RNA and DNA. The strands in such regions can be from the same molecule or from different molecules. The regions may include all of one or more of the molecules, but more typically involve only a region of some of the molecules. One of the molecules of a triple-helical region often is an oligonucleotide. "Polynucleotide" and "nucleic acids" also encompasses such chemically, enzymatically or metabolically modified forms of polynucleotides, as well as the chemical forms of DNA and RNA characteristic of viruses and cells, including simple and complex cells, inter alia. For instance, the term polynucleotide as used herein can include DNAs or RNAs as described herein that contain one or more modified bases. Thus, DNAs or RNAs including unusual bases, such as inosine, or modified bases, such as tritylated bases, to name just two examples, are polynucleotides as the term is used herein. "Polynucleotide", "nucleotide sequences" and "nucleic acids" also includes PNAs (peptide nucleic acids), phosphorothioates, and other variants of the phosphate backbone of native nucleic acids. Natural nucleic acids have a phosphate backbone, artificial nucleic acids can contain other types of backbones, but contain the same bases. Thus, DNAs or RNAs with backbones modified for stability or for other reasons are "nucleic acids" or "polynucleotides" as that term is intended herein. As used herein, "nucleic acid sequence" and "oligonucleotide" also encompasses a nucleic acid and polynucleotide as defined elsewhere herein.

As used herein, "operatively linked" in the context of recombinant DNA molecules, vectors, and the like refers to the regulatory and other sequences useful for expression, stabilization, replication, and the like of the coding and transcribed non-coding sequences of a nucleic acid that are placed in the nucleic acid molecule in the appropriate positions relative to the coding sequence so as to effect expression or other characteristic of the coding sequence or transcribed non-coding sequence. This same term can be applied to the arrangement of coding sequences, non-coding and/or transcription control elements (e.g. promoters, enhancers, and termination elements), and/or selectable markers in an expression vector. "Operatively linked" can also refer to an indirect attachment (i.e. not a direct fusion) of two or more polynucleotide sequences or polypeptides to each other via a linking molecule (also referred to herein as a linker).

As used herein, "organism", "host", and "subject" refers to any living entity comprised of at least one cell. A living organism can be as simple as, for example, a single isolated eukaryotic cell or cultured cell or cell line, or as complex as a mammal, including a human being, and animals (e.g., vertebrates, amphibians, fish, mammals, e.g., cats, dogs, horses, pigs, cows, sheep, rodents, rabbits, squirrels, bears, primates (e.g., chimpanzees, gorillas, and humans). These terms also contemplate plants, fungi, bacteria, etc.

As used herein, "overexpressed" or "overexpression" refers to an increased expression level of an RNA and/or protein product encoded by a gene as compared to the level of expression of the RNA or protein product in a normal or control cell. The amount of increased expression as compared to a normal or control cell can be about 0.1, 0.2, 0.3, 0.4, 0.5, 0.6, 0.7, 0.8, 0.9, 1.0, 1.2, 1.3, 1.4, 1.5, 1.6, 1.7, 1.8, 1.9, 2.0, 2.2, 2.4, 2.6, 2.8, 3.0, 3.3, 3.6, 3.9, 4.0, 4.4, 4.8, 5.0, 5.5, 6, 6.5, 7, 7.5, 8.0, 8.5, 9, 9.5, 10, 11, 12, 13, 14, 15, 16, 17, 18, 19, 20, 25, 30, 35, 40, 45, 50, 60, 70, 0, 90, 100 fold or more greater than the normal or control cell.

As used herein, the terms "optional" or "optionally" means that the subsequently described event or circumstance can or cannot occur, and that the description includes instances where said event or circumstance occurs and instances where it does not.

As used herein, "plasmid" refers to a non-chromosomal double-stranded DNA sequence including an intact "replicon" such that the plasmid is replicated in a host cell.

As used herein, "polypeptides" or "proteins" refers to amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V). "Protein" and "Polypeptide" can refer to a molecule composed of one or more chains of amino acids in a specific order. The term protein is used interchangeable with "polypeptide." The order is determined by the base sequence of nucleotides in the gene coding for the protein. Proteins can be required for the structure, function, and regulation of the body's cells, tissues, and organs.

As used herein, "promoter" includes all sequences capable of driving transcription of a coding or a non-coding sequence. In particular, the term "promoter" as used herein refers to a DNA sequence generally described as the 5' regulator region of a gene, located proximal to the start codon. The transcription of an adjacent coding sequence(s) is initiated at the promoter region. The term "promoter" also includes fragments of a promoter that are functional in initiating transcription of the gene.

As used herein, the term "recombinant" or "engineered" can generally refer to a non-naturally occurring nucleic acid, nucleic acid construct, or polypeptide. Such non-naturally occurring nucleic acids may include natural nucleic acids that have been modified, for example that have deletions, substitutions, inversions, insertions, etc., and/or combinations of nucleic acid sequences of different origin that are joined using molecular biology technologies (e.g., a nucleic acid sequences encoding a fusion protein (e.g., a protein or polypeptide formed from the combination of two different proteins or protein fragments), the combination of a nucleic acid encoding a polypeptide to heterologous sequence (e.g., a regulatory sequence such as, but not limited to, a promoter sequence or other transcription control elements, where the coding sequence and heterologous sequence are from different sources or otherwise do not typically occur together naturally (e.g., a nucleic acid and a constitutive promoter), etc. Recombinant or engineered can also refer to the polypeptide encoded by the recombinant nucleic acid. Non-naturally occurring nucleic acids or polypeptides include nucleic acids and polypeptides modified by man.

As used herein, "selectable marker" refers to a gene whose expression allows one to identify cells that have been transformed or transfected with a vector containing the marker gene. For instance, a recombinant nucleic acid may include a selectable marker operatively linked to a gene of interest and a promoter, such that expression of the selectable marker indicates the successful transformation of the cell with the gene of interest.

A "suitable control" is a control that will be instantly appreciated by one of ordinary skill in the art as one that is included such that it can be determined if the variable being evaluated has an effect, such as a desired effect or hypothesized effect. One of ordinary skill in the art will also instantly appreciate based on inter alia, the context, the variable(s), the desired or hypothesized effect, what is a suitable or an appropriate control.

As used herein, "transforming" when used in the context of engineering or modifying a cell, refers to the introduction by any suitable technique and/or the transient or stable incorporation and/or expression of an exogenous gene in a cell. It can be used interchangeably in some contexts herein with "transfection".

As used herein, the term "transfection" refers to the introduction of an exogenous and/or recombinant nucleic acid sequence into the interior of a membrane enclosed space of a living cell, including introduction of the nucleic acid sequence into the cytosol of a cell as well as the interior space of a mitochondria, nucleus, or chloroplast. The nucleic acid may be in the form of naked DNA or RNA, it may be associated with various proteins or regulatory elements (e.g., a promoter and/or signal element), or the nucleic acid may be incorporated into a vector or a chromosome.

As used herein, "variant" can refer to a polynucleotide or polypeptide that differs from a reference polynucleotide or polypeptide but retains essential and/or characteristic properties (structural and/or functional) of the reference polynucleotide or polypeptide. A typical variant of a polypeptide differs in amino acid sequence from another, reference polypeptide. The differences can be limited so that the sequences of the reference polypeptide and the variant are closely similar overall and, in many regions, identical. A variant and reference polypeptide may differ in nucleic or amino acid sequence by one or more modifications at the sequence level or post-transcriptional or post-translational modifications (e.g., substitutions, additions, deletions, methylation, glycosylations, etc.). A substituted nucleic acid may or may not be an unmodified nucleic acid of adenine, thiamine, guanine, cytosine, uracil, including any chemically, enzymatically or metabolically modified forms of these or other nucleotides. A substituted amino acid residue may or may not be one encoded by the genetic code. A variant of a polypeptide may be naturally occurring such as an allelic variant, or it may be a variant that is not known to occur naturally. "Variant" includes functional and structural variants.

As used herein, the term "vector" is used in reference to a vehicle used to introduce an exogenous nucleic acid sequence into a cell. A vector may include a DNA molecule, linear or circular (e.g. plasmids), which includes a segment encoding a polypeptide of interest operatively linked to additional segments that provide for its transcription and translation upon introduction into a host cell or host cell organelles. Such additional segments may include promoter and terminator sequences, and may also include one or more origins of replication, one or more selectable markers, an enhancer, a polyadenylation signal, etc. Expression vectors are generally derived from yeast or bacterial genomic or plasmid DNA, or viral DNA, or may contain elements of both.

As used herein, "wild-type" is the typical form of an organism, variety, strain, gene, protein, or characteristic as it occurs in nature, as distinguished from mutant forms that may result from selective breeding or transformation with a transgene.

As used herein, "electroporation" is a transformation method in which a high concentration of plasmid DNA (containing exogenous DNA) is added to a suspension of host cell protoplasts, and the mixture shocked with an electrical field of about 200 to 600 V/cm.

As used herein, a "transgene" refers to an artificial gene which is used to transform a cell of an organism, such as a bacterium or a plant.

As used herein, the term "exogenous DNA" or "exogenous nucleic acid sequence" or "exogenous polynucleotide" refers to a nucleic acid sequence that was introduced into a cell, organism, or organelle via transfection. Exogenous nucleic acids originate from an external source, for instance, the exogenous nucleic acid may be from another cell or organism and/or it may be synthetic and/or recombinant. While an exogenous nucleic acid sometimes originates from a different organism or species, it may also originate from the same species (e.g., an extra copy or recombinant form of a nucleic acid that is introduced into a cell or organism in addition to or as a replacement for the naturally occurring nucleic acid). Typically, the introduced exogenous sequence is a recombinant sequence.

DISCUSSION

In accordance with the purpose(s) of the present disclosure, as embodied and broadly described herein, embodiments of the present disclosure, in some aspects, relate to recombinant LAC polynucleotides encoding a laccase (LAC) polypeptide capable of polymerizing caffeyl alcohol, vectors including the LAC polynucleotides, cells and transgenic plants including the recombinant LAC polynucleotides. The present disclosure also provides methods of increasing production of C-lignin in a plant, including in plants that do not naturally have the ability to produce C-lignin. The recombinant polynucleotides, vectors, cells, transgenic plants, and methods of the present disclosure provide for the ability to produce C-lignin and further understand the biological mechanisms for C-lignin production.

For a long time, it was believed that lignins are only composed of p-hydroxyphenyl (H), guaiacyl (G), and syringyl (S) units derived from the polymerization of the corresponding monolignols p-coumaryl, coniferyl, and sinapyl alcohols, respectively (Vanholme et al., 2019). Increasing evidence has shown that the three classical hydroxycinnamyl alcohols are not the only compounds that can be incorporated into natural lignin, and additional monomers have been found to exist in genetically engineered plants with modifications to the monolignol biosynthetic pathway (Dixon and Barros, 2019). For example, 5-hydroxyguaiacyl units (5HG) can be present in the lignin of transgenic plants with loss of function of caffeic acid/5- hydroxyconiferaldehyde 3/5-O-methyltransferase (COMT) (Ralph et al., 2001; Weng et al., 2010). Moreover, examination of lignin structures from a broader range of plant species has led to the discovery of several new natural lignin building blocks (Annunziata, 2019), such as tricin and resveratrol (Lan et al., 2015; del Rio et al., 2017).

C-lignin is a recently discovered, novel type of lignin, which is wholly derived from caffeyl alcohol. It was initially found in the seed coats of *vanilla* orchid (*Vanilla planifolia*), the ornamental plant *Cleome* (*Cleome hassleriana*), and many members of the Cactaceae (Chen et al., 2012, 2013; Tobimatsu et al., 2013). The linear linkages of benzodioxane units in C-lignin and its homopolymeric nature make it an ideal substrate for the production of carbon fibers and lignin valorization through depolymerization to uniform catechyl-type monomers (Nar et al., 2016; Li et al., 2018; Stone et al., 2018).

In *C. hassleriana*, G-lignin is biosynthesized in the seed coat during the first 6-12 days after pollination (DAP); after that time, G-lignin deposition stops and there is a switch to C-lignin formation (Tobimatsu et al., 2013). Due to this unique pattern of lignin accumulation during seed maturation, *Cleome* has been developed as a model system to investigate C-lignin biosynthesis and polymerization. In previous studies, a complete set of C-lignin monomer biosynthesis genes were identified from *V. planifolia* and *Cleome* transcriptomes through bioinformatic approaches (Rao et al., 2014; Zhuo et al., 2019). Biochemical characterization of several key enzymes, including caffeoyl CoA- and caffeic acid 3-O-methyltransferases (CCoAOMT and COMT) and cinnamyl alcohol dehydrogenase (ChCAD), provided a basis for understanding the mechanism of C-lignin monomer biosynthesis (Zhuo et al., 2019). However, knowledge about C-lignin polymerization is still lacking.

The polymerization of caffeyl alcohol in planta, the final step in C-lignin biosynthesis, is likely to occur via an oxidative enzyme reaction followed by free-radical cross-coupling under simple chemical control, in the same manner as the in planta polymerization of the traditional monolignols (Chen et al., 2012). Oxidative polymerization of monolignols is catalyzed in vitro by two groups of enzyme systems: laccases (EC 1.10.3.2) and class III peroxidases (EC 1.11.17) (Sterjiades et al., 1992; Bao et al., 1993; Barros et al., 2015; Tobimatsu and Schuetz, 2019). However, many aspects of the mechanisms underlying this process remain unclear, as the possession of large gene families for both enzymes makes it generally difficult to interrogate their roles in planta (Duroux and Welinder, 2003; Turlapati et al., 2011).

In recent years, peroxidases were genetically proven to be involved in plant cell wall lignification (Shigeto and Tsutsumi, 2016). In *Arabidopsis thaliana*, cell-specific down-regulation of Peroxidase64 (PRX64) significantly delayed the formation of the Casparian strip, a layer of lignified cells in the root endodermis (Lee et al., 2013). Like peroxidases, the essential functions of laccases in lignification have been revealed by loss of function approaches, using *Arabidopsis*, poplar (*Populus trichocarpa*) and Brachypodium distachyon plants (Berthet et al., 2011; Wang et al., 2015b; Le Bris et al., 2019). The laccase triple mutant (lac4 lac11 lac17) of *Arabidopsis* showed severe growth defects and lack of lignin in vascular tissues and fibers, but its Casparian strip structure was not affected, suggesting that laccases are essential for lignin polymerization and have non-redundant roles with peroxidases in lignification in vascular tissues (Zhao et al., 2013). Whether laccases can control lignin composition is currently unclear. Studies to date suggest that cell wall laccases are relatively promiscuous with respect to monolignol specificity in vitro, and the impact on lignin composition of their modified expression in planta cannot necessarily be predicted (He et al., 2019). Identification of laccases and/or peroxidases specifically involved in C-lignin polymerization can facilitate the introduction of C-lignin into non-seed-coat tissues of bioenergy crop plants as a co-product for bioprocessing (Ragauskas et al., 2014).

To this end, the present disclosure provides identification and characterization of a seed coat-specific laccase from *Cleome* (ChLAC8) discovered to be involved in C-lignin polymerization and polynucleotides ("ChLAC8 polynucleotides") encoding the laccase. The present disclosure also provides recombinant LAC polynucleotides encoding the ChLAC8 polypeptide and/or recombinant laccase (LAC) polypeptides capable of polymerizing caffeyl alcohol, as well as vectors, engineered cells, and transgenic plants including the recombinant LAC polynucleotides of the present disclosure and methods of using the recombinant LAC polynucleotides to increase production of C-lignin in plants.

Nucleic Acid and Protein Sequences

Isolated Nucleotide and cDNA Sequences

The present disclosure describes isolated nucleotide and cDNA sequences, which either in whole or in part, can encode a laccase (LAC) polypeptide/protein capable of polymerizing caffeyl alcohol to produce C-lignin. In some embodiments, the LAC polypeptides encoded by an isolated or synthetic LAC nucleotide or cDNA sequence or recombinant LAC polynucleotide sequence can result in an increase in C-lignin production by a transgenic plant or plant cell including the synthetic, cDNA or recombinant LAC polynucleotide sequence.

In some embodiments, a nucleotide encoding a LAC polypeptide can have an isolated nucleotide sequence according to or including any one of SEQ ID NOs: 1-2. In some embodiments, a cDNA corresponding to a LAC protein can have a sequence corresponding to SEQ ID NO: 2. The isolated nucleotide and/or cDNA can have or include a sequence with about 50, 51, 52, 53, 54, 55, 56, 57, 58, 59, 60, 61, 62, 63, 64, 65, 66, 67, 68, 69, 70, 71, 72, 73, 74, 5, 76, 77, 78, 79, 80, 81, 82, 83, 84, 85, 86, 87, 88, 89, 90, 91, 92, 93, 94, 95, 96, 97, 98, 99 to 100% identity to any one of SEQ ID NOs: 1-2. In some embodiments, a LAC polynucleotide/cDNA encodes a polypeptide having a sequence about 60, 61, 62, 63, 64, 65, 66, 67, 68, 69, 70, 71, 72, 73, 74, 5, 76, 77, 78, 79, 80, 81, 82, 83, 84, 85, 86, 87, 88, 89, 90, 91, 92, 93, 94, 95, 96, 97, 98, 99 to 100% identity to SEQ ID NO: 3. Suitable nucleotide sequences can be obtained by using standard methods known to those of skill in the art, including but not limited to, restriction enzyme digestion and polymerase chain reaction (PCR), or de novo nucleotide sequence synthesis techniques.

Recombinant Polynucleotide Sequences

The present disclosure also includes recombinant polynucleotide sequences having any of the isolated nucleotide or cDNA sequences or fragments thereof previously described and at least one additional heterologous polynucleotide sequence operatively linked to the isolated nucleotide or cDNA sequences or fragments thereof. In embodiments, the present disclosure includes a recombinant LAC polynucleotide that encodes a laccase (LAC) polypeptide capable of polymerizing caffeyl alcohol, where the recombinant polynucleotide includes a LAC polynucleotide having a sequence that is about 50-100% identical to LAC8 from *Cleome hassleriana* (ChLAC8), and at least one heterologous polynucleotide sequence operatively linked to the LAC polynucleotide. In embodiments the LAC polynucleotide is about 50-100% identical to ChLAC8 having SEQ ID NO: 1. In embodiments the LAC polynucleotide is more than 50% identical (e.g., 60-100% identical, 70-100% identical, 80-100% identical, 90-100% identical, etc.) to ChLAC8 of SEQ ID NO: 1. In embodiments, the LAC polynucleotide has the polynucleotide sequence of SEQ ID NO: 1 (gene sequence for ChLAC8) or SEQ ID NO: 2 (cDNA for ChLAC8). In embodiments, the LAC polynucleotide has a polynucleotide sequence that is 80-100% identical to SEQ ID NO: 2.

In embodiments of the recombinant polynucleotides of the present disclosure, the LAC polynucleotide encodes a polypeptide having 80-100% sequence identity to LAC8 from *Cleome hassleriana* (ChLAC8) having SEQ ID NO: 3. As described in greater detail in the Example below, it was discovered that ChLAC8 has an active site capable of binding with/interacting with caffeyl alcohol (as well as other substrates, such as sinapyl alcohol). It was found that certain active site residues were involved in substrate binding, including, but not limited to, amino acid residues Q289, E464, and H534 of ChLAC8. In particular, through sequence alignments, molecular modeling, and genetic analysis, the glutamine at residue 289 in the active site of ChLAC8 was found to stabilize the interaction with caffeyl alcohol when in the active site pocket. The stabilization appears to be due to interaction of the glutamine with a 3-hydroxyl group of caffeyl alcohol. Thus, in embodiments, the polynucleotide encoding a polypeptide having 80-100% sequence identity to ChLAC8 and having a glutamine residue in an active site position of the encoded polypeptide configured to be in substantial proximity to interact with a 3 hydroxyl group of a caffeyl alcohol bound in an active site of the polypeptide. In embodiments the recombinant polynucleotide encodes a polypeptide having 80-100% sequence identity to ChLAC8 and having a glutamine residue, Q289. In some embodiments, the LAC polynucleotide encodes a polypeptide having 80-100% sequence identity to ChLAC8 having SEQ ID NO: 3 and including amino acid residues Q289, E464, and H534.

As discussed above, in embodiments, the recombinant polynucleotides of the present disclosure include at least one heterologous polynucleotide sequence operatively linked to the LAC polynucleotide. In embodiments the heterologous polynucleotide sequence can be one or more sequences included to control/modulate the expression, stabilization, replication, and the like, of the coding and transcribed non-coding sequences of the recombinant polynucleotide. In some embodiments, heterologous polynucleotide sequences can include non-coding nucleotides that can be placed at the 5' and/or 3' end of the polynucleotides encoding a LAC protein without affecting the functional properties of the molecule. A polyadenylation region at the 3'-end of the coding region of a polynucleotide can be included. The polyadenylation region can be derived from the endogenous gene, from a variety of other plant genes, from T-DNA, or through chemical synthesis. In further embodiments, the nucleotides encoding the LAC protein may be conjugated to a nucleic acid encoding a signal or transit (or leader) sequence at the N-terminal end (for example) of the LAC protein that co-translationally or post-translationally directs transfer of the LAC protein. The polynucleotide sequence may also be altered so that the encoded root LAC protein is conjugated to a linker, selectable marker, or other sequence for ease of synthesis, purification, and/or identification of the protein. In embodiments, the heterologous polynucleotide sequence comprises a regulatory polynucleotide sequence (e.g., promoter and/or other transcription control elements), a selectable marker polynucleotide, or combinations of these. In embodiments, the at least one heterologous polynucleotide sequence is a promoter, such as an activatable promoter, a constitutive promoter, etc.

To express an exogenous LAC protein gene, fragment thereof, or antisense nucleotide in a cell, in embodiments, the exogenous nucleotide can be combined (e.g., in a vector) with transcriptional and/or translational initiation regulatory sequences, including but not limited to, promoters and/or other transcriptional/translational control elements, that direct the transcription of the gene and/or translation of the encoded protein in a cell. In some embodiments, a constitutive promoter may be employed. Suitable constitutive promoters for plant cells include, but are not limited to, the cauliflower mosaic virus (CaMV) 35S transcription initiation region, the 1'- or 2'-promoter derived from T-DNA of *Agrobacterium tumefaciens*, the ACT11 and Cat3 promoters from *Arabidopsis* (Huang et al. Plant Mol. Biol. 1996, 33:125-139 and Zhong et al. Mol. Gen. Genet. 1996, 251: 196-203), the stearoyl-acyl carrier protein desaturase gene promoter from *Brassica napus* (Solocombe et al. Plant Physiol. 1994, 104:1167-1176), and the GPc1 and Gpc2 promoters from maize (Martinez et al. J. Mol. Biol. 1989, 208:551-565 and Manjunath et al. Plant Mol. Biol. 1997, 33:97-112). Suitable constitutive promoters for bacterial cells, yeast cells, fungal cells are generally known in the art, such as a T-7 promoter for bacterial expression and an alcohol dehydrogenase promoter for expression in yeast.

In other embodiments, tissue-specific promoters or inducible promoters may be employed to direct expression of the exogenous nucleic acid in a specific cell type, under certain environmental conditions, and/or during a specific state of development. In some embodiments, the tissue-specific promoter can be a root-specific or a phloem-specific promoter. Suitable root specific and phloem-specific promoters are generally known in the art. Examples of environmental conditions that may affect transcription by inducible promoters include anaerobic conditions, elevated temperature, the presence of light, contact with chemicals or hormones, or infection by a pathogen. Suitable plant inducible promoters include the root-specific ANRI promoter (Zhang and Forde. Science. 1998, 279:407), the photosynthetic organ-specific RBCS promoter (Khoudi et al. Gene. 1997, 197:343), the tomato fruit ripening-specific E8 promoter (Deikman, J., et al. Plant Physiol. 1992, 100: 2013-2017), the salicylic acid-inducible PR1 promoter (Lebel et al. Plant Journal. 1998, 16:223-233), and the phloem specific SUC2 promoter.

A selectable marker can also be included in the recombinant nucleic acid to confer a selectable phenotype on plant cells. For example, the selectable marker may encode a protein that confers biocide resistance, antibiotic resistance (e.g., resistance to kanamycin, G418, bleomycin, hygromycin, etc.), or herbicide resistance (e.g., resistance to chlorosulfuron or Basta, etc.). Thus, the presence of the selectable phenotype can indicate the successful transformation of the host cell. An exemplary selectable marker includes the beta-glucuronidase (GUS) reporter gene.

Suitable recombinant polynucleotides can be obtained by using standard methods known to those of skill in the art, including but not limited to, restriction enzyme digestion, PCR, ligation, and cloning techniques In embodiments, the recombinant polynucleotide encodes a LAC polypeptide capable of polymerizing caffeyl alcohol, where the recombinant polynucleotide is a LAC polynucleotide having a sequence about 50-100% identical (e.g., 60-100% identical, 70-100% identical, 80-100% identical, 90-100% identical, etc.) to the cDNA for ChLAC8 (SEQ ID NO: 2). In such embodiments, the recombinant polynucleotide may or may not include at least one heterologous polynucleotide sequence operatively linked to the LAC polynucleotide.

Isolated Protein (Polypeptide) and Peptide Sequences

The present disclosure also describes an isolated or synthetic protein (polypeptide) corresponding to a LAC protein/polypeptide capable of polymerizing caffeyl alcohol to produce C-lignin. In some embodiments, the isolated polypeptide has an amino acid sequence corresponding to SEQ ID NO: 3 (the peptides sequence for ChLAC8). In some embodiments, a LAC protein has a sequence at least 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 to 100% identity to SEQ ID NO: 3.

Modifications and changes can be made in the structure of the polypeptides of the present disclosure that result in a molecule having similar characteristics as the unmodified polypeptide (e.g., a conservative amino acid substitution). Modification techniques are generally known in the art. For example, certain amino acids can be substituted for other amino acids in a sequence without appreciable loss of activity. Because it is the interactive capacity and nature of a polypeptide that defines that polypeptide's biological functional activity, certain amino acid sequence substitutions can be made in a polypeptide sequence and nevertheless obtain a functional variant. Polypeptides with amino acid sequence substitutes that still retain properties substantially similar to or better than polypeptides corresponding to a ChLAC8 protein are within the scope of this disclosure. In some embodiments, the LAC protein of the present disclosure can have enhanced activity as compared to CHLAC8 wild-type.

The present disclosure also includes isolated and synthetic peptides corresponding to a fragment of the polypeptide corresponding to a LAC protein of the present disclosure. In some embodiments the peptides correspond to a portion of SEQ ID NO: 3. In embodiments, the isolated or synthetic peptides of the present disclosure have about 80, 81, 82, 83, 84, 85, 86, 87, 88, 89, 90, 91, 92, 93, 94, 95, 96, 97, 98, 99 to 100% identity to a portion of SEQ ID NO: 3 that are at least 10 amino acids long.

In other embodiments, the isolated or synthetic peptide as described herein is suitable for use in production of antibodies against a LAC protein. In other words, the isolated or synthetic peptide as described herein serves as the antigen to which an antibody is raised against. In some embodiments, the isolated or synthetic peptide sequence is also the epitope of the antibody. Antibodies raised against a LAC protein of the present disclosure are suitable for use in methods for at least detection, quantification, and purification of a LAC protein. Other uses for anti-LAC protein antibodies are generally known in the art.

Vectors

Vectors having one or more of the polynucleotides or antisense polynucleotides described herein can be useful in producing transgenic bacterial, fungal, yeast, plant cells, and transgenic plants that express varying levels of a LAC polypeptide capable of polymerizing caffeyl alcohol. Within the scope of this disclosure are vectors containing one or more of the polynucleotide sequences described herein. Some embodiments of the present disclosure include vectors including the recombinant polynucleotide of the present disclosure described above.

In embodiments, the vector has at least one regulatory sequence such as described above operatively linked to a DNA molecule or encoding a LAC protein such that the LAC protein is expressed in a bacteria, fungus, yeast, plant, or other cell into which it is transformed.

In other embodiments, the vector includes a promoter that serves to initiate expression of the LAC protein such that the LAC protein is over-expressed in a plant cell into which it is transformed relative to a wild-type bacteria, fungus, yeast, or plant cell. In some embodiments, the vector has at least one regulatory sequence operatively linked to a DNA molecule encoding a LAC protein and a selectable marker. The vector may include other sequences, such as those related to the uptake of the vector, expression of the vector, and/or identification of cells harboring the vector.

Other embodiments of the present disclosure include a vector having an antisense polynucleotide capable of inhibiting expression of an endogenous gene encoding a LAC protein and at least one regulatory sequence operatively linked to the antisense polynucleotide such that the antisense polynucleotide is transcribed in a type bacteria, fungus, yeast, or plant cell into which it is transfected. In embodiments, the antisense polynucleotides may be capable of inhibiting expression of an endogenous LAC gene corresponding to or including any one of SEQ ID NOs: 1-2 or about 50, 51, 52, 53, 54, 55, 56, 57, 58, 59, 60, 61, 62, 63, 64, 65, 66, 67, 68, 69, 70, 71, 72, 73, 74, 5, 76, 77, 78, 79, 80, 81, 82, 83, 84, 85, 86, 87, 88, 89, 90, 91, 92, 93, 94, 95, 96, 97, 98, 99 to 100% identity to any one of SEQ ID NOs: 1-2.

Transgenic Cells, Organisms, and Plants

The polynucleotide sequences and vectors described above can be used to transform cells (e.g., plant cell) and to produce transgenic plants. The present disclosure provides transformed cells including the recombinant polynucleotides of the present disclosure described above including a LAC polynucleotide having a sequence that is about 50-100% identical to any one of SEQ ID NOs: 1-2, and at least one heterologous polynucleotide sequence operatively linked to the LAC polynucleotide. In embodiments the transformed plant cell can include a recombinant LAC polynucleotide stably integrated into its genome (along with any regulatory factors), or the recombinant LAC polynucleotide can be housed on a vector of the present disclosure that is present in the cell(s).

In embodiments the heterologous polynucleotide sequence includes a regulatory polynucleotide sequence, a selectable marker polynucleotide, or both. In embodiments the cell can be a plant cell, bacterial cell, yeast cell, of fungus cell. Also, within the scope of this disclosure are populations of cells where about 1% to about 100%, or between about 50% and about 75%, or between about 75% and about 100% of the cells within the population contain a vector as previously described. In some embodiments, the cell is a plant cell, such as, but not limited to: Arabidopsis, switchgrass, poplar, miscanthus, corn, rice, wheat, barley, cotton, maize, soybean, canola and other biomass plants.

In some embodiments, one or more cells within the population contain more than one type of vector. In some embodiments, all (about 100%) the cells that contain a vector have the same type of vector. In other embodiments, not all the cells that contain a vector have the same type of vector or plurality of vectors. In some embodiments, about 1% to about 100%, or between about 50% and about 75%, or between about 75% and about 100% of the cells within the population contain the same vector or plurality of vectors. In some cell populations, all the cells are from the same species. Other cell populations contain cells from different species. Transfection methods for establishing transformed (transgenic) cells are well known in the art In addition, the present disclosure provides transgenic organisms produced/grown from the transformed cells of the present disclosure. The present disclosure includes transgenic plants having a plurality of cells where one or more cells of the plurality of cells contain any of the recombinant polynucleotides or vectors previously described that have DNA sequences encoding a LAC protein of the present disclosure capable of polymerizing caffeyl alcohol. In one embodiment, the recombinant polynucleotide contains at least one regulatory element operatively linked to a LAC polynucleotide sequence having about 50, 51, 52, 53, 54, 55, 56, 57, 58, 59, 60, 61, 62, 63, 64, 65, 66, 67, 68, 69, 70, 71, 72, 73, 74, 5, 76, 77, 78, 79, 80, 81, 82, 83, 84, 85, 86, 87, 88, 89, 90, 91, 92, 93, 94, 95, 96, 97, 98, 99 to 100% identity to any one of SEQ ID NOs: 1-2.

Also described herein are transgenic plants having one or more cells transformed with vectors containing any of the nucleotide sequences described above, and/or fragments of the nucleic acids encoding the LAC protein(s) of the present disclosure. In some embodiments, the vector contains a LAC polynucleotide having about 50, 51, 52, 53, 54, 55, 56, 57, 58, 59, 60, 61, 62, 63, 64, 65, 66, 67, 68, 69, 70, 71, 72, 73, 74, 5, 76, 77, 78, 79, 80, 81, 82, 83, 84, 85, 86, 87, 88, 89, 90, 91, 92, 93, 94, 95, 96, 97, 98, 99 to 100% identity to any one of SEQ ID NOs: 1-2. The transgenic plant can be made from any suitable plant species or variety including, but not limited to Arabidopsis, switchgrass, poplar, eucalyptus, miscanthus, corn, rice, wheat, barley, cotton, maize, soybean, canola and other biomass plants.

In some embodiments, the transgenic plant having a nucleotide sequence encoding a LAC polypeptide capable of polymerizing caffeyl alcohol has increased expression of the LAC protein relative to a wild type plant/non-transgenic control. In other embodiments, the transgenic plant having a nucleotide sequence encoding a LAC protein of the present disclosure has increased expression of a LAC protein relative to a wild type plant and produces a LAC protein. The transgenic plant can have de novo and/or increased production of C-lignin. In embodiments, transgenic plant of the present disclosure expresses an increased amount of a laccase (LAC) polypeptide capable of polymerizing caffeyl alcohol as compared to a corresponding non-transgenic control plant. In embodiments, the transgenic plant produces caffeyl alcohol. In some embodiments, the transgenic plant has increased production of C-lignin as compared to a corresponding non-transgenic control.

The transgenic plants can also have recombinant polynucleotides encoding for polypeptides/proteins involved in regulation and/or production of caffeyl alcohol and/or its precursors. In some embodiments including such polynucleotides encoding for proteins involved in regulation and/or production of caffeyl alcohol and/or its precursors, the plants produce a greater amount of caffeyl alcohol than a wild type plant, thereby providing substrates for the LAC protein for production of C-lignin from the caffeyl alcohol monomers.

A transformed plant cell of the present disclosure can be produced by introducing into a plant cell one or more vectors as previously described. In one embodiment, transgenic plants of the present disclosure can be grown from a transgenic plant cell transformed with one or more of the vectors previously described.

Techniques for transforming a wide variety of plant cells with vectors or naked nucleic acids are well known in the art and described in the technical and scientific literature. See, for example, Weising et al. Ann. Rev. Genet. 1988, 22:421-477. For example, the vector or naked nucleic acid may be introduced directly into the genomic DNA of a plant cell using techniques such as, but not limited to, electroporation and microinjection of plant cell protoplasts, or the recombinant nucleic acid can be introduced directly to plant tissue using ballistic methods, such as DNA particle bombardment.

Microinjection techniques are known in the art and well described in the scientific and patent literature. The introduction of a recombinant nucleic acid using polyethylene glycol precipitation is described in Paszkowski et al. EMBO J. 1984, 3:2717-2722. Electroporation techniques are described in Fromm et al. Proc. Natl. Acad. Sci. USA. 1985, 82:5824. Ballistic transformation techniques are described in Klein et al. Nature. 1987, 327:70-73. The recombinant nucleic acid may also be combined with suitable T-DNA flanking regions and introduced into a conventional *Agrobacterium tumefaciens* host vector, or other suitable vector. The virulence functions of the *Agrobacterium tumefaciens* host will direct the insertion of the recombinant nucleic acid including the exogenous nucleic acid and adjacent marker into the plant cell DNA when the cell is infected by the bacteria. *Agrobacterium tumefaciens*-mediated transformation techniques, including disarming and use of binary vectors, are known to those of skill in the art and are well described in the scientific literature. See, for example, Horsch et al. Science. 1984, 233:496-498; Fraley et al. Proc. Natl. Acad. Sci. USA. 1983, 80:4803; and Gene Transfer to Plants, Potrykus, ed., Springer-Verlag, Berlin, 1995.

A further method for introduction of the vector or recombinant nucleic acid of the present disclosure into a plant cell is by transformation of plant cell protoplasts (stable or transient). Plant protoplasts are enclosed only by a plasma membrane and will therefore more readily take up macromolecules like exogenous DNA. These engineered protoplasts can be capable of regenerating whole plants. Suitable methods for introducing exogenous DNA into plant cell protoplasts include electroporation and polyethylene glycol (PEG) transformation. Following electroporation, transformed cells are identified by growth on appropriate medium containing a selective agent.

The presence and copy number of the exogenous nucleic acid in a transgenic plant can be determined using methods well known in the art, e.g., Southern blotting analysis. Expression of an exogenous LAC protein (e.g. ChLAC8) in a transgenic plant may be confirmed by detecting an increase or decrease of mRNA or the LAC protein in the transgenic plant. Methods for detecting and quantifying mRNA or proteins are well known in the art.

Transformed plant cells that are derived by any of the above transformation techniques, or other techniques now known or later developed, can be cultured to regenerate a whole plant. In embodiments, such regeneration techniques may rely on manipulation of certain phytohormones in a tissue culture growth medium, typically relying on a biocide or herbicide selectable marker that has been introduced together with the exogenous nucleic acid. Plant regeneration from cultured protoplasts is described in Evans et al., Protoplasts Isolation and Culture, Handbook of Plant Cell Culture, pp. 124-176, MacMillilan Publishing Company, New York, 1983; and Binding, Regeneration of Plants, Plant Protoplasts, pp. 21-73, CRC Press, Boca Raton, 1985. Regeneration can also be obtained from plant callus, explants, organs, or parts thereof. Such regeneration techniques are described generally in Klee et al. Ann. Rev. Plant Phys. 1987, 38:467-486.

Once the exogenous a LAC polynucleotide has been confirmed to be stably incorporated in the genome of a transgenic plant, it can be introduced into other plants by sexual crossing. Any of a number of standard breeding techniques can be used, depending upon the species to be crossed.

Methods of Increasing Production of C-Lignin in a Plant

This disclosure also encompasses methods of increasing production of C-lignin in a plant. In embodiments, the production of C-lignin in a plant is increased by increasing the production of a laccase enzyme in a plant capable of polymerizing caffeyl alcohol. In embodiments, methods of increasing production of C-lignin in a plant include integrating into the genome of at least one cell of a plant: a recombinant polynucleotide of the present disclosure including a LAC polynucleotide encoding a LAC polypeptide capable of polymerizing caffeyl alcohol (e.g., integrated into the genome of the plant cell, housed on a vector in the plant cell, etc.), such that the recombinant polynucleotide is expressed in the plant cell.

The method further includes growing said plant in the presence of caffeyl alcohol, wherein the recombinant polynucleotide is overexpressed in the plant relative to a wild-type plant, such that the plant produces C-lignin. Since the production of C-lignin is dependent on the presence of monomers of C-lignin (e.g., caffeyl alcohol) or precursors of such monomers, in embodiments, methods of the present disclosure also include ensuring a supply of caffeyl alcohol. In embodiments, the caffeyl alcohol, or one or more of its precursors, can be externally provided (such as in plant feed, culture media, fertilizer, etc.). In other embodiments, the caffeyl alcohol is synthesized by the plant, e.g., via native pathways or by inclusion of exogenous polynucleotides encoding peptides that provide and/or synthesize caffeyl alcohol and/or precursors of caffeyl alcohol.

In embodiments of methods of the present disclosure, the plant produces a greater amount of C-lignin than a corresponding wild-type plant. In some embodiments, the cell is a plant cell, such as, but not limited to *Arabidopsis*, switchgrass, poplar, *eucalyptus, miscanthus*, corn, rice, wheat, barley, cotton, maize, soybean, canola and other biomass plants Additional details regarding the methods and compositions, of the present disclosure are provided in the Examples below. The specific examples below are to be construed as merely illustrative, and not limitative of the remainder of the disclosure in any way whatsoever. Without further elaboration, it is believed that one skilled in the art can, based on the description herein, utilize the present disclosure to its fullest extent.

It should be emphasized that the embodiments of the present disclosure, particularly, any "preferred" embodiments, are merely possible examples of the implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure and protected by the following claims.

The following examples are put forth so as to provide those of ordinary skill in the art with a complete disclosure and description of how to perform the methods and use the compositions and compounds disclosed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° ° C. and 1 atmosphere.

Sequences

The following sequences are referred to in the present disclosure and claims:

The nucleotide sequence for ChLac8

SEQ ID NO: 1

AAAATTGATTTATTTTATGCGATCGGTATAATATTTTTTTTTAAAAAAAAACAAATTATAAAAGAAGATT

CACCATAACATTTCATTACCTTCCTCCAAGGCATCGTCTCCAAGCCCGAATATGGCCAGTTTTGAGTGCT

TTCTCATCTGCTTTGTTCTTATCCTCCTCCCTTCTTCTTCGTCGAAGGCTTATGCATCTGTCGTCGAACA

CACTTTCCTTGTATTACTCTCCCACAATATTTTAATTTTAATTTCCAGTCTTTTTAACGTATGGAAAAAC

TGTAAACTGACGGCGTTAGTCGCTCCTGCAGGTCCAAAACTTCACGGCGAAACCGTTGTGCAAAGAGCAG

GTGATACCGACAGTTAACGGAAGTCTTCCGGGTCCGACGGTAAACGTCAGAGAGGGAGACACACTTATTG

TTCATGTCGTTAACAACTCCCCTTTTAACGTCACCATTCACTGGTAAATCCATTCATCACATACGATTAT

AGGGTCGTTTATAGTTATTAGCATGAATAAGGAGTTACTAAGAATCTGTGATTATGCTATTAATTAGTCT

TGTTTTTCCACGTTTCTTGATTCTATATAGGCATGGAGTGTTTCAGTTGATGAGTGCGTGGATGGATGGA

ACAGATATGATAACACAATATCCGATCCGACCGGAAGATAGGTTCACTTATAAGTTTAACGTCACAGGAC

AAGAAGGTACGCTGCACTGGCACGCACATGTCGTTAACCTACGCGCCACCCTGCACGGTGCTCTTGTCAT

CCGTCCTCGAGCTGGTCGGCCTTATCCTTTTCCCGAACCCTATGAAGAAGCTCTCATCATTCTCGGTCGG

CATATATACATACATATACATATGTATATATACATATAATATTTTCATACCCAATGAATCGTATATGAAA

ATCCATATATTGATTCGGGAAAACTTTTCGAATCGATGCAGAACAATGGTGGAACACCGATATCGAAAAT

CTCCAACTAAGGCCCGCTCCTCTTTCAGATGCCTACCTCATCAACGGATTAGCAGGAGATTCATTCGATT

GCTCGCGGAATAGTGAGTGAAAATAAAAACATATATAAGTCTCATCCGATTCACAAATTCATATATTCAA

AGCTTCTTTTTTTTTTTTTGCATCTAGAAATGTTTAAACTAGAGGTGGTACAAGGAAAACGGTACTTGCT

AAGGATCATAAACGCAGCACTTAACTCACATCTATTCTTCAAGATAGCGAACCATTCCTTGCGAGTCGTG

GCCTTAGACGCCGTCTACACGAATCCTTACGTTACCGACATCGTTGTCCTAACGCCAGGACAGACCGTAG

ACGCACTTCTCCATGCAGACCAAACCCTAGGCTCATACTACATGACCACTCAGCTTTACGTCAGCGCCAC

AGGCCAGCCATTCCCCGACAAAACCCTAGCCAATGCTCTCGTTGTCTACCAAGGTGCCACGTCATCGTCC

CGCGCCATGCCATCGTTGCCCGACGTGACGGATACGCAGACAGCGTATAGATTCTCCTCGAGTATCACCG

GCCTTGTCAGTGGGCCCCATTGGAGGCCGGTGCCTCGCAACGTGGACGAGAGGATGTTTATGACCATGGG

GTTAGGTCTTGAGCAATGTCCACCGAGCATGCAGTGTCCCGGACTGTACGGACAACAATTCGCAGGCTCG

CTGAACAACCGCTCGTTCGAAAATCCCAAGACATTTCCCATGCAAGAGGCTTATTTCTACAACATATCCG

GAGTGTACTCCGACGATTTTCCCAATCAACCGCCGATAAAATTCGATTACACGAATTTTAACGTTAGTAC

GGATTACGAGTACCGGATGTTGTTTCCCGAGAGATTAACGAGCGCGAAGATCTTAAAATTCAATTCGACG

GTCGAGATCGTTCTGCAAAACACGGCGATGATCACAGCGGAAAGTCACCCGATGCACCTTCACGGGTTCA

ATTTCCATGTGTTGGGTCAAGGGTTCGGCAACTATGAACCGAGCCGAGACGTGGGAAAGCTGAACTTGGT

TAACCCGCAGATGCGTAACACCATCGGTGTGCCGCCCGGTGGATGGGTTGTCCTCAGATTCGTGGCCAAT

AACCCGGGTTAGAGATTTAACATATGATTCTAGTTTCTATCAAATATATTATTAATTAAGAAAATATCAA

TTAAAATACACAATTTTCCCGCATAATTATGCTAACTATTTCAAACTTTCAGATAAATGATTAAACGTTC

AAATTGTTACTTGATTTCTGTCTCGAAATAGTACATTTTCAAAATATAGACCAACCATTATTTCCTTCTC

GATCGCTGTGGTTTGGTGGTAGTGTAATATCTTGAGAATTCATATATTTGTTATATGAAATTTTTTTAAT

TGTTAGCGATTCAACATATGATTCTAGTTTCTATCAAATATATTAATTAAGAAAAAATCTATACATAAAA

TATACATTTTTTTAAAAAAAAATATATCATTTTTTTTCAAAACATTCAAAATGTAGACCAACCGTTGTTT

AACCCCATTATTTTATTCTCACCGGCTTCTAAATGATGTTATTGTTCTAATAAAAATTCGGTAATATTTT

-continued

GAGAGTTCACATATTTATTTATATGAAAAATTTAATTACATAGATACCTATATTAAAACTAGTTTATATA

CTTAATTAGGATTTTTTTTAACAACTTATGTCATACTTACTAAGTTTTGTTTTGTTAATTAGTTAGAAAA

GTTGTGAAATATGAGAACTAATCTTTGATATATACGAACCGTGTAGGTGTGTGGATGTTCCATTGTCACA

TGGATGCACATTTGCCGTACGGAATAATTATGGCTTTCATCGTCCAAAACGGACCACATCCGGCGACCAG

CTTGCCGCCGCCGCCGTTGGATCATCTCGAATGTTGTCGGGACGCCGAAATCTATAACCATCCTACGTAC

GACCAATATTAATTCCTCCTCCTAGATAGAAAGAGCAGATAAAAAAATAACATTTGTGAATATTCTCCTT

CCCCTAACACCTGTGATTCAACCGGTTCTCTGGAAGGTTTTAATGCTGCAGTTAGGGTTGGGAAGCTTCT

ATCGGTTATTAAATTGTCTCTATGGGTTGAAGACCATTGCAGATTGGTTTGGTTTCTGCAATCTATCGAA

CCTCATCGACTGTGA

The cDNA sequence for ChLac8

SEQ ID NO: 2

ATGGCCAGTTTTGAGTGCTTTCTCATCTGCTTTGTTCTTATCCTCCTCCCTTCTTCTTCGTCGAAGGCTT

ATGCATCTGTCGTCGAACACACTTTCCTTGTCCAAAACTTCACGGCGAAACCGTTGTGCAAAGAGCAGGT

GATACCGACAGTTAACGGAAGTCTTCCGGGTCCGACGGTAAACGTCAGAGAGGGAGACACACTTATTGTT

CATGTCGTTAACAACTCCCCTTTTAACGTCACCATTCACTGGCATGGAGTGTTTCAGTTGATGAGTGCGT

GGATGGATGGAACAGATATGATAACACAATATCCGATCCGACCGGAAGATAGGTTCACTTATAAGTTTAA

CGTCACAGGACAAGAAGGTACGCTGCACTGGCACGCACATGTCGTTAACCTACGCGCCACCCTGCACGGT

GCTCTTGTCATCCGTCCTCGAGCTGGTCGGCCTTATCCTTTTCCCGAACCCTATGAAGAAGCTCTCATCA

TTCTCGAACAATGGTGGAACACCGATATCGAAAATCTCCAACTAAGGCCCGCTCCTCTTTCAGATGCCTA

CCTCATCAACGGATTAGCAGGAGATTCATTCGATTGCTCGCGGAATAAAATGTTTAAACTAGAGGTGGTA

CAAGGAAAACGGTACTTGCTAAGGATCATAAACGCAGCACTTAACTCACATCTATTCTTCAAGATAGCGA

ACCATTCCTTGCGAGTCGTGGCCTTAGACGCCGTCTACACGAATCCTTACGTTACCGACATCGTTGTCCT

AACGCCAGGACAGACCGTAGACGCACTTCTCCATGCAGACCAAACCCTAGGCTCATACTACATGACCACT

CAGCTTTACGTCAGCGCCACAGGCCAGCCATTCCCCGACAAAACCCTAGCCAATGCTCTCGTTGTCTACC

AAGGTGCCACGTCATCGTCCCGCGCCATGCCATCGTTGCCCGACGTGACGGATACGCAGACAGCGTATAG

ATTCTCCTCGAGTATCACCGGCCTTGTCAGTGGGCCCCATTGGAGGCCGGTGCCTCGCAACGTGGACGAG

AGGATGTTTATGACCATGGGGTTAGGTCTTGAGCAATGTCCACCGAGCATGCAGTGTCCCGGACTGTACG

GACAACAATTCGCAGGCTCGCTGAACAACCGCTCGTTCGAAAATCCCAAGACATTTCCCATGCAAGAGGC

TTATTTCTACAACATATCCGGAGTGTACTCCGACGATTTTCCCAATCAACCGCCGATAAAATTCGATTAC

ACGAATTTTAACGTTAGTACGGATTACGAGTACCGGATGTTGTTTCCCGAGAGATTAACGAGCGCGAAGA

TCTTAAAATTCAATTCGACGGTCGAGATCGTTCTGCAAAACACGGCGATGATCACAGCGGAAAGTCACCC

GATGCACCTTCACGGGTTCAATTTCCATGTGTTGGGTCAAGGGTTCGGCAACTATGAACCGAGCCGAGAC

GTGGGAAAGCTGAACTTGGTTAACCCGCAGATGCGTAACACCATCGGTGTGCCGCCCGGTGGATGGGTTG

TCCTCAGATTCGTGGCCAATAACCCGGGTGTGTGGATGTTCCATTGTCACATGGATGCACATTTGCCGTA

CGGAATAATTATGGCTTTCATCGTCCAAAACGGACCACATCCGGCGACCAGCTTGCCGCCGCCGCCGTTG

GATCATCTCGAATGTTGTCGGGACGCCGAAATCTATAACCATCCTACGTACGACCAATATTAA

The peptide sequence for ChLAC8

SEQ ID NO: 3

MASFECFLICFVLILLPSSSSKAYASVVEHTFLVQNFTAKPLCKEQVIPTVNGSLPGPTVNVREGDTLIV

HVVNNSPFNVTIHWHGVFQLMSAWMDGTDMITQYPIRPEDRFTYKFNVTGQEGTLHWHAHVVNLRATLHG

ALVIRPRAGRPYPFPEPYEEALIILEQWWNTDIENLQLRPAPLSDAYLINGLAGDSFDCSRNKMFKLEVV

QGKRYLLRIINAALNSHLFFKIANHSLRVVALDAVYTNPYVTDIVVLTPGQTVDALLHADQTLGSYYMTT

-continued

QLYVSATGQPFPDKTLANALVVYQGATSSSRAMPSLPDVTDTQTAYRFSSSITGLVSGPHWRPVPRNVDE

RMFMTMGLGLEQCPPSMQCPGLYGQQFAGSLNNRSFENPKTFPMQEAYFYNISGVYSDDFPNQPPIKFDY

TNFNVSTDYEYRMLFPERLTSAKILKFNSTVEIVLQNTAMITAESHPMHLHGFNFHVLGQGFGNYEPSRD

VGKLNLVNPQMRNTIGVPPGGWVVLRFVANNPGVWMFHCHMDAHLPYGIIMAFIVQNGPHPATSLPPPPL

DHLECCRDAEIYNHPTYDQY

Note:
Exons are bold underlined.

EXAMPLES

Now having described the embodiments of the disclosure, in general, the examples describe some additional embodiments. While embodiments of the present disclosure are described in connection with the example and the corresponding text and figures, there is no intent to limit embodiments of the disclosure to these descriptions. On the contrary, the intent is to cover all alternatives, modifications, and equivalents included within the spirit and scope of embodiments of the present disclosure.

Example 1-Characterization of ChLAC 8 and Role in Polymerization of Caffeyl Alcohol for C-Lignin Biosynthesis The properties of C-lignin make it a natural source of carbon fibers and high-value chemicals, but the mechanism of in planta polymerization of caffeyl alcohol to form C-lignin remains unclear. In the ornamental plant *Cleome hassleriana*, lignin biosynthesis in the seed coat switches from guaiacyl (G) lignin to C-lignin at ~12 days after pollination. It was found that the transcript profile of the laccase gene ChLAC8 parallels the accumulation of C-lignin during seed coat development. Recombinant ChLAC8 oxidizes caffeyl and sinapyl alcohols, generating their corresponding dimers or trimers in vitro, but cannot oxidize coniferyl alcohol. The present example explores a basis for this substrate preference based on molecular modeling/docking experiments. Suppression of ChLAC8 expression led to significantly reduced C-lignin content in the seed coats of transgenic *Cleome* plants. Feeding of $^{13}$C-caffeyl alcohol to the *Arabidopsis thaliana* caffeic acid O-methyl-transferase (comt) mutant resulted in no incorporation of $^{13}$C into C-lignin, but expressing ChLAC8 in this genetic background led to appearance of C-lignin with over 40% label incorporation. The appearance of C-lignin upon expression of ChLAC8 in comt mutants of *Medicago truncatula* and *Arabidopsis* indicates that this enzyme can facilitate caffeyl alcohol polymerization in planta, making ChLAC8 an important component of a gene toolkit for engineering C-lignin.

Materials and Methods

Plant Materials and Chemicals
*Cleome* (*Cleome hassleriana*) plants were grown in a greenhouse in Metro-Mix 830/Fafard 3B soil (Sun Gro Horticulture) at 25-28° C. with a 16 h/8 h day/night cycle of 150 µmol m$^{-2}$ sec$^{-1}$ light intensity using high pressure sodium (red spectrum) and metal halide (blue spectrum) lamps as supplemental lighting if needed. Flowers were hand-pollinated and seeds harvested periodically at 8 to 20 DAP at 2-day intervals. To prepare seed coats, fresh seeds were cut into two pieces with a surgical knife to remove the embryo. Seed coats and stem samples (bark, fiber, pith) were frozen immediately in liquid nitrogen and stored at −80° C. Each experiment was performed with three biological replicates (separate experiments), and samples from at least five plants were pooled for each replicate.

Seeds of the *Arabidopsis* comt mutant (Salk_135290) were obtained from the ABRC at Ohio State University. T-DNA was inserted in the third exon of the COMT gene At5g54160. The phenotype of this comt mutant line was described by Nakatsubo et al. (2008). Seeds were sown in Sunshine #1/Fafard-1P soil (Sun Gro Horticulture) and vernalized at 4° C. for 3 days in the dark before moving to a growth chamber set at 22° C. with a 16 h/8 h day/night cycle of 150 µmol m$^{-2}$ sec$^{-1}$ light intensity using both T8 fluorescent and halogen incandescent full spectrum lamps. Primers used for genotyping are listed in Wang, X., et al., (2020), which is hereby incorporated by reference herein in its entirety (see, Wang, X., et al., (2020), Supplemental Materials hereinafter "Wang Supp.", Table 4). After selecting homozygous T-DNA insertion mutants, plants were used for transformation. Coniferyl alcohol and sinapyl alcohol were purchased from Sigma-Aldrich. Unlabeled caffeyl alcohol was a gift from Drs. Rui Katahira and Gregg Beckham, National Renewable Energy Laboratory, Golden, CO, USA.

Figure 6F:
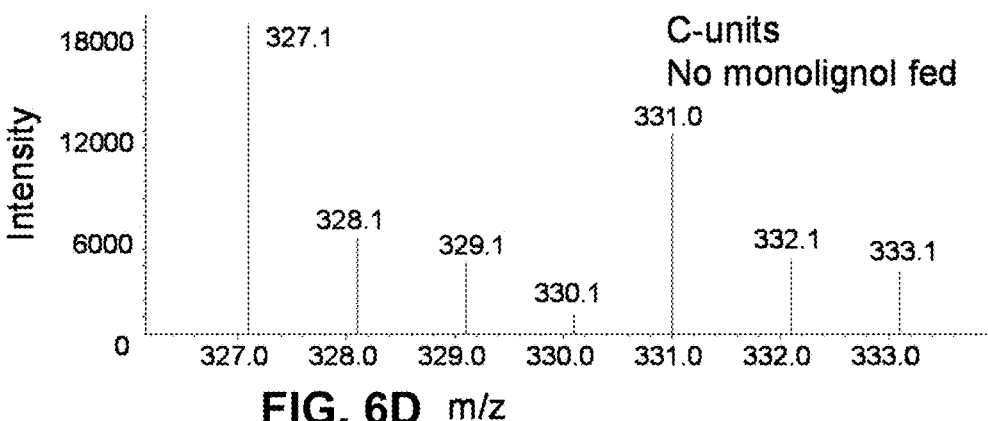

Synthesis of $^{13}$C-Labeled Caffeyl Alcohol
$^{13}$C-caffeyl alcohol was synthesized in three steps with 66% overall yield (FIGS. 6A-6D). First, $^{13}$C$_6$-Caffeic acid was synthesized following a modification of the procedure described by Teixeira et al. (2013), incorporated herein by reference (FIG. 6A). $^{13}$C$_6$-3,4-Dihydroxy-benzaldehyde (75.0 mg, 0.52 mmol) and malonic acid (119.2 mg, 1.15 mmol) were dissolved in pyridine (3 mL) and piperidine (30 µL) added as a catalyst. The reaction took place at 68° C. for 24 h. The mixtures were diluted with ethyl acetate (5 mL) and washed with 1 M HCl (3 mL) and water (3×5 mL). The organic layers were then dried over Na$_2$SO$_4$, filtered, and concentrated under reduced pressure. The residue was purified by flash chromatography (silica gel; n-hexane:ethyl acetate:methanol (2:1:0.1) to obtain 62.8 mg (65% yield) of $^{13}$C$_6$-caffeic acid.

$^{13}$C$_6$-Caffeic acid methyl ester was then synthesized by Fisher esterification according to Teixeira et al. (2013) (FIG. 6A). $^{13}$C$_6$-Caffeic acid (60 mg, 0.32 mmol) was dissolved in methanol (4 mL) and 74 µL of H2SO$_4$ was added. The reaction mixture was stirred at 70° C. for 24 h. After cooling to room temperature, the solvent was removed in vacuo, and the residue dissolved in ethyl acetate (10 mL) and washed with NaHCO$_3$ and water (3×5 mL). The organic layer was dried over Na$_2$SO$_4$, filtered, and concentrated under reduced pressure. The residue was purified by flash chromatography (silica gel; n-hexane:ethyl acetate:methanol (3:1:0.01) to obtain 48.2 mg (75% yield) of $^{13}$C$_6$-caffeic acid methyl ester.

$^{13}$C$_6$-Caffeyl alcohol was synthesized following a variation of a process described by Min-Kim et al. (2012)

(incorporated herein by reference) (FIG. 6A). $^{13}C_6$-caffeic acid methyl ester (48.0 mg, 0.24 mmol) was dissolved in 6 mL of tetrahydrofuran under argon, cooled in a dry-ice bath to −78° C., and diisobutylaluminium hydride (2.5 mL, 1.0 M in $CH_2Cl_2$, 2.5 mmol) was slowly added via syringe over 5 min. After the addition was complete, stirring was continued for 48 h at room temperature. The reaction mixture was cooled to −78° C., carefully quenched with Rochelle salt (6 mL), and the reaction mixture stirred for 8 h and extracted with ethyl acetate (20 mL×3). The combined organic layers were dried over $Na_2SO_4$, filtered, and concentrated under a vacuum. The residue was purified by flash chromatography (silica gel; n-hexane:ethyl acetate:methanol (1:1:0.01) to obtain 24.5 mg (60% yield) of $^{13}C_6$-caffeyl alcohol.

Synthesis of $^{13}C_6$-Labeled Coniferyl Alcohol $^{13}C_6$-4-hydroxy-3-methoxybenzaldehyde (200 mg, 1.27 mmol) was added to a mixture of triethyl phosphonoacetate (0.75 mL, 3.78 mmol), DBU (0.4 mL, 2.53 mmol), and finely ground $K_2CO_3$ (522.4 mg, 3.78 mmol) and the resulting mixture stirred for 48 h at room temperature under argon. Ethyl acetate (10 mL) was added to the crude mixture and the solid was filtered off. The solid was rinsed with ethyl acetate (10 mL) and the combined filtrate was concentrated. The product, $^{13}C_6$-ferulic acid ethyl ester, was isolated by flash chromatography (silica gel; n-hexane:ethyl acetate=2: 1) as a colorless oil (260 mg, 90% yield).

$^{13}C_6$-Coniferyl alcohol was synthesized from $^{13}C_6$-ferulic acid ethyl ester following a variation of a process described by Min-Kim (Min-Kim, 2012, hereby incorporated by reference herein) (Scheme 7 A). $^{13}C_6$-ferulic acid ethyl ester (250.0 mg, 1.10 mmol) was dissolved in 12 mL of dichloromethane, under argon, cooled in a dry-ice bath to −78° C., and diisobutylaluminium hydride (11.0 mL, 1.0 M in $CH_2Cl_2$, 11.0 mmol) was slowly added via syringe over 5 min. After the addition was complete, stirring was continued for 48 h at room temperature. The reaction mixture was cooled to −78° C. and carefully quenched with Rochelle salt (12 mL). The reaction mixture was stirred for 8 h and extracted with ethyl acetate (50 mL×3). The combined organic layers were dried over $Na_2SO_4$, filtered, and concentrated under a vacuum. The residue was purified by flash chromatography (silica gel; n-hexane:ethyl acetate:methanol=2:1:0.01) to obtain 180.5 mg (88% yield) of $^{13}C_6$-coniferyl alcohol.

Bioinformatics Analysis

To identify the putative peroxidase and laccase genes in *Cleome*, the protein sequences of *Arabidopsis* peroxidases and/or laccases were searched against our previously generated *Cleome* RNA-seq database (Zhuo et al., 2019, incorporated by reference herein) using the TBLASTN program with default parameters. All obtained laccase sequences were further confirmed by searching the Pfam database (http://pfam.janelia.org) for the existence of three Cu-oxidase domains (PF00394.19, PF07731.11, and PF07732.12). The *Cleome* laccases were named ChLAC1-ChLAC22 according to their annotations in the *C. hassleriana* genome (ASM46358v1) at NCBI (Cheng et al., 2013) and their respective homologs in *Arabidopsis*. The exon-intron structures of the ChLAC genes were analyzed using Gene Structure Display Server (GSDS v2.0, http://gsds.cbi.pku.edu.cn/). The fragments per kilobase of transcript per million mapped reads (FPKM) values for peroxidase and laccase were retrieved from the transcriptome data and used for hierarchical clustering analysis.

The presence of signal peptides and the locations of their cleavage sites in the protein sequence of ChLAC8 were predicted using the online web server SignalP5.0 (http:// www.cbs.dtu.dk/services/SignalP-5.0/index.php) (Almagro Armenteros et al., 2019). Eukaryotes were chosen as the organism group. The subcellular localization of ChLAC8 was predicted using the online web server MultiLoc2 by the prediction method MultiLoc2-HighRes (plant) considering 10 localizations (https://abi-services.informatik.uni-tuebingen.de/multiloc2/webloc.cgi; Blum et al., 2009). N-Glycosylation sites in the protein sequence of ChLAC8 were predicted using the online web servers NtetNGlyc 1.0 (http://www.cbs.dtu.dk/services/NetNGlyc/) and N-GlyDE (http://bioapp.iis.sinica.edu.tw/N-GlyDE/) (Pitti et al., 2019).

Phylogenetic Analysis

The amino acid sequences of ChLAC proteins and characterized laccases from *Arabidopsis* and other plants were retrieved from the NCBI website. Multiple alignment of these laccase sequences was performed using the Clustal W algorithm (Thompson et al., 2003) and visualized using BoxShade 3.21 (https://embnet.vital-it.ch/software/BOX_form.html) with default setting. A phylogenetic tree was constructed using MEGA7.0 software by the Neighbor-joining algorithm with 1000 bootstrap replicates (Kumar et al., 2016). The tree was visualized and annotated by EvolView (https://evolgenius.info/evolview-v2).

RNA Isolation and qRT-PCR

Plant materials were ground to a fine powder in liquid nitrogen with a freezer mill (SPEX SamplePrep). Total RNA was isolated from the powdered samples using an RNeasy PowerPlant Kit (Qiagen) according to the manufacturer's protocol. The RNA quality and concentration were measured with an Agilent Bioanalyzer 2100. Approximately 2 μg of RNA per sample was treated with DNase I (Invitrogen) to remove residual genomic DNA and reverse transcribed to first-strand cDNA using the SuperScript III First-Strand Synthesis System (Invitrogen). qRT-PCR analysis was carried out with three biological replicates using SYBR Green Master Mix (Applied Biosystems) on a QuantStudio 6 Flex Real-Time PCR System (Applied Biosystems). The *Cleome* ubiquitin-conjugating enzyme E2 11-like gene (XM_010555091.2) was used as an internal standard to normalize the amount of cDNA template (Zhuo et al., 2019). All primers used are listed in Wang Supp. Table 4, as incorporated herein. Relative transcript levels were calculated using the formula for comparative Ct value (Ranasinghe et al., 2008).

Expression and Purification of ChLAC8 from *Escherichia coli*

The open reading frame (ORF) of ChLAC8 (ChLAC8X1, XM_010555066.1) was amplified with the primers listed in Wang Supp. Table 4, ligated into the pENTR/D-TOPO vector (Invitrogen), and subcloned into pDEST17 fused with a 6× histidine tag at the N-terminus via Gateway LR recombination reaction (Invitrogen). The resulting vector (pDEST17-ChLAC8) was transformed into *E. coli* Rosetta (DE3) (Novagen) for protein expression. The transgenic *E. coli* strain was cultured in LB medium at 37° C. until $OD_{600}$=0.4-0.6 and then supplemented with 0.5 mM isopropyl-β-D-thiogalactoside (IPTG) to induce the expression of ChLAC8 at 16° C. for 20 h. After induction, cell cultures were harvested by centrifugation at 10,000×g for 5 min at 4° C., and the resulting pellets were used for ChLAC8 protein purification via Ni-NTA resin (Thermo Scientific) according to the manufacturer's manual. The eluted protein was further desalted into 50 mM potassium phosphate buffer (pH 6.8) using a 30 kDa cut-off Amicon Ultra centrifugal filter (Millipore). The purity of recombinant ChLAC8 was examined by SDS-PAGE and the protein concentration was quantified by Bradford assays.

Analysis of Enzyme Kinetics

Laccase activity assays were performed in a 100 μL reaction mixture consisting of 50 mM potassium phosphate buffer (pH 6.8), 10-20 μg of recombinant ChLAC8, and 200 μM monolignol substrate (caffeyl alcohol, coniferyl alcohol or sinapyl alcohol). The reactions were incubated at 25° C. for 30 min and terminated by adding 100 μL of methanol. The reaction products were injected into an HPLC or LC-MS/MS system for analysis as described below. The decrease in the level of the substrate was measured to calculate the enzyme activity. To determine kinetic parameters, ChLAC8 was incubated with different concentrations of caffeyl alcohol or sinapyl alcohol in a range from 25 to 800 μM. The enzyme assays were performed in triplicate at each substrate concentration, and the Vmax and Km values were calculated by Graphpad Prism 8 software with non-linear regression analysis.

HPLC and LC-MS/MS Analysis of Reaction Products

The reaction products were analyzed on an Agilent 1260 HPLC system equipped with a Luna C18(2) reverse-phase column (5 μm particle, 250×4.6 mm, Phenomenex) and separated in a mobile phase consisting of solvent A (1% in phosphoric acid in water) and solvent B (acetonitrile) with the following gradient: 5% B for 5 min, to 33% B in 25 min, to 45% B in 5 min, to 95% B in 5 min, keep at 95% B for 5 min, back to 5% B in 5 min.

LC-MS/MS analysis was performed using an Agilent 1290 Infinity II liquid chromatography system coupled to an Agilent 6400 Series Triple Quadrupole System with electrospray ionization source in negative ionization mode. A reverse phase ZORBAX RR Eclipse Plus C18, 95 Å, 4.6× 250 mm, 5 μm (Agilent) was used for separation. The gradient for HPLC separation was 0.1% (v/v) formic acid in water (A) and 0.1% (v/v) formic acid in acetonitrile (B) with the following solvent gradient: 5% B for 5 min, to 40% B in 30 min, to 95% B in 5 min, 95% B for 5 min, to 5% B in 1 min. The total LC-MS/MS run was 46 min with a flow rate of 1.0 mL/min. Injection volume was 10 μL. MS data were recorded in the range of m/z 100-700 (Perna et al., 2018).

Quantification of monolignol intermediates was conducted using an Agilent 1290 Infinity II liquid chromatography system coupled to a hybrid Triple Quadrupole 6500+ triple quadrupole from AB SCIEX. The metabolites were separated using a reverse phase C18 Symmetry column (4.6×75 mm; 3.5 μm) with a Symmetry C18 pre-column (3.9×20 mm; 5 μm) from Waters. Details of the HPLC gradient and MS parameters were as previously described (Cocuron et al., 2019, incorporated herein by reference). Metabolites were simultaneously detected and quantified using multiple reaction monitoring (MRM) determined using standards of each metabolite. Monolignols were identified and quantified using a mixture of known external standards run at the same time as the biological extracts.

Homology Modeling and Docking Studies of ChLAC8

Comparative modeling of ChLAC8 was performed using the SWISS-MODEL server (Schwede et al., 2003) with the structure of ZmLAC3 (PDB ID: 6KLG) (Xie et al., 2020) as the template. The three-dimensional structural model of ChLAC8 was generated based on optimal sequence alignment of ChLAC8 and ZmLAC3 and the three-dimensional structure of ZmLAC3. Molecular docking studies of ChLAC8 with substrates (sinapyl, caffeyl, and coniferyl alcohols) were carried out using the automated docking program AUTODOCK (Morris et al., 2009), and the sinapyl alcohol model in the ZmLAC3 structure (PDB ID: 6KLI)

was used as a reference. Some minor manual adjustments of the modeling solution were made and the structure model was analyzed using the graphics program COOT (Emsley and Cowtan, 2004). Figures were prepared with PyMOL (The PyMOL Molecular Graphics System, Schrödinger, LLC).

RNAi Knockdown of ChLAC8 in the *Cleome* Seed Coat

An RNA interference construct targeting the ChLAC8 transcript was constructed by amplifying a nucleotide fragment from developing *Cleome* seed coat cDNA using the primers listed in Wang Supp. Table 4. The 162 bp ChLAC8 fragment was cloned into pENTR/D-TOPO (Invitrogen) and transferred to Gateway destination vector pH7GWIWG2(I) via LR reaction (Invitrogen). The resulting RNAi construct, which was driven by the constitutive cauliflower mosaic virus 35S promoter, was introduced into *Agrobacterium tumefaciens* strain AGL1. Transgenic plants harboring the ChLAC8 RNAi construct were generated by *Agrobacterium tumefaciens*-mediated transformation of *Cleome* embryonic callus tissue as previously described (Zhuo et al., 2019, incorporated herein by reference). The $T_0$ transgenic plants were checked by PCR using the hygromycin B phosphotransferase (HPH) gene as a marker with primers listed in Wang Supp. Table 4. The expression levels of ChLAC8 in different $T_1$ transgenic lines were verified by qRT-PCR. Two independent transgenic lines in the subsequent generation ($T_2$) exhibiting the highest downregulation of ChLAC8 transcripts were selected for further analysis. The lignin composition of the seed coat was determined by thioacidolysis methods (Lapierre et al., 1985; Chen et al., 2006) with docosane as the internal standard. The thioacidolysis monomer yields were calculated using the same response factor of 1.5 for all released lignin monomeric units (Lapierre and Monties, 1986). Approximately 2 mg dry weight of seed coats were used for analysis per replicate, and three biological replicates were analyzed.

Expression of ChLAC8 in *M. truncatula* Hairy Roots

The complete ORF of ChLAC8, including the N-terminal signal peptide, in the pENTR/D-TOPO vector (Invitrogen) was cloned into the pB7WG2D binary vector by LR recombination reaction (Invitrogen). Primers are listed in Wang Supp. Table 4. The resulting vector pB7WG2D-ChLAC8 with the ChLAC8 ORF driven by the CaMV 35S promoter was transformed into *Agrobacterium rhizogenes* strain ARqual. *Agrobacterium*-mediated *M. truncatula* hairy root transformation was performed as described previously (Liu et al., 2014). The *M. truncatula* comt mutant (NF17882) was as described previously (Ha et al., 2019). The resulting hairy roots were checked by PCR using the phosphinothricin acetyl transferase (BAR) gene as a marker. Primers are listed as stated above. Transcript levels of ChLAC8 and lignin composition were determined as described above. For each biological replicate, hairy root cultures were harvested from one tissue culture dish. Three biological replicates were analyzed.

Expression of ChLAC8 in *A. thaliana*

The vector pB7WG2D-ChLAC8 was transformed into *Agrobacterium tumefaciens* strain GV3101. *Agrobacterium*-mediated *Arabidopsis* transformation was performed by floral-dip (Clough and Bent, 1998). $T_1$ to $T_3$ transgenic plants were screened by spraying with 120 mg/L BASTA (Finale) and verified by PCR using the BAR gene as a marker. Primers are listed in Wang Supp. Table 4. After selecting the homozygous transgenic plants, transcript levels of ChLAC8 and lignin composition in the inflorescence stems were determined as described above. For each biological replicate, the inflorescence stems were harvested from three plants. Three biological replicates were analyzed.

**Feeding *Medicago* Hairy Roots with $^{13}C_6$-Caffeyl and Coniferyl Alcohols**

The portion 3 cm down from the root tip in *Medicago* hairy roots was cut under water, transferred into liquid MS medium supplemented with 100 μM $^{13}C_6$-caffeyl and $^{13}C_6$-coniferyl alcohols in 6-well plates, and vacuum infiltrated for 10 min. For each biological replicate, ~100 mg of hairy root cultures harvested from one tissue culture dish was put into one well. The samples were incubated for 2 days, harvested, and washed three times with water prior to isolation and analysis of lignin by thioacidolysis (Lapierre et al., 1985; Chen et al., 2006). $^{13}C$-incorporation was determined by measuring the m/z +6 ion peaks from the C- and G-unit thioacidolysis products. Three biological replicates were measured.

**Feeding *Arabidopsis* Stems with $^{13}C_6$-Caffeyl Alcohol**

The top portions of inflorescence stems of 4-week-old *Arabidopsis* plants were cut under water and transferred into liquid MS medium supplemented with 100 μM $^{13}C_6$-caffeyl alcohol in 2 mL tubes. The samples were incubated for 2 days, harvested, and analyzed as described above for hairy roots. Five stem fragments were harvested as one sample, and three biological replicates were measured.

Statistical Analysis

Unpaired two-tailed student's t-test was used to test the significance of differences in the lignin composition between *Cleome* RNAi and null lines, as well the kinetics of ChLAC8 toward caffeyl alcohol and sinapyl alcohol. Multiple comparisons were done by one-way ANOVA Duncan grouping at 0.05 probability level with SPSS Statistics (version 22; IBM). T-test and ANOVA results along with raw data are provided in Wang Supp. Data Sets 5 and 6 (Wang, X., et al., (2020), incorporated by reference above).

Results

The Expression Pattern of ChLAC8 Correlates with C-Lignin Accumulation During Seed Development

In *Cleome*, C-lignin is only deposited after 12 DAP in the seed coat and is not found in vegetative tissues (Tobimatsu et al., 2013). To identify candidate genes involved in C-lignin biosynthesis, we previously performed a comprehensive transcriptome analysis of RNA samples from different *Cleome* tissues (seed coat, stem, bark, fiber, and pith) and different stages of seed development (Zhuo et al., 2019). To determine whether specific enzymes might contribute to the polymerization of caffeyl alcohol, we interrogated this transcriptome database. Monolignol oxidation/polymerization is catalyzed by both peroxidases and laccases (Sterjiades et al., 1992; Bao et al., 1993; Barros et al., 2015; Tobimatsu and Schuetz, 2019), with laccase appearing to be essential for lignification in vascular tissues of *Arabidopsis* (Zhao et al., 2013). Seventy-two putative peroxidase transcripts were identified in our transcriptome database, but none of their transcript expression patterns correlated with C-lignin accumulation during seed development (see Wang, X., et al., (2020) Wang Supp. FIG. 1 and Data Set 1). By contrast, 24 putative laccase (ChLAC) genes, resulting in 32 transcripts, were found in the transcriptome. The transcript profiles of ChLAC8X1, ChLAC8X2 and ChLAC8X3 exhibited good correlations with C-lignin content during seed maturation. Specifically, these transcripts, like those encoding ChCAD5, a form of cinnamyl alcohol dehydrogenase with preference for caffeyl alcohol and functionally linked to C-lignin biosynthesis (Zhuo et al., 2019), were not expressed in vegetative tissues or during the period of G-lignin biosynthesis in the seed coat (FIG. 1A). The expression pattern of ChLAC8s was the inverse of the expression patterns of ChCOMTs and CCOAOMTs (FIG. 1A); these monolignol pathway O-methyltransferase genes are downregulated in order to block the 3-O-methylation reaction to allow for the formation of caffeyl alcohol.

Figure 1B:
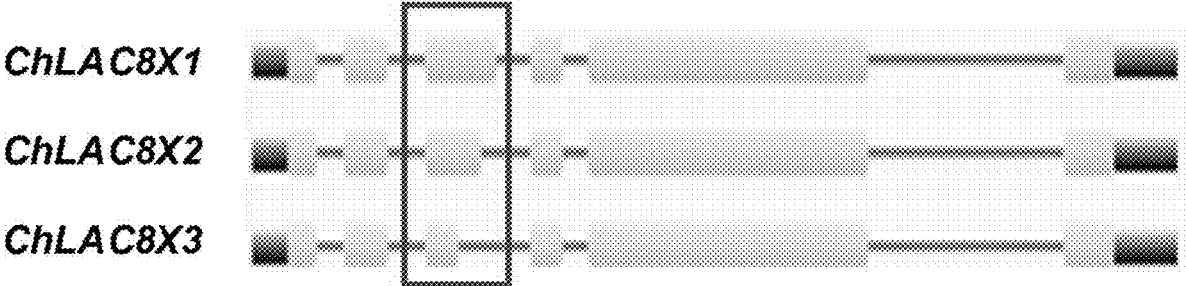
Figure 1C:
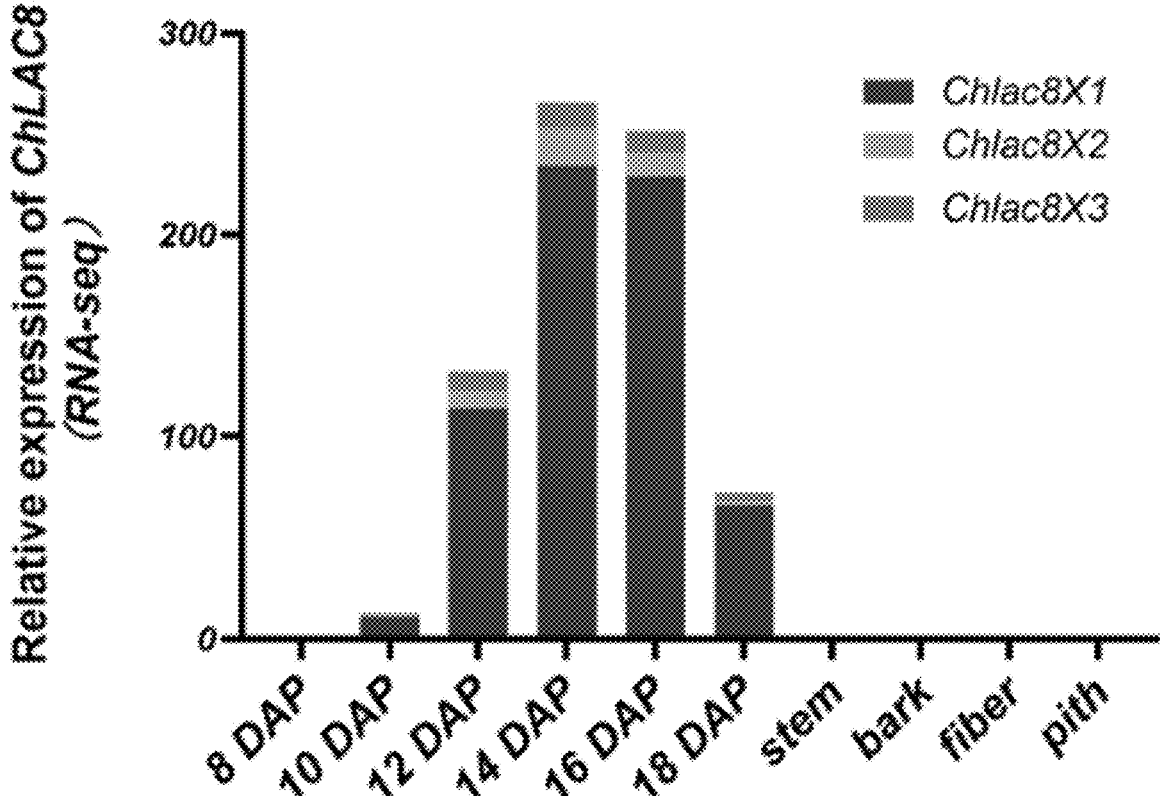

Like other ChLACs, the putative protein sequences of all three ChLAC8 variants contained three typical characteristic laccase cupredoxin-like domains, CuRO_1_LCC (cd13849), CuRO_2_LCC (cd13875), and CuRO_3_LCC (cd13897), which are responsible for the binding of copper ions (see Wang Supp. FIG. 2). These three transcripts were produced by the same gene locus (ChLAC8, LOC104823484) due to alternative splicing at the 5'-end of the third intron (FIG. 1B). However, ChLAC8X3 lacked a significant proportion of the copper-binding domain, including two amino acid residues (His128 and His130 of ChLAC8X1) that coordinate to Cu atoms, and therefore likely encodes an inactive enzyme. Analysis by the online tool SignalP5.0 (Almagro Armenteros et al., 2019) indicated that ChLAC8 contains a typical N-terminal signal peptide with a cleavage site between amino acids 25 and 26. The subcellular localization of ChLAC8 was predicted to be extracellular with a certainty value of 0.92 by the online tool MultiLoc2 (Blum et al., 2009). Like other laccases, ChLAC8 is a glycoprotein, with 10 putative N-glycosylation sites (Wang Supp. Table 1) predicted using the online web servers NtetNGlyc 1.0 (http://www.cbs.dtu.dk/services/NetNGlyc) and N-GlyDE (http://bioapp.iis.sinica.edu.tw/N-GlyDE) (Pitti et al., 2019).

Although the three ChLAC8 transcript variants showed similar expression patterns in our transcriptome database, ChLAC8X1 had more than 10-fold higher transcript level than the other two forms (FIG. 1C), making it a strong candidate for involvement in C-lignin polymerization in the seed coat of *Cleome*. We further analyzed ChLAC8 transcript levels by qRT-PCR, revealing a similar expression pattern to that obtained from the RNA-seq results (Wang Supp. FIG. 3).

ChLAC8 is Phylogenetically Distinct from Functionally Characterized Laccases Involved in Lignin Biosynthesis

Figure 1D:
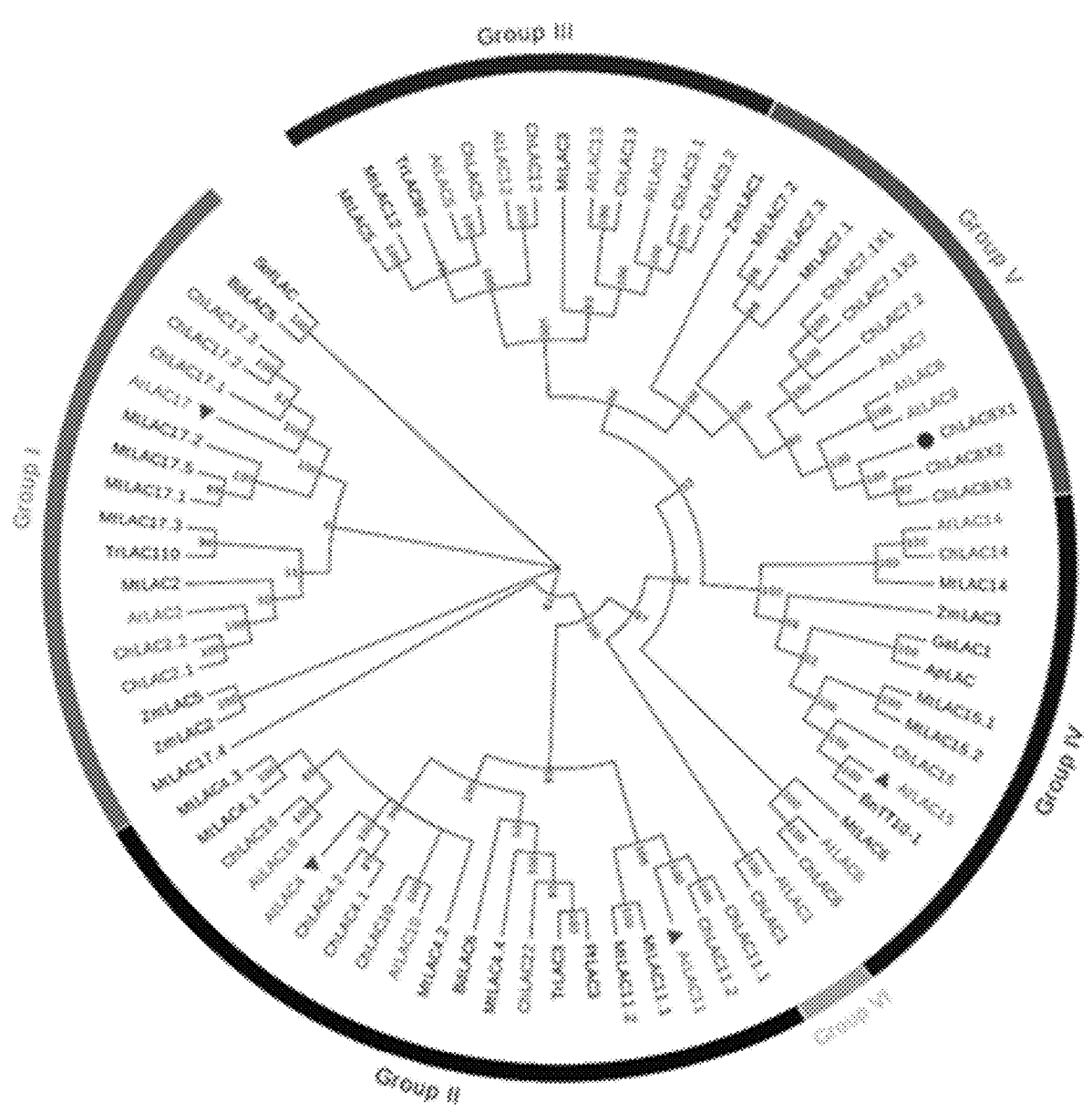

To investigate the evolutionary relationship between ChLAC8 and other plant laccases, we constructed a neighbor-joining tree with *Cleome* ChLACs, *Arabidopsis* AtLACs, *Medicago* MtLACs, and laccases that were previously characterized to be involved in lignification (Caparrós-Ruiz et al., 2006; Wang et al., 2015a,b; Bryan et al., 2016) (FIG. 1D). Similar to *Arabidopsis* laccases, ChLAC members are divided into six subgroups (group I to VI) (Turlapati et al., 2011). ChLAC8 is a homolog of AtLAC8 and AtLAC9 in group V, the exact functions of which are not known. In addition, ChLAC8 is phylogenetically distinct from AtLACs 4, 11, and 17, the three laccases that have been functionally ascribed roles in lignification in vascular tissues. It is also distinct from AtLAC15, more commonly known as TT10, which has been linked genetically to the oxidation of flavan-3-ols during the biosynthesis of condensed tannins (CTs) in the seed coat (Pourcel et al., 2005). Loss of function of AtLAC15 results in a transparent testa (TT) phenotype ascribed to a lack of tannin oxidation, but AtLAC15 has also been ascribed a role in lignin biosynthesis (Liang et al., 2006). The *Cleome* homolog of AtLAC15, ChLAC15, is also exclusively expressed in the seed coat, but mostly at early stages of development (FIG. 1A). This expression pattern is similar to that of ChANR, encoding anthocyanidin reductase, the key enzyme of CT biosynthesis (FIG. 1A)

Figure 4A:
FIGS. 4A-4G illustrate down-regulation of ChLAC8 by RNA interference in transgenic *cleome* plants.
Figure 4B:

(Xie et al., 2003), and is consistent with the staining of CTs in the seed coat before the appearance of C-lignin (Wang Supp. FIG. 4B). ChLAC5 is also expressed in the seed coat, at a similar transcript level to CHLAC8 (Wang Supp. FIG. 4A) but is also expressed in vegetative tissues and was therefore not pursued further.

Figures 5E, 5F, 5G:
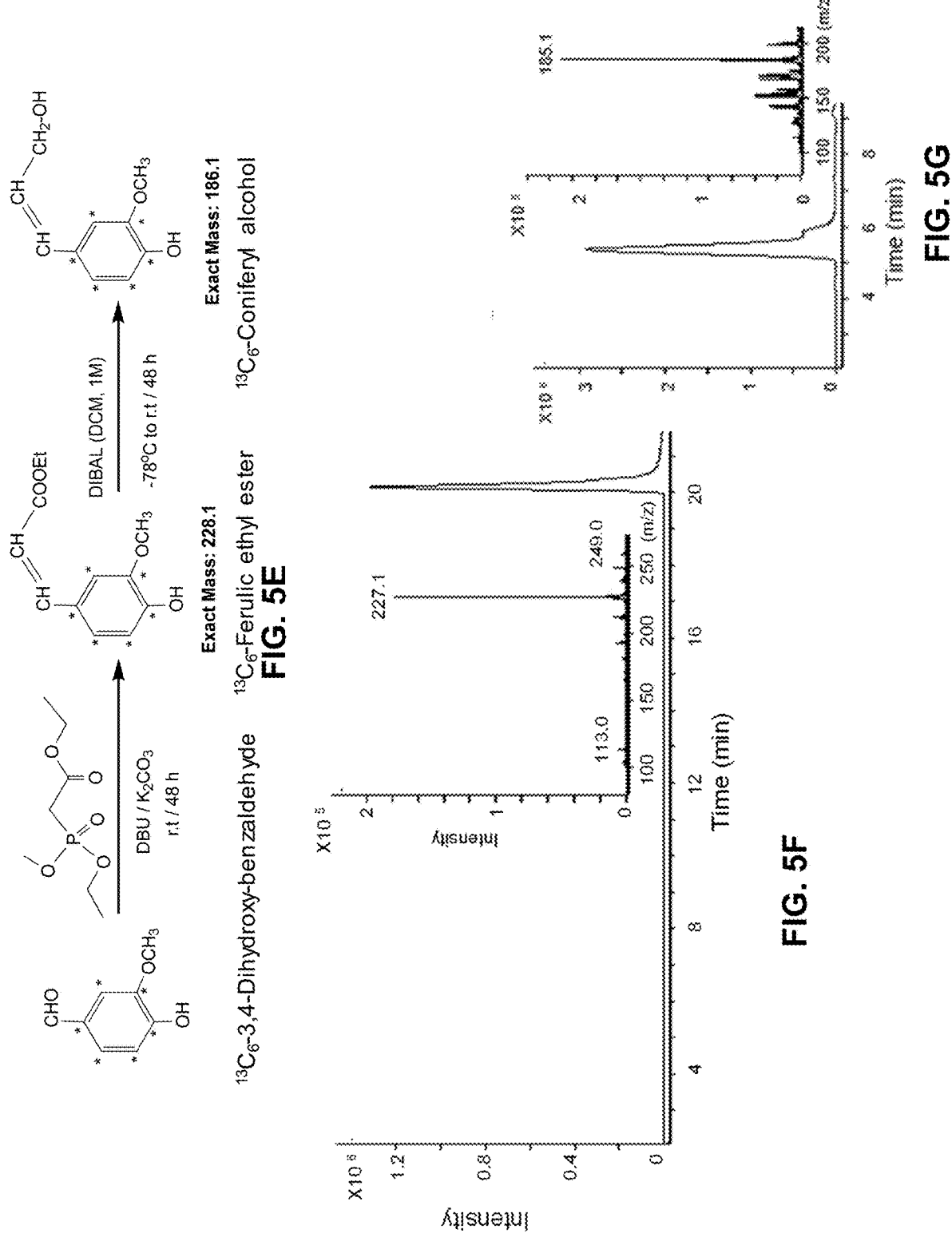

Recombinant ChLAC8 Oxidizes Caffeyl and Sinapyl Alcohols but not Coniferyl Alcohol As ChLAC8X1 was the full-length transcript with the highest expression, we expressed it in *E. coli* and further purified the protein from bacterial extracts by His-Tag affinity chromatography (Wang Supp. FIG. 5). To test the catalytic properties of recombinant ChLAC8 in vitro, we analyzed the oxidation of different monolignols by calculating the decrease in substrates by HPLC in the presence of this enzyme (FIGS. 2A-2F). ChLAC8 could oxidize caffeyl alcohol (C-unit) and sinapyl alcohol (S-unit), but, surprisingly, not coniferyl alcohol (G-unit).

Figure 2A:
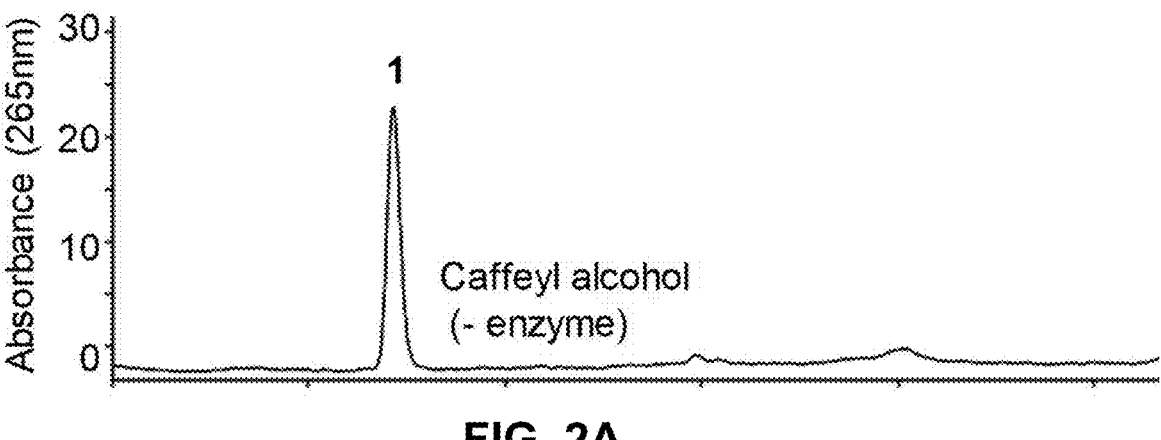
FIGS. 2A-2L illustrate HPLC and LC-MS/MS Analysis of Reaction Products of ChLAC8 with Different Monolignols.
Figure 2B:
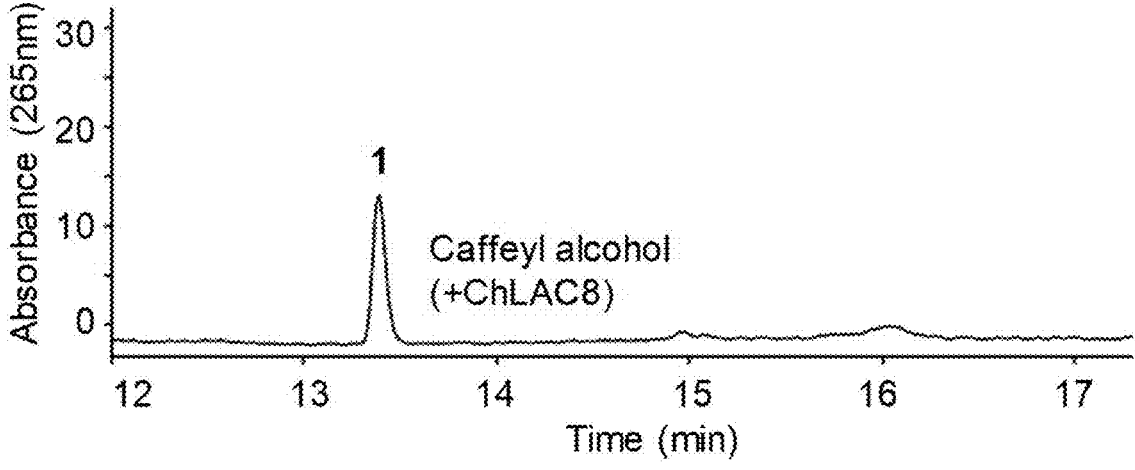
Figure 2C:
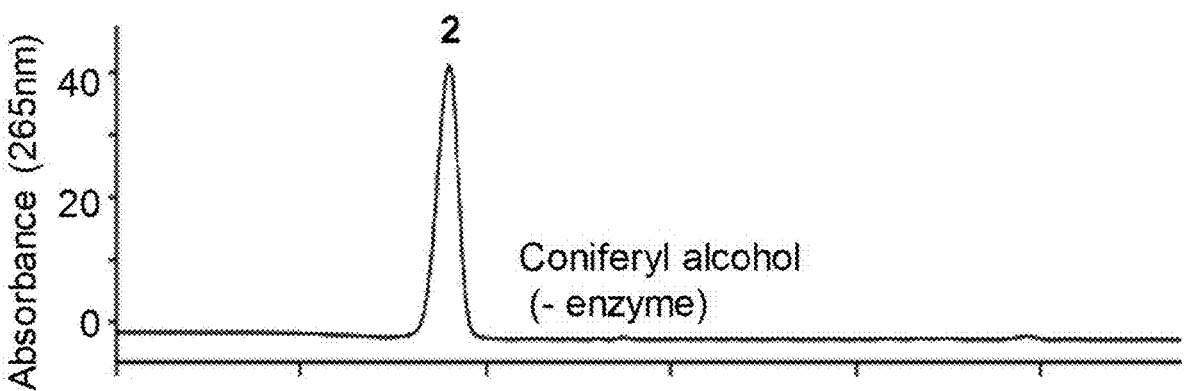
Figure 2D:
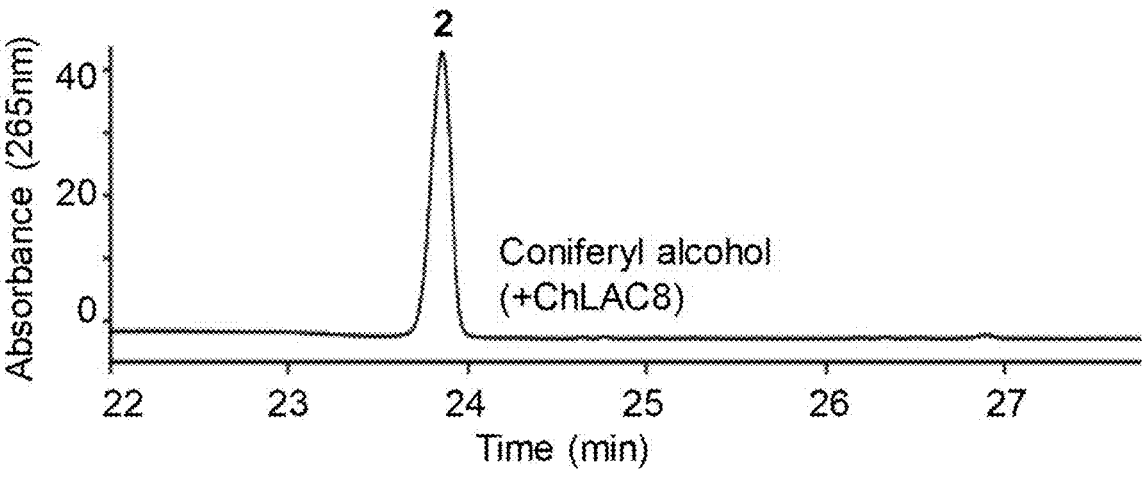
Figure 2E:
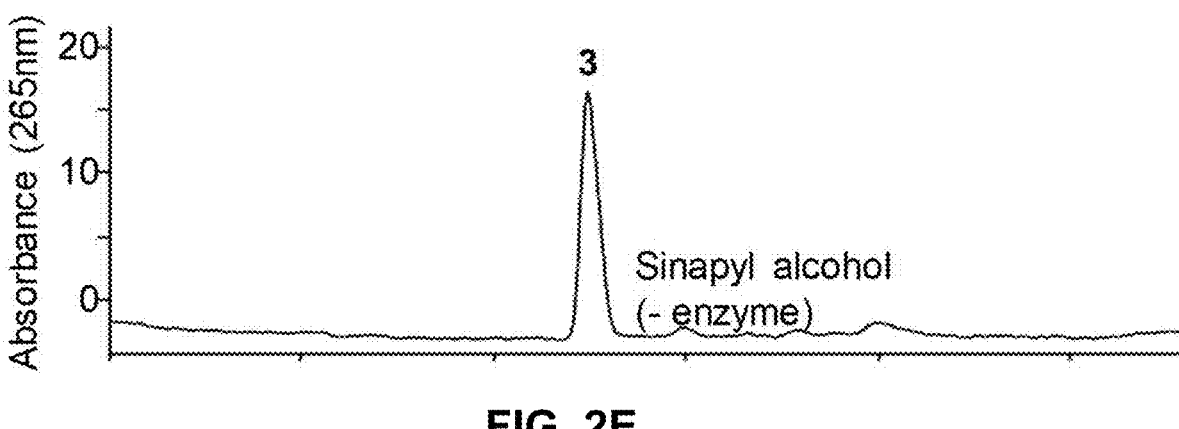
Figure 2F:
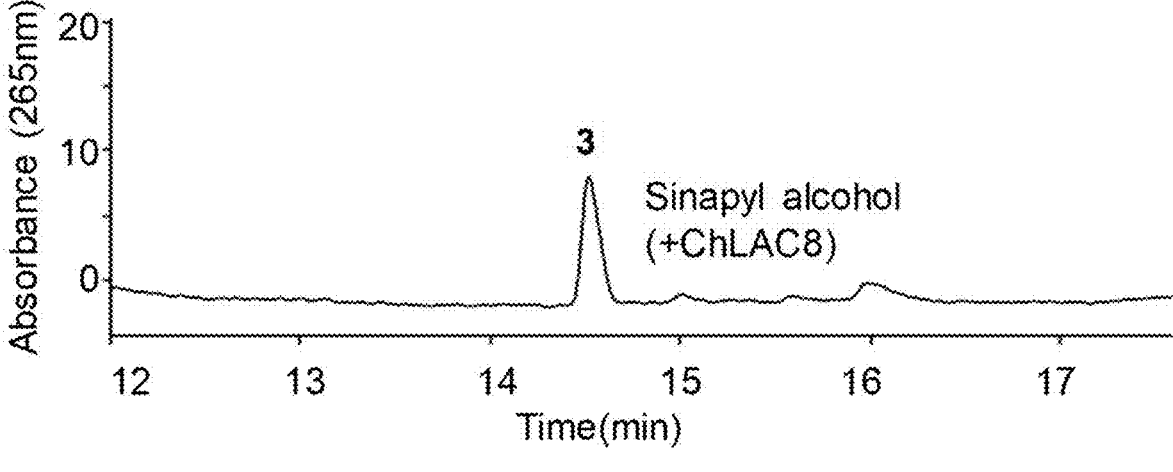
Figures 2G, 2H, 2I:
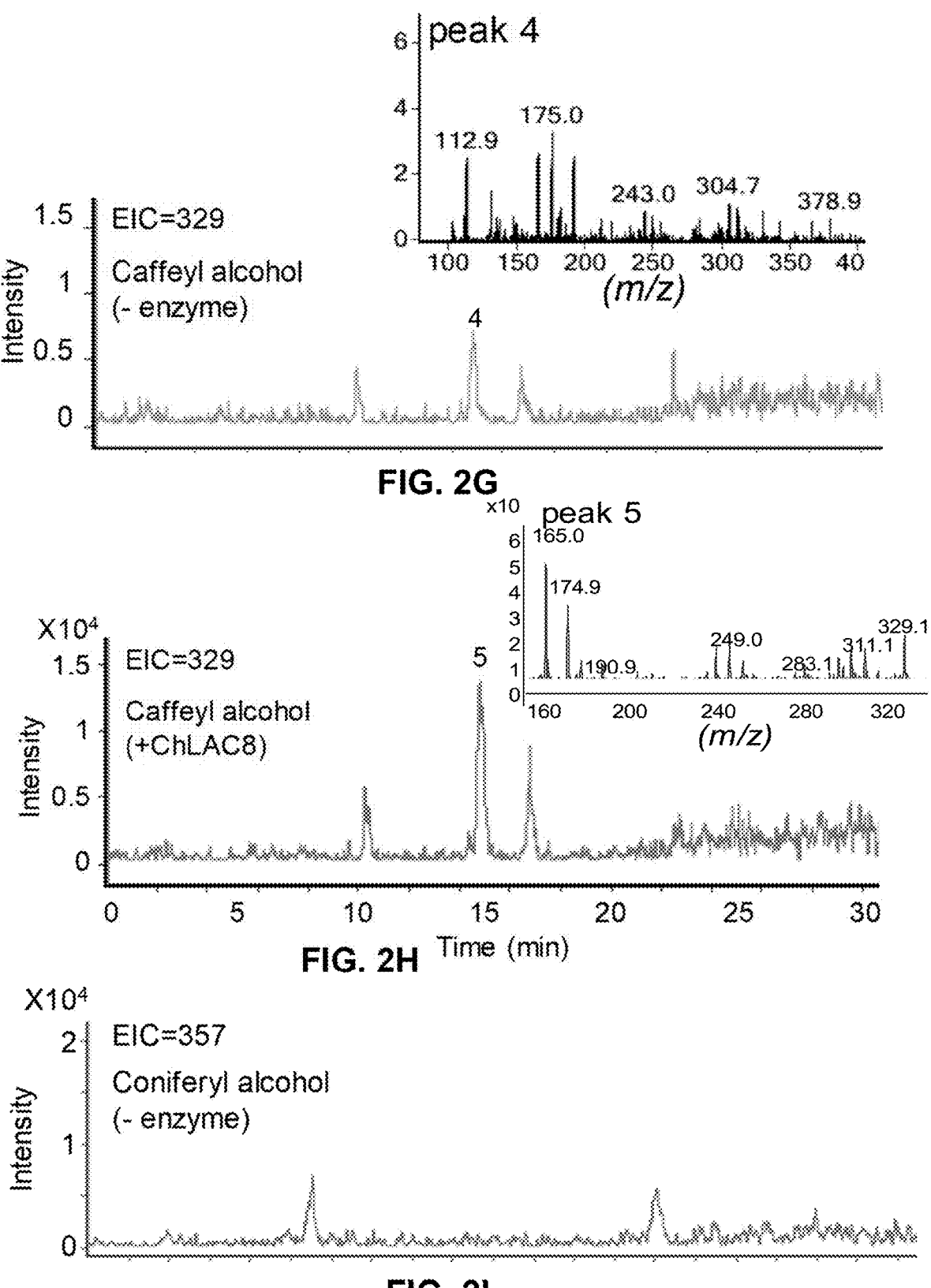
Figures 2J, 2K, 2L:
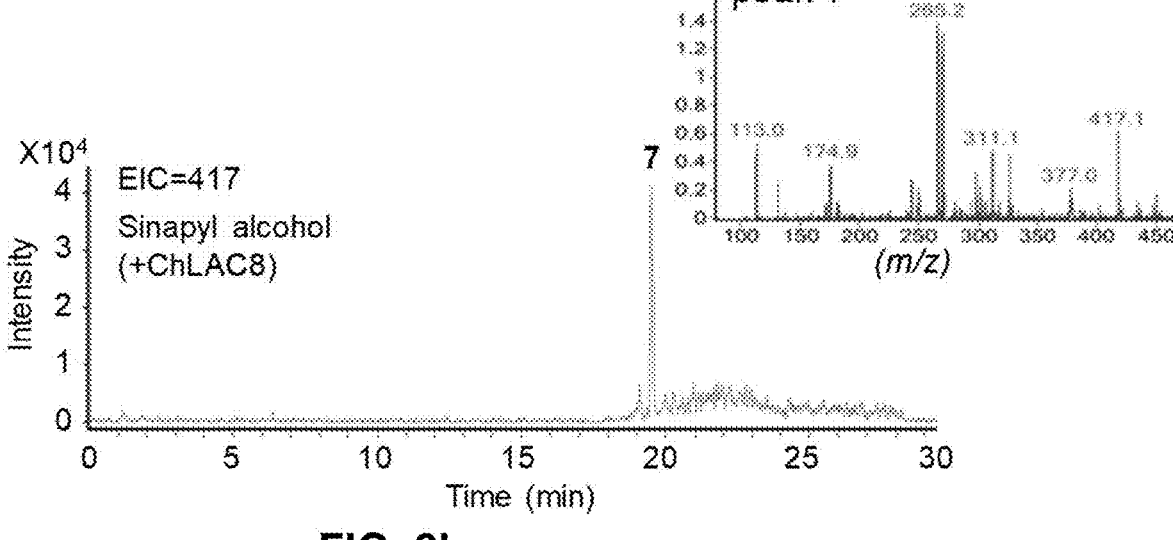
Figure 6F:
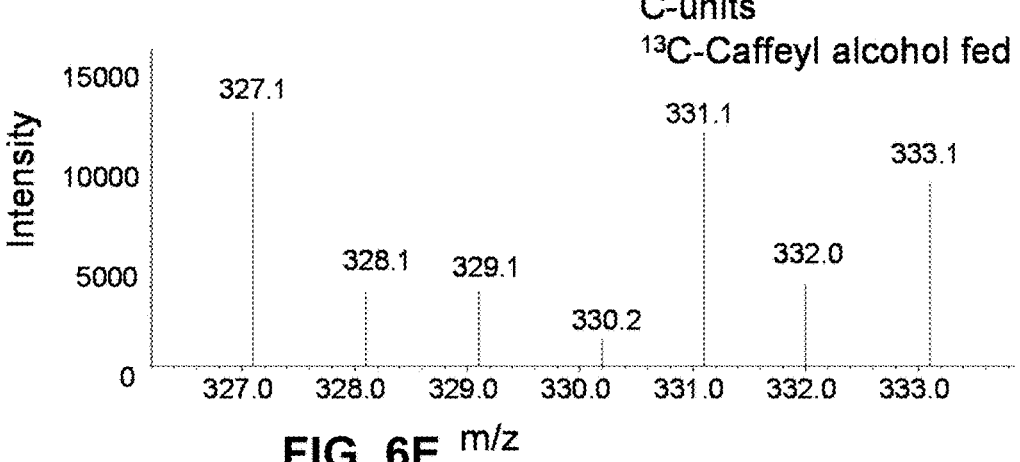
Figure 6F:
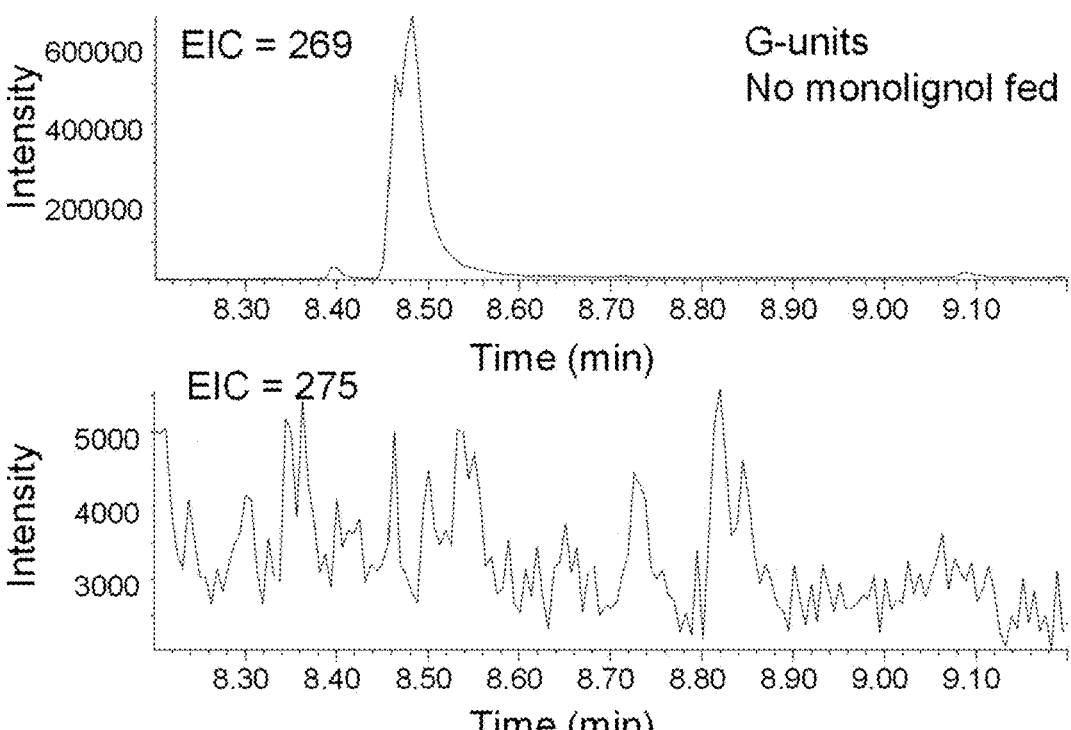

We analyzed the products generated from caffeyl and sinapyl alcohols by LC-MS/MS (FIGS. 2G-2L). Analysis of the extracted ion chromatograms (EIC) and MS spectra of product profiles showed that the primary products (peaks 5 and 7) were consistent with the masses of dimers of the corresponding substrates (peak 5, $m/z=329$ for dimer of caffeyl alcohol; peak 7, $m/z=417$ for dimer of sinapyl alcohol). No dimers were detected in the reaction products from coniferyl alcohol (FIG. 2J) or the control reactions (FIGS. 2G, 2I, 2K). This finding confirms that ChLAC8 can oxidize caffeyl and sinapyl alcohols to generate their corresponding radicals in vitro. In addition, trimers were observed in the products generated from caffeyl alcohol (Wang Supp. FIG. 6, peak 2, $m/z=493$ for trimer of caffeyl alcohol). No trimers were detected in the reaction products from sinapyl alcohol or controls without ChLAC8.

The $m/z$ values of the extracted ions of C-dimers for all three potential bonding modes (benzodioxane, phenylcoumaran and resinol) are 329. The mass spectra of the dimers generated from caffeyl alcohol also showed a major peak ion at $m/z=165$ (inset, FIG. 2H). This can only arise from the breakdown of a benzodioxane-linked dimer, according to the scheme shown in Wang Supp. FIG. 7. The $m/z$ values for dimers of sinapyl alcohol will differ between resinols and β-aryl ethers (417 and 435, respectively). The data in FIG. 2L showing the EIC at 417 indicate the formation of S-dimers as resinols joined via 8-8 linkage, but an ion was not detected at $m/z=435$.

Next, we determined the kinetic parameters of ChLAC8 by measuring reaction rates over a range of different substrate concentrations. The Km value of ChLAC8 for caffeyl alcohol was ~3.5-fold higher than that for sinapyl alcohol (Table 1). As a result, the catalytic efficiency (Kcat/Km) of ChLAC8 for caffeyl alcohol (92.53 $M^{-1}s^{-1}$) was lower than that for sinapyl alcohol (218.0 $M^{-1}s^{-1}$). However, sinapyl alcohol is not a natural substrate for laccase activity in the *Cleome* seed coat, which does not accumulate S-lignin due to the lack of expression of ferulate/coniferaldehyde 5-hydroxylase (F5H) (Zhuo et al., 2019).

TABLE 1

| Enzymatic Activity and Kinetic Parameters of Recombinant ChLAC8 Toward Different Monolignols | | | | |
|---|---|---|---|---|
| Substrate | Vmax (pKat mg$^{-1}$) | Km (μM) | Kcat (sec$^{-1}$) | Kcat/Km (M$^{-1}$sec$^{-1}$) |
| Caffeyl alcohol | 284.4 ± 50.4* | 210.3 ± 90.6* | 0.019 ± 0.003* | 92.53 |
| Coniferyl alcohol | N.D. | N.D. | N.D.- | N.D. |
| Sinapyl alcohol | 192.0 ± 12.8 | 60.2 ± 16.7 | 0.013 ± 0.001 | 218.0 |

Molecular Modeling of ChLAC8 Catalysis

Figure 3A:
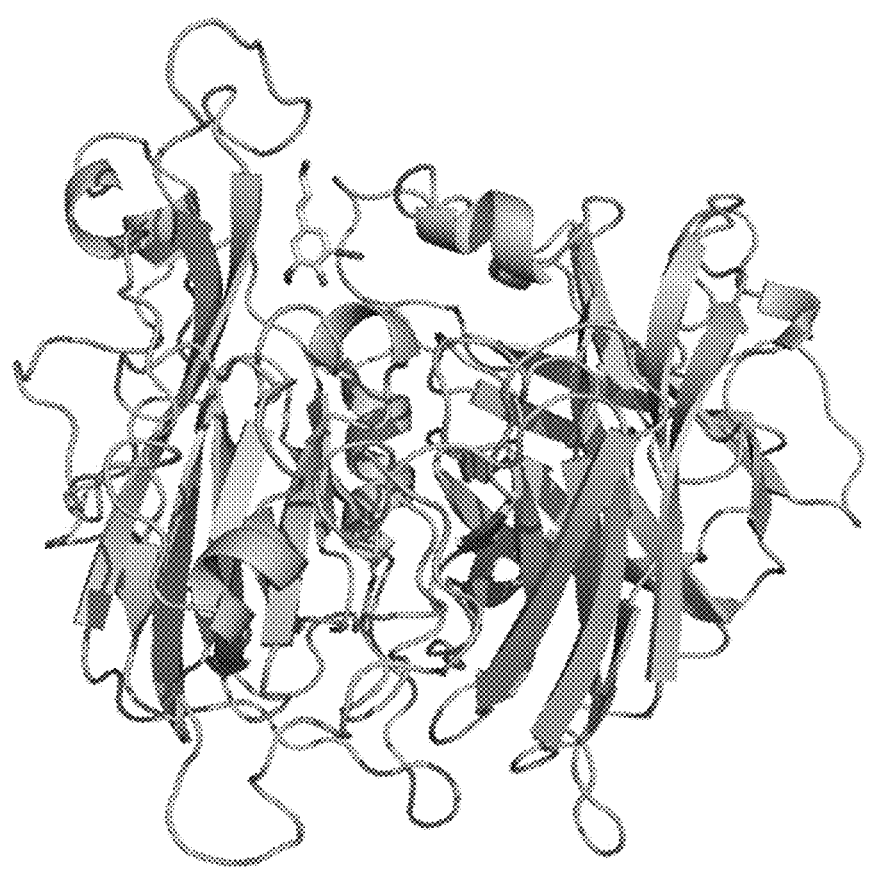
FIGS. 3A-3D are illustrations examining the binding of monolignols in the active site of ChLAC8 by molecular modeling.

To understand the substrate specificity of ChLAC8, we performed molecular modeling and docking studies. Using the structure of ZmLAC3 (PDB ID: 6KLG) (Xie et al., 2020) as a template, the three-dimensional structural model of ChLAC8 was obtained (FIG. 3A). ZmLAC3 is in a different but adjacent group from ChLAC8 in the cladogram, closer to ChLAC15 (FIG. 1D). However, similar to ZmLAC3, ChLAC8 consists of three cupredoxin-like domains, one mononuclear copper (T1 Cu) site, and one trinuclear copper (TNC) site. The T1 Cu is coordinated by His466, His534, and Cys529. In the TNC site, each of the two T3 Cu atoms is coordinated to three His residues (His85/His128/His530 and His130/His471/His528, respectively), and the T2 Cu is coordinated to two His residues (His83 and His249).

Figure 3B:
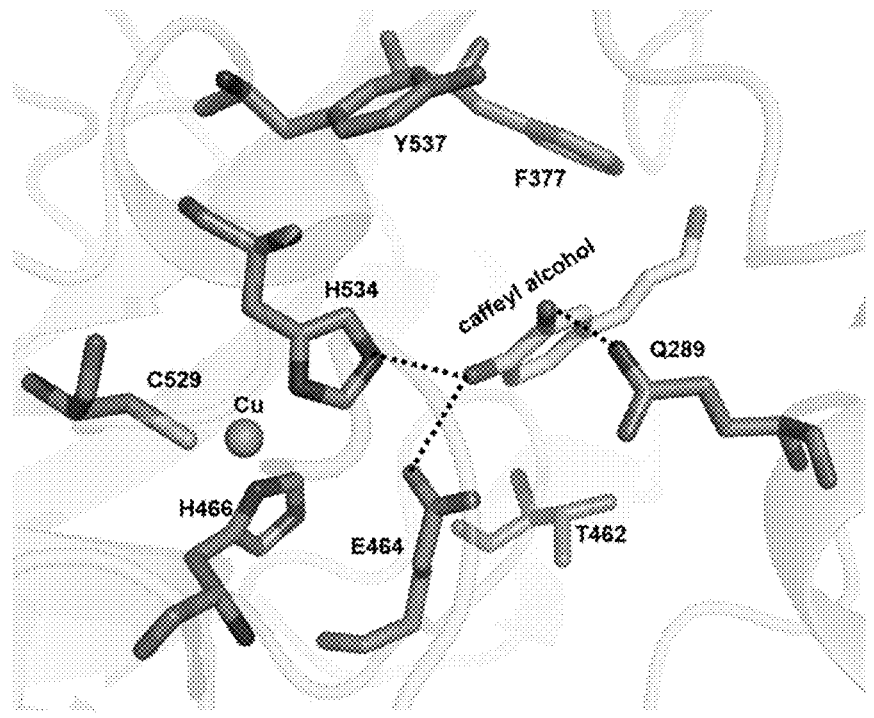
Figure 3C:
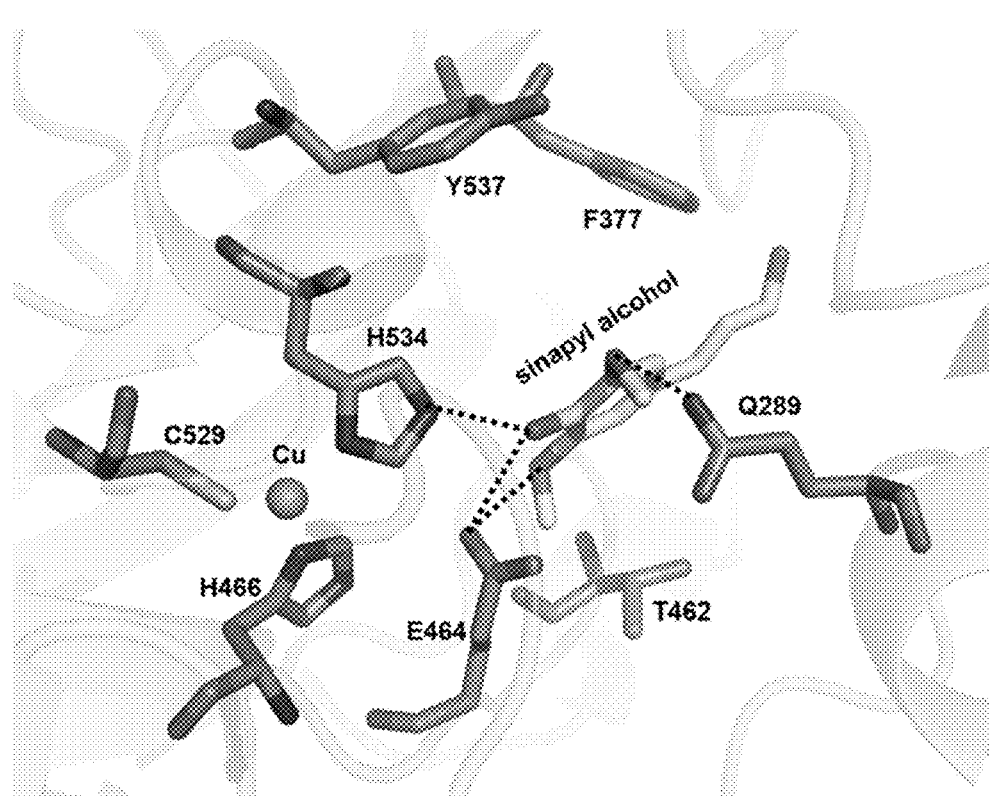
Figure 3D:
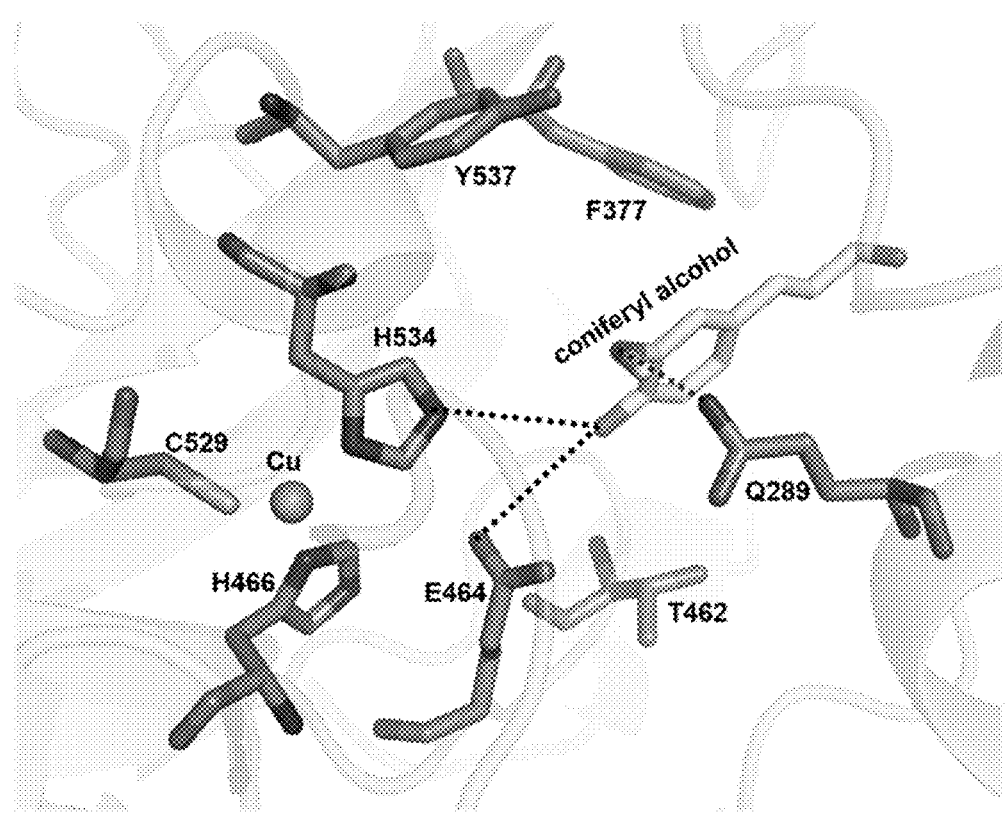

The putative substrate-binding pocket contains residues Ala286, Gln289, Leu358, Phe377, Thr462, Ile461, Glu464, Ala533, His534, and Tyr537 (FIGS. 3B-3D). Both caffeyl and sinapyl alcohols, as substrates, were docked with their 4-OH groups close to His534, which serves as the primary electron acceptor. In the model docked with caffeyl alcohol, the 3-OH of the substrate would form a strong hydrogen bond with Gln289, allowing stable maintenance of caffeyl alcohol in the active site for catalysis (FIG. 3B). In the model with docked sinapyl alcohol, its 3-OMe forms a weak hydrogen bond with Gln289, but its 5-OMe forms a hydrogen bond with Glu464 to maintain its position near His534 for catalysis (FIG. 3C). However, coniferyl alcohol lacks a 5-OMe; its 3-OMe alone may not form a strong enough interaction with Gln289 to maintain the compound in the active site for efficient catalysis (FIG. 3D). Based on this model, Gln289 appears to be involved in the binding of caffeyl alcohol in the active site of ChLAC8.

Multiple sequence alignment of all laccases in *Arabidopsis, Medicago,* and *Cleome* showed that the regions around Gln289 are divergent, whereas Glu464 and His534 are conserved among the laccases from these species (Wang Supp. FIG. 8). Finally, multiple sequence alignment of ChLAC8 with its *Arabidopsis* homolog and *Arabidopsis* and *Cleome* homologs of two laccases shown to be important for lignin biosynthesis (LAC4 and LAC17) indicated that Gln289 is found only in ChLAC8 (Wang Supp. FIG. 9).

RNAi-Mediated Downregulation of ChLAC8 Decreases the C-Lignin Content in *Cleome* Seed Coats To test the role of ChLAC8 in C-lignin polymerization in planta, we generated 14 independent $T_1$ transgenic RNAi lines of *Cleome* in which ChLAC8 was targeted for downregulation by RNA interference. To screen the $T_1$ plants, we determined the transcript levels of ChLAC8 and the lignin composition in the seed coats by qRT-PCR and thioacidolysis, respectively. ChLAC8 transcript levels displayed a strong positive correlation (r=0.737) with C-unit content for different $T_1$ transgenic lines, while exhibiting a weaker positive relationship with G-unit content (r=0.593), C/G ratio (r=0.668), and the total content of C- and G-units (r=0.669) (Wang Supp. FIG. 10).

Figure 4D:
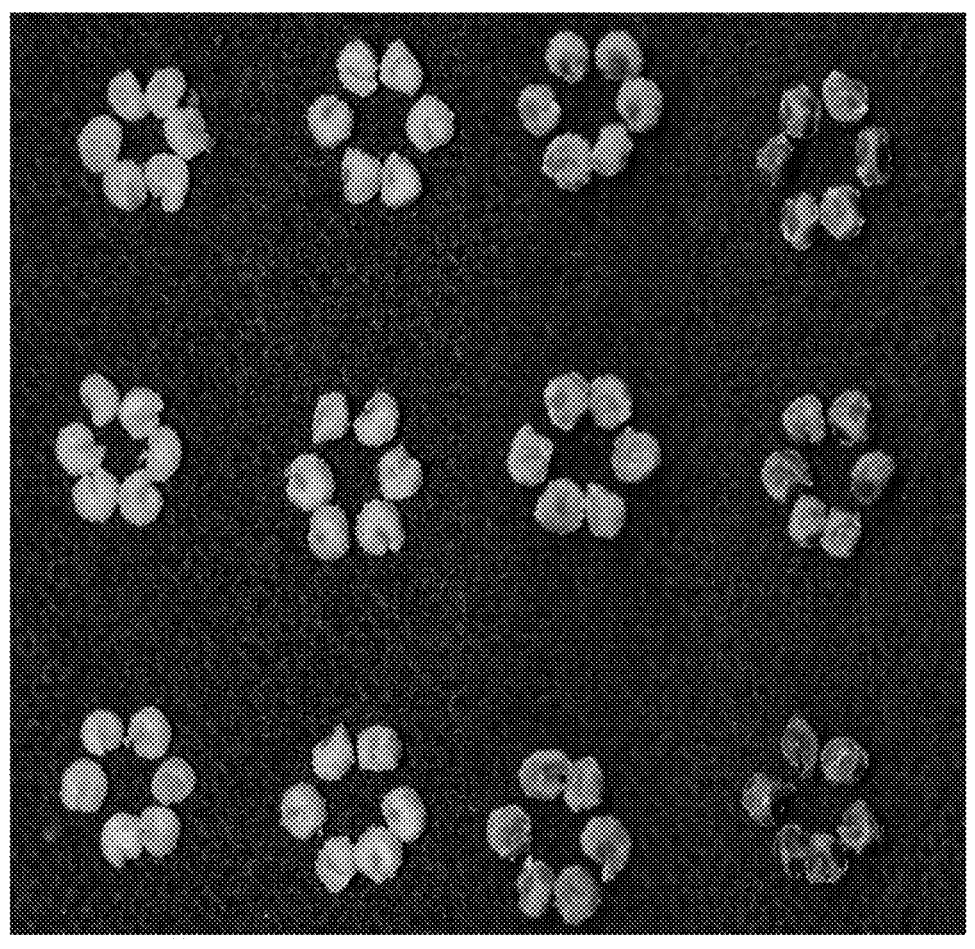
Figure 4C:
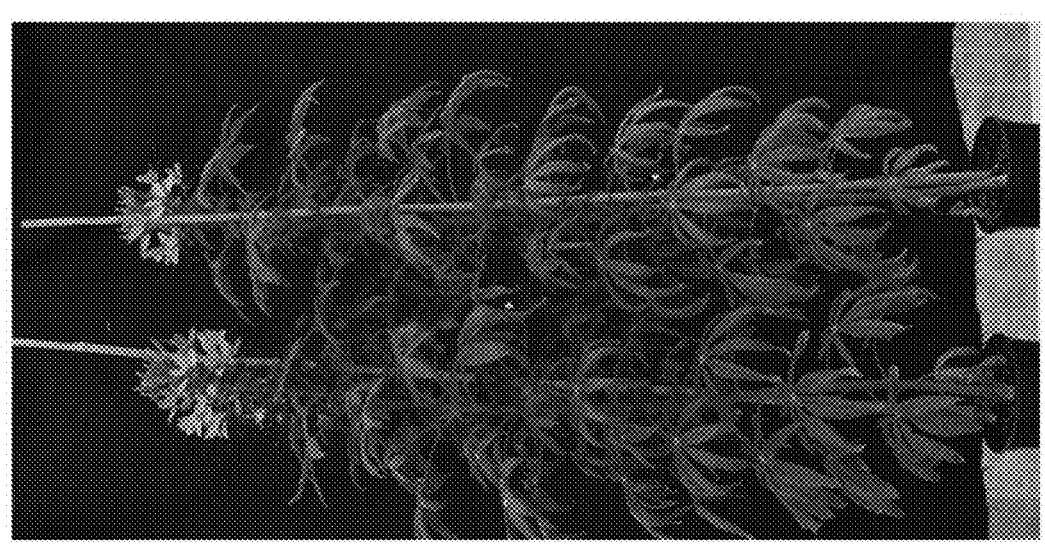
Figure 4E:
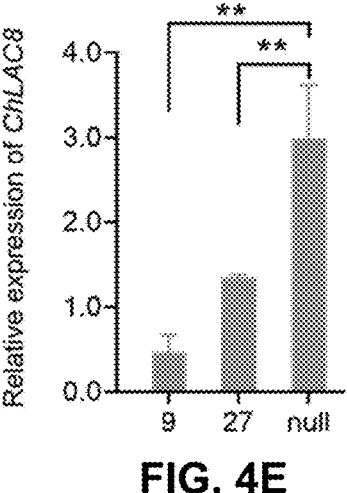
Figure 4F:
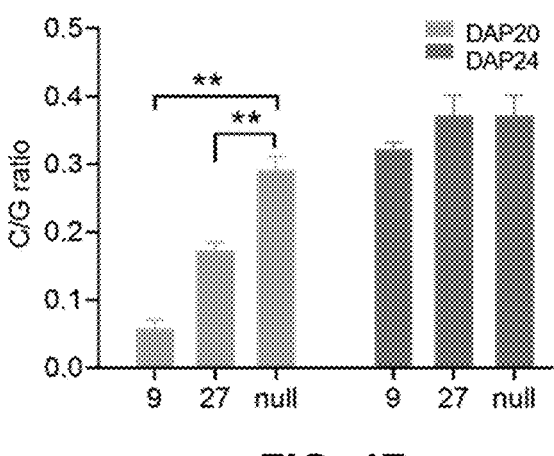
Figure 4G:
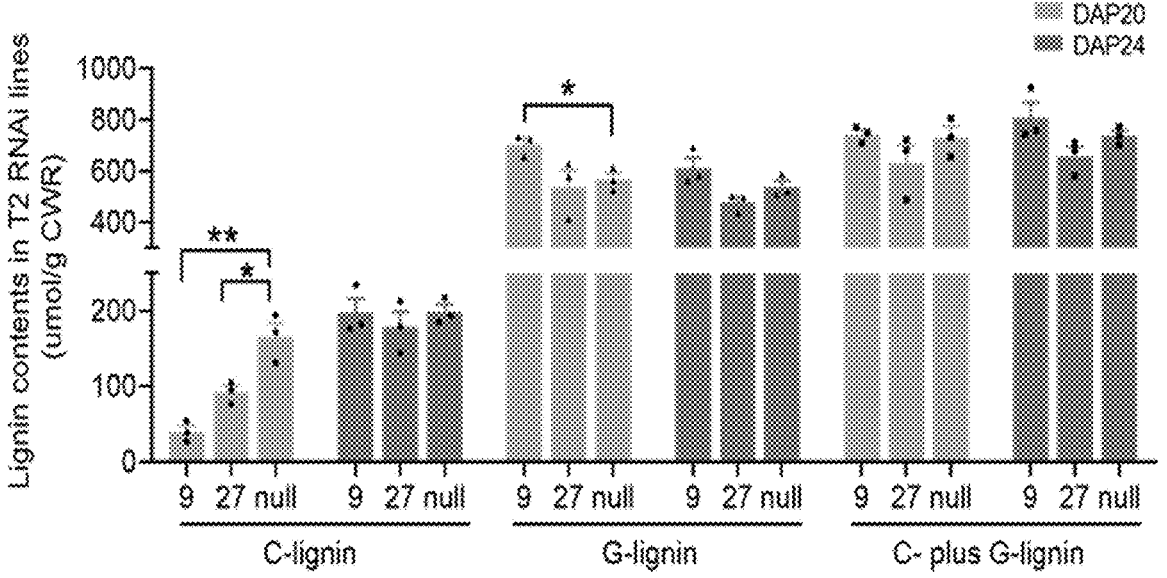

We selected two independent $T_2$ transgenic lines (RNAi-9 and RNAi-27) with substantial downregulation of ChLAC8 for further analysis. Knock-down of ChLAC8 expression had no effects on plant growth rate, leaf size, or flowering time (FIGS. 4A-4C), and the seed coats were morphologically similar, although the color of the coats was slightly lighter in the two independent RNAi lines (FIG. 4D). At 20 DAP, the C-units levels and C/G ratios, as determined by thioacidolysis, were significantly reduced in the seed coats of the two RNAi lines compared to null segregant plants, and appeared to be proportional to ChLAC8 transcript levels among these plants (FIGS. 4E-4G). By contrast, neither the G-unit nor total lignin (C- plus G-units) contents were consistently altered in the ChLAC8 downregulated plants, although the G-unit contents did appear to increase slightly in line RNAi-9 at 20 DAP, which might have compensated for the reduced levels of C-units at this time point (FIG. 4G). When the seed coats were examined at 24 DAP, there was no significant reduction in C-unit levels or C/G ratios (FIGS. 4F, 4G). These data are consistent with the role of ChLAC8 in the initiation, or at least the early stages, of C-lignin polymerization.

We examined the levels of monolignol pathway intermediates in the seed coats of the RNAi-9 and null lines at 20 DAP by LC-MS/MS (Wang Supp. Table 3). The levels of ferulic acid and coniferaldehyde were significantly increased in the ChLAC8-RNAi line. Coniferaldehyde is a direct precursor of both ferulic acid via aldehyde dehydrogenase (Nair et al., 2004) and coniferyl alcohol via CAD. Although there appeared to be slightly more coniferyl alcohol and slightly less caffeyl alcohol in the RNAi line, none of the differences was significant, and it is not clear why precursors of coniferyl alcohol should accumulate in this line. The reduction of C-units in the lignin in the knockdown lines was therefore likely caused by reduced initiation or polymerization rather than by reduced substrate supply.

Synthesis of Labeled Monolignols and Determination of their Incorporation into Lignin We next addressed the in vivo activity of ChLAC8 through gain-of-function approaches. To better follow changes in lignin composition in response to altered expression of ChLAC8, we decided to perform labeling experiments with $^{13}$C-caffeyl alcohol and $^{13}$C-coniferyl alcohol. After testing several approaches to the synthesis of these labeled compounds, we finally used the schemes outlined in FIGS. 5A, 5E. It was not possible to use the same synthetic approach for both compounds because of the additional reactivity of the ortho-dihydroxy substitution on the aromatic ring of caffeyl alcohol and its synthetic precursors. Full details of the syntheses are given in the Methods; the compounds were confirmed by LC-MS, and purities of the intermediates and final products are shown in FIGS. 5B-D, 5F, 5G.

Thioacidolysis products derived from incorporation of $^{13}$C-labeled monolignols into lignin have m/z values with 6 extra mass units (FIG. 6A), and these can be readily distinguished from the unlabeled monolignol thioethethyl derivatives at the same retention time during GC/MS analysis (FIGS. 6B-6I).

Expression of ChLAC8 Increases S- and C-Lignin Content in *Medicago* and *Arabidopsis*

To examine ChLAC8 by a gain-of-function approach, we first expressed the ChLAC8 open reading frame (ORF) in hairy roots of the *M. truncatula* comt mutant (Ha et al., 2019). In the *Cleome* seed coat, both COMT and CCOA- OMT genes are downregulated at the time of C-lignin biosynthesis, but *Arabidopsis* and *Medicago* comt ccoaomt double mutant plants are severely compromised in their growth (Do et al., 2007; Zhou et al., 2010; Ha et al., 2019). If caffeyl alcohol can be produced in *Medicago* hairy roots, loss of function of COMT might prevent its conversion to coniferyl alcohol, as caffeyl alcohol is one of the best substrates for *Medicago* COMT (Parvathi et al., 2001).

Figures 7A, 7B, 7C:
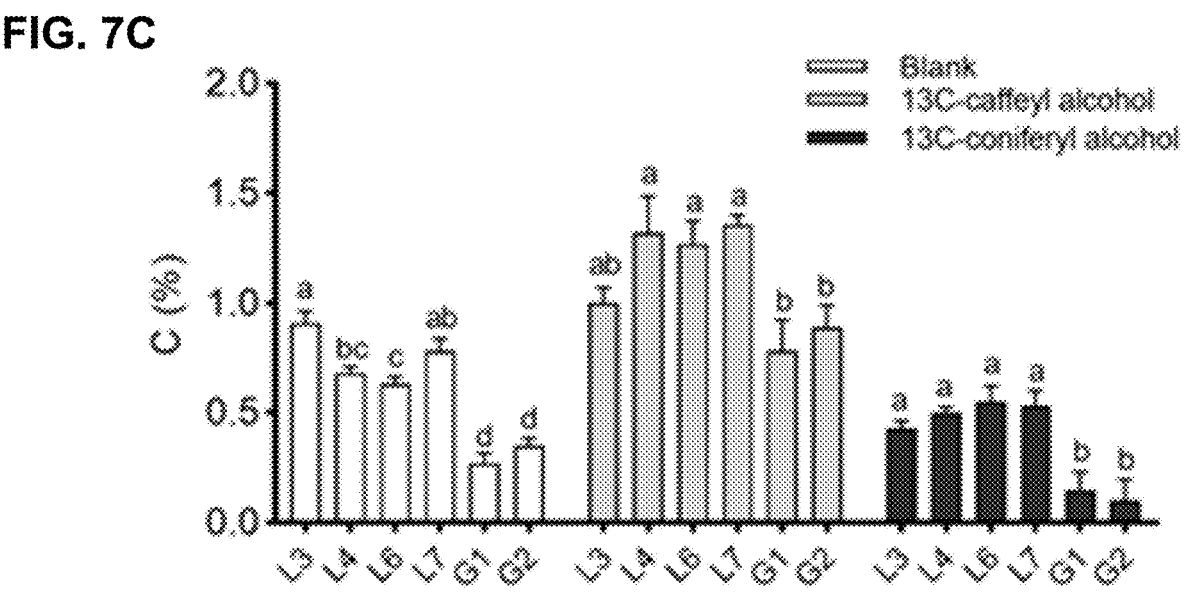

We selected four independent *Medicago* hairy root lines with differing ChLAC8 transcript levels (FIG. 7A) and also analyzed two controls expressing GUS in place of ChLAC8. In the GUS controls, the relative levels of lignin monomers were approximately 80% G-units and 20% H-units, with approximately 0.3% C-units and very low levels of S-units (due to the loss of function of COMT) (FIGS. 7B-7E). In all four lines overexpressing ChLAC8, there was a striking increase in the percentage of H units and a corresponding decrease in the percentage of G units. Furthermore, lignin from all lines expressing ChLAC8 now possessed significant levels of S-units as high as over 4% in line L6, with the highest ChLAC8 transcript levels (FIG. 7E). The increase in S-units and decrease in G units are consistent with the substrate preference of ChLAC8 for sinapyl rather than coniferyl alcohol, although an increase in S units in the comt mutant background was surprising. C-unit levels were also significantly increased in all four lines expressing ChLAC8 (FIG. 7C).

We labeled hairy root cultures with 100 μM $^{13}$C-monolignols for 2 days, harvested and processed the cultures to give alcohol insoluble cell wall residues (AIRs), and analyzed the AIRs for lignin composition and label incorporation by thioacidolysis (Lapierre et al., 1985; Chen et al., 2006). Percentage incorporation of a $^{13}$C-labeled monolignol into lignin was calculated based on the relative ratios of the M and M+6 ions at the retention time of the corresponding thioacidolysis product (FIGS. 6A-6I).

Figure 7H:
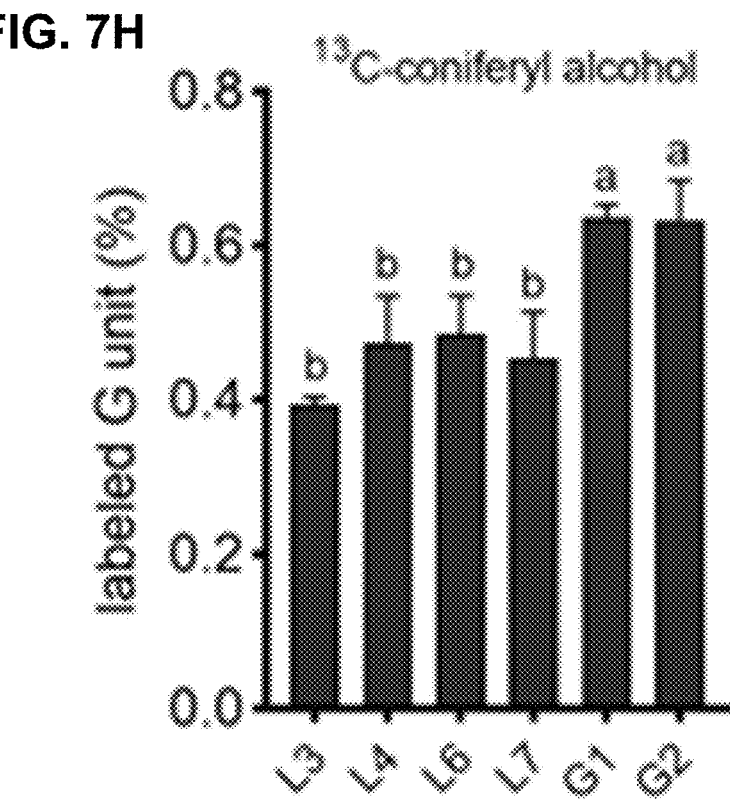
Figure 7I:
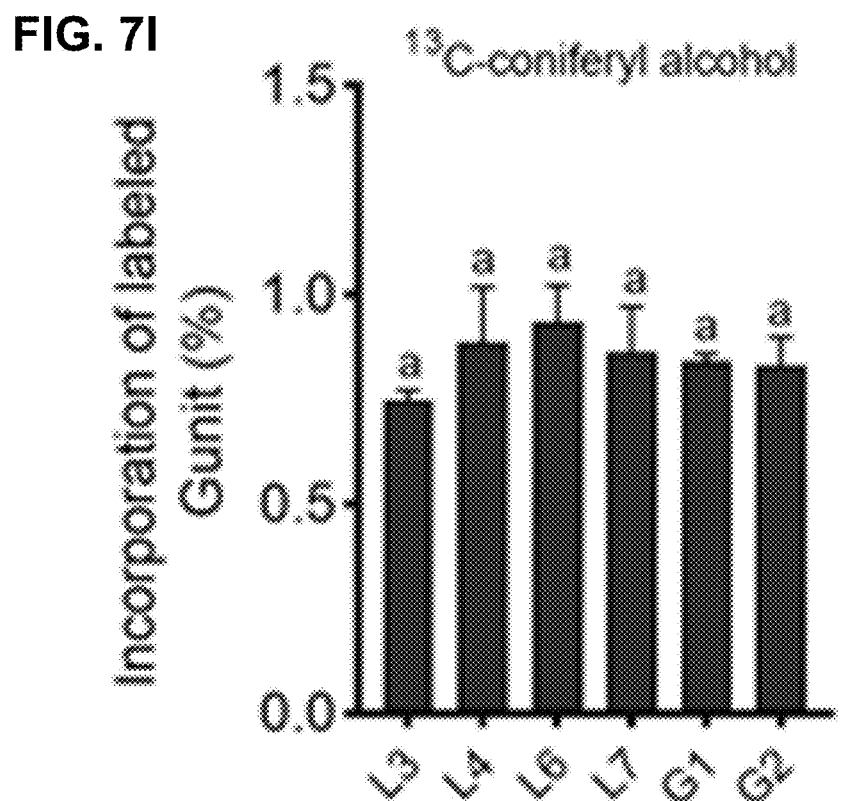

Feeding of $^{13}$C-caffeyl or coniferyl alcohols to *Medicago* hairy roots had virtually no effect on the overall % composition of H, G, or S units (FIGS. 7B, 7D, 7E). However, although the total incorporation of labeled monolignols was low as a percentage of total thioacidolyis yield (FIGS. 7F, 7H), feeding of $^{13}$C-caffeyl alcohol increased the % of C units in both the ChLAC8-expressing and GUS control lines (FIG. 7C). This suggests that *M. truncatula* possesses an endogenous enzyme that can facilitate incorporation of caffeyl alcohol into C-lignin. The percentage of C units that were labeled was lower in the ChLAC8-expressing lines than in the GUS controls, presumably because these lines contained nearly twice as much C-lignin prior to application of the label (FIGS. 7C, 7G). Consistent with the in vitro substrate preference of ChLAC8, feeding $^{13}$C-coniferyl alcohol did not increase in the proportion of G units or the percentage of labeled G units in ChLAC8-expressing roots (FIGS. 7D, 7H, 7I).

Figure 8A:
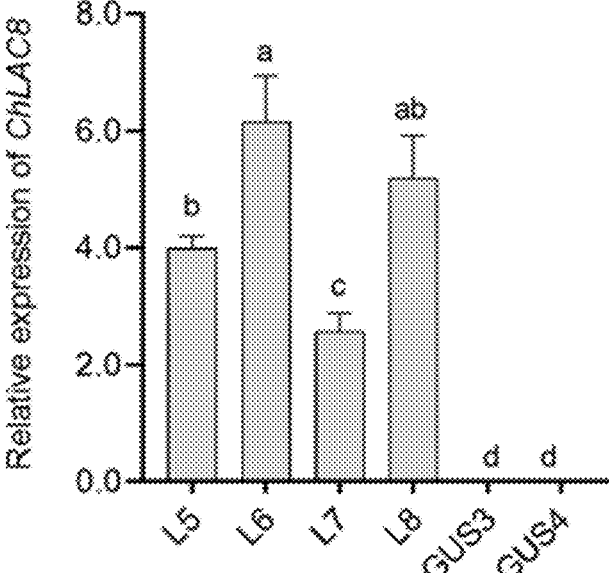
Figure 8B:
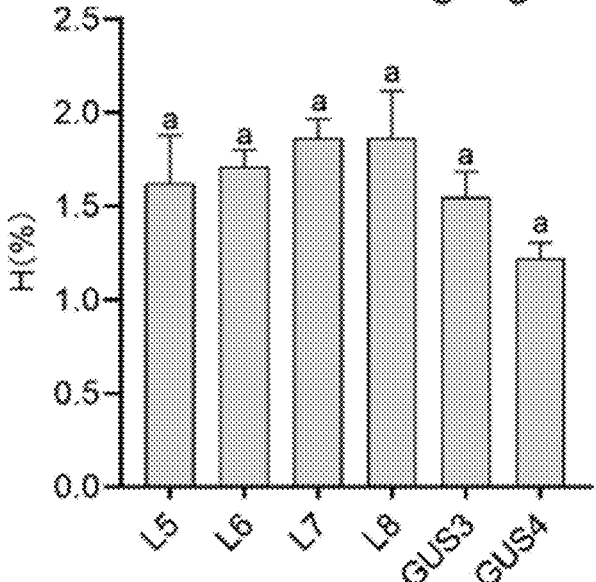
Figure 8C:
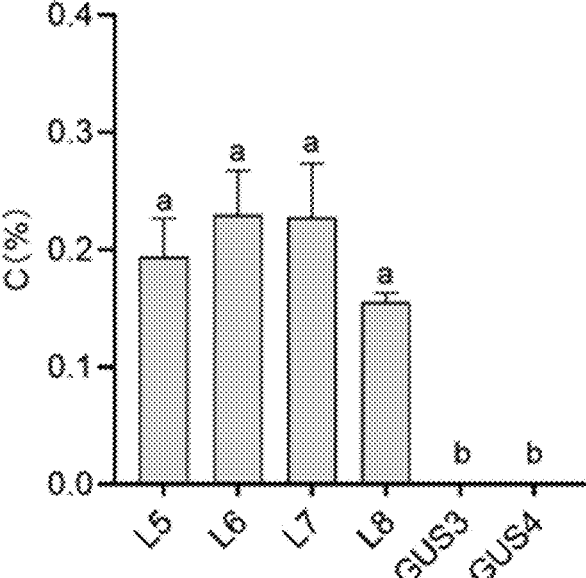

We then expressed ChLAC8 in the *Arabidopsis* comt mutant (Nakatsubo et al., 2008), with corresponding GUS-expressing plants used as controls (FIG. 8A). We analyzed lignin composition in inflorescence stems of homozygous $T_3$ transgenic lines by thioacidolysis. In contrast to the *Medicago* hairy roots, the lignin of the control lines contained over 95% G-units, with less than 2% H-units and smaller amounts of S-units, but no C-units were present (FIGS. 8B-D, 8F). All lines expressing ChLAC8 now possessed detectable but low levels of C-units (~0.2%), with a small but significant increase in S-units (FIGS. 8C, 8F). 5-Hydroxy-G-units, characteristic of the comt mutant (Ralph et al., 2001, Goujon et al., 2003), were also present at low levels and increased in these lines (FIG. 8E). These results suggest that ChLAC8 can also initiate polymerization of 5-hydroxyconiferyl alcohol, which will accumulate in the comt mutant background.

Figures 9A, 9B, 9C, 9D:
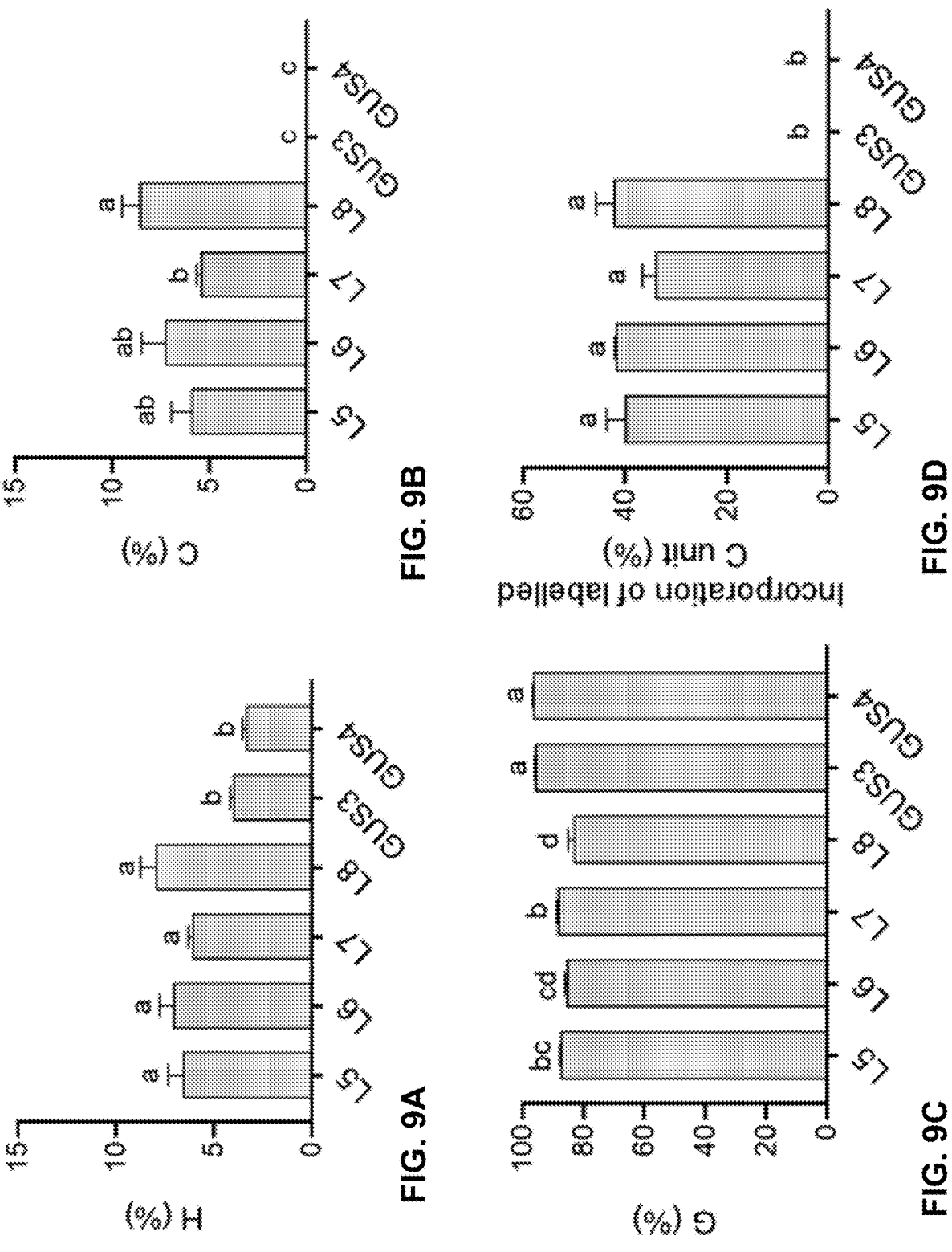
FIGS. 9A-9D illustrate incorporation of exogenous caffeyl alcohol into lignin in *A. thaliana* expressing ChLAC8.

Finally, we fed $^{13}C_6$-caffeyl alcohol to the top portions of cut inflorescence stems of the *Arabidopsis* comt mutants expressing ChLAC8 and the corresponding GUS-expressing controls (FIGS. 9A-9D). After just 2 days of feeding with 100 µM $^{13}C_6$-caffeyl alcohol, the incorporation of labeled C-units reached 34-42% in the ChLAC8-expressing lines, and C-units now accounted for approximately 5-9% of the total lignin thioacidolysis yield (FIGS. 9B, 9D). No labeled G-units were detected after feeding, and the levels of 5H- and S-units were under the limit of quantification in the top portion of the inflorescence stem. In contrast to the whole inflorescence stem, the top portions of the stems of all lines expressing ChLAC8 showed a significant decrease in G-units and a slight increase in H-units (FIGS. 9A, 9C). Importantly, no C-units were detected in the GUS control lines after feeding with caffeyl alcohol (FIG. 9B), indicating that, in the presence of an exogenous supply of caffeyl alcohol precursor, the expression of ChLAC8 was essential for C-lignin biosynthesis in the *Arabidopsis* inflorescence stem

DISCUSSION

ChLAC8 Expression Parallels C-Lignin Accumulation in the *Cleome* Seed Coat

Laccases are a large group of multicopper oxidases that are widely distributed in bacterial, fungi, animals, and plants. Recent advances in high-throughput sequencing technology and molecular biology have allowed several laccases that participate in lignin polymerization to be characterized in multiple plant species (Cheng et al., 2019; He et al., 2019; Le Bris et al., 2019; Wang et al., 2019; Simões et al., 2020). Nevertheless, little is known about whether laccases contribute in any way to lignin monomer composition. In the current study, 24 putative LACCASE genes were identified in *Cleome* by analysis of our previous transcriptome database and available genome information (Cheng et al., 2013; Zhuo et al., 2019).

Based on phylogenetic analysis, ChLAC members are divided into six subgroups (group I to VI), as are *Arabidopsis* laccases. Three *Arabidopsis* laccases (AtLAC4, AtLAC11, and AtLAC17) within group I and II appear necessary for monolignol (H, G and S) polymerization (Berthet et al., 2011; Zhao et al., 2013), implying similar roles for *Cleome* ChLAC4.1 (most closely related to AtLAC4), ChLAC11.1 (most closely related to AtLAC11), and ChLAC17.1 (most closely related to ChLAC17). ChLAC11.1 is expressed mainly in the stem (mostly in the fiber), whereas ChLAC4.1 and ChLAC17.1 are expressed in both the stem and in seed coat during the first 8 to 10 DAP. Whereas G-lignin is deposited in both the stem and seed coat in *Cleome*, S-lignin accumulates in the stem but is absent in the seed coat (Tobimatsu et al., 2013) due to a lack of expression of F5H (Zhuo et al., 2019). Based on the correlation between the transcript profiles of these three ChLACs and the G-/S-lignin deposition patterns in developing *Cleome* seeds and stem tissues, it is likely that ChLAC11.1 is related to G- or S-lignin biosynthesis in the stem, whereas ChLAC4.1 and ChLAC17.1 might be associated with G-lignin polymerization in the stem and the early stages of seed development (before 12 DAP). ChLAC15 is a homolog of *Arabidopsis* TT10, a laccase previously implicated in the oxidation of condensed tannins in the seed coat (Pourcel et al., 2005). Its expression early in seed development is consistent with the early appearance of condensed tannins in the seed coat of *Cleome*. However, the tt10 mutant of *Arabidopsis* has reduced lignin levels in the seed coat (Liang et al., 2006), so it is possible that ChLAC15 could also contribute to G-lignin biosynthesis in the *Cleome* seed coat. We also cannot rule out the involvement of ChLAC15, and the other ChLACs that are expressed in the seed coat but also elsewhere, in C-lignin biosynthesis during seed coat development.

Among all ChLAC members, ChLAC8X1, ChLAC8X2, and ChLAC8X3 (three ChLAC8 variants) are expressed in the seed coat after 12 DAP but not in the stem, exhibiting good correlations with C-lignin accumulation during development. ChLAC8X1, the full-length transcript with the highest expression, is the most likely candidate for a specific role in C-lignin biosynthesis. In the phylogenetic tree, ChLAC8 exhibits a close relationship with *Arabidopsis* AtLAC8. AtLAC8 is uniquely expressed in pollen grains as well as phloem, and knock-out of AtLAC8 resulted in early flowering and a reduced leaf number (Cai et al., 2006; Turlapati et al., 2011). However, in the current study, ChLAC8 knockdown lines showed no growth phenotype when plants were grown under greenhouse conditions. These results suggest that AtLAC8 and ChLAC8 might have divergent functions in planta, despite their 77% protein sequence identity.

ChLAC8 Shows a Strong Preference for Caffeyl and Sinapyl Alcohols

ChLAC8 was readily expressed in *E. coli*. Because laccases are glycoproteins, they are usually expressed in organisms that can catalyze N-glycosylation. However, there are several reports of the successful expression of laccases (mainly fungal and bacterial) in *E. coli* (e.g. Salony et al., 2008; Ihssen et al., 2015). The glycosyl portions appear to be associated with the stability rather than catalytic efficiency of the proteins (Maestre-Reyna et al., 2015). In the crystal structure of maize (*Zea mays*) ZmLAC expressed in the yeast *Pichia pastoris*, most of the N-glycosylation sites are substituted with single N-acetyl-D-glucosamine units after de-glycosylation (Xie et al., 2020). None of these sites in ZnLAC3 or ChLAC8 is in the key catalytic region of the protein.

To the best of our knowledge, whether caffeyl alcohol could function as a substrate for laccases from plants or fungi has not previously been tested. However, the substrate preference of ChLAC8, particularly the apparent lack of activity with coniferyl alcohol, is indeed unusual. Laccases from sycamore maple (*Acer pseudoplatanus*), *Miscanthus*, and maize (ZmLAC3) exhibit a preference, but not an absolute selectivity, for sinapyl alcohol over coniferyl alcohol (Sterjiades et al., 1992; He et al., 2019; Xie et al., 2020). This is consistent with a proposed mechanism that favors the presence of methoxyl groups in the substrate to be oxidized (Ramalingam et al., 2017) and the importance of interactions between the 5-methoxyl group of sinapyl alcohol and ZmLAC3 (Xie et al., 2020). The single methoxyl group of coniferyl alcohol may not allow for stable substrate binding. Our molecular modeling studies showed that, in addition to these interactions, Gln289 in ChLAC8 may help to stabilize caffeyl alcohol in the active site through strong hydrogen bonding; this residue is lacking from AtLAC8, as well as from AtLAC4 and AtLAC17, the two *Arabidopsis* laccases with confirmed roles in lignification (Berthet et al., 2011), and their *Cleome* homologs. The in vitro substrate preference of ChLAC8 was reflected in the results of expression of ChLAC8 in *Medicago* and *Arabidopsis* comt mutants, where increases in the levels of C- and S-units were observed without any increase in the levels of G-units. However, the activity with sinapyl alcohol is of no biological significance in the *Cleome* seed coat, which does not accumulate S-units (Zhuo et al., 2019). Nonetheless, the lack of activity of ChLAC8 with coniferyl alcohol could play a role in preventing polymerization of residual G monomer during the period of C-lignin biosynthesis.

Laccase Specificity as a Determinant of Lignin Composition

Both laccases and peroxidases have been ascribed roles in the polymerization of monolignols into lignin polymers. Their relative importance, as suggested by genetic loss-of-function experiments, appears to be largely dependent on tissue type; laccases are thought to play no role in lignification in the Casparian strip, a barrier to solutes but not a tissue responsible for providing mechanical strength (Lee et al., 2013). It has, however, recently been suggested that Laccase3 provides positional information for Casparian strip formation in *Arabidopsis* (Zhuang et al., 2020). The loss of function of three laccases in *Arabidopsis* resulted in the loss of lignin from vascular and supporting tissues, but not the Casparian strip (Zhao et al., 2013). As compelling genetic evidence now places at least a subset of peroxidases as functional in monolignol polymerization in planta, and the *Arabidopsis* lac4 lac11 lac17 triple maintains a full complement of expressed peroxidase genes, it is clear that laccases are essential for lignification in tissues other than the Casparian strip and may be particularly important during the initiation stages (Zhao et al., 2013).

It has generally been assumed that lignin monomer composition is determined by the synthesis of monolignols in the cytosol and/or transport of monolignols from the cytosol to apoplast. However, in view of the few reports of monolignol transporters (Miao and Liu, 2010; Alejandro et al., 2012) coupled with computational evidence that monolignol transport can occur via passive diffusion (Vermass et al., 2019), lignin composition could theoretically by determined at the level of monolignol polymerization. The present results suggest that, indeed, ChLAC8 can determine the composition of lignin, not only in the plant system of origin, but also when introduced into a heterologous host plant. It has recently been shown that heterologous expression of a laccase from *Miscanthus* can alter lignin composition in transgenic *Arabidopsis* (He et al., 2019), although in this case, the alteration did not reflect the monolignol preference of the laccase in vitro.

Although C-lignin is believed to be primarily a component of seed coats, the presence of low levels of C-lignin in *Medicago* hairy roots, which can be increased on feeding caffeyl alcohol, suggests that *Medicago* may possess a laccase with similar activity to ChLAC8. Such an enzyme appears to be absent from *Arabidopsis* inflorescence stems. MtLAC7 is the most closely related *Medicago* laccase to ChLAC8, but lacks the Gln residue equivalent to Gln289 in ChLAC8.

ChLAC8 as a Component of a Toolkit for Engineering C-Lignin

The physical and chemical properties of C-lignin make it an excellent material source for carbon fibers and high-value chemicals (Nar et al., 2016; Li et al., 2018; Stone et al., 2018; Wang et al., 2020). Despite its favorable properties, C-lignin has, to date, only been found in the seed coats of a limited number of non-crop plants, but has not yet been observed in vegetative tissues of any plant so far, which is a major hurdle for large-scale exploitation. Thus, genetic modification of suitable biomass crops to produce high amounts of C-lignin in tissues such as vessels and fibers is a yet to be achieved aspiration (Ralph et al., 2019). Engineering C-lignin will require systems for both the production and polymerization of caffeyl alcohol. Suppression of CCOAOMT, a key enzyme required for G-lignin biosynthesis, led to the incorporation of low levels (less than 10%) of caffeyl alcohol into the G-lignin polymer of the gymnosperm *Pinus radiata* (Wagner et al., 2011). However, downregulation of CCOAOMT and/or COMT failed to generate C-lignin in vascular tissues of the angiosperm species *Arabidopsis*, alfalfa (*Medicago sativa*), and poplar (Meyermans et al., 2000; Marita et al., 2003; Do et al., 2007). It is possible that the accumulation of caffeyl alcohol in vascular tissues has detrimental effects on the growth of angiosperms due to its high reactivity but is tolerated better in the seed coat and/or the vascular tissues of gymnosperms. It is also possible that the diversion of flux in the phenylpropanoid pathway away from coniferyl alcohol towards caffeyl alcohol is problematic because of additional functions for the former monolignol (Do et al. 2007; Zhou et al. 2010, Zhuo et al. 2019). In the current study, introducing ChLAC8 into the comt mutants of *Medicago* or *Arabidopsis* affected the lignin composition and led to significantly enhanced, although still low, levels of C-lignin. However, when caffeyl alcohol precursor was fed to *Arabidopsis* inflorescence stems, the levels of C-lignin dramatically increased, but only when ChLAC8 was expressed. These results suggest that, given a successful strategy for engineering sufficient levels of caffeyl alcohol, ChLAC8 can be an important component of a gene toolkit for engineering of C-lignin into vegetative tissues of commercial biomass crops such as switchgrass (*Panicum virgatum*) and poplar.

The *Cleome* seed coat also expresses over 20 peroxidase genes based on our transcriptomic analyses. The finding that downregulating ChLAC8 in the *Cleome* seed coat resulted in a significant reduction in C-lignin levels at 20 DAP but not at 24 DAP is consistent with a model in which the relative involvement of ChLAC8 compared to other seed-coat expressed peroxidases and laccases decreases during seed coat development. Correctly linked C-lignin is formed in vitro as a dehydrogenation polymer from caffeyl alcohol using horseradish peroxidase (Tobimatsu et al., 2013). Based on the results of the present feeding studies with $^{13}C_6$-caffeyl alcohol in *Arabidopsis*, it appears, perhaps paradoxically, that endogenous peroxidases are not sufficient for the polymerization of caffeyl alcohol in planta in the absence of a specific laccase.

Accession Numbers

Sequence data from this example can be found in the GenBank/EMBL libraries under the following accession numbers: ChLAC1, LOC104813919; ChLAC10, LOC104816217; ChLAC11.1, LOC104826904; ChLAC11.2, LOC104816339; ChLAC12, LOC104816528; ChLAC13, LOC104810694; ChLAC14X1, LOC104819341; ChLAC14X2, LOC104819341; ChLAC14X3, LOC104819341; ChLAC15, LOC104800224; ChLAC16X1, LOC104810729; ChLAC16X2, LOC104810729; ChLAC16X3, LOC104810729; ChLAC16X4, LOC104810729; ChLAC17.1, LOC104810824; ChLAC17.2, LOC104814854; ChLAC17.3, LOC104814851; ChLAC2.1; LOC104800682; ChLAC2.2, LOC104826315; ChLAC22, LOC104816561; ChLAC3.1, LOC104800769; ChLAC3.2, LOC104815814; ChLAC4.1, LOC104823387; ChLAC4.2, LOC104806523; ChLAC5, LOC104810126; ChLAC6, LOC104817377; ChLAC7.1X1, LOC104823274; ChLAC7.1X2, LOC104823274; ChLAC7.2, LOC104827034; ChLAC8X1, LOC104823484;

ChLAC8X2, LOC104823484; ChLAC8X3, LOC104823484; ChCAD5, LOC104804389; ChCCoA-OMT1, LOC104819570; ChCCoAOMT5, LOC104804378; ChCOMT1, LOC104811887, ChCOMT2, LOC104799941; ChANR, LOC104809521; AtLAC1, AT1G18140; AtLAC2, AT2G29130; AtLAC3, AT2G30210; AtLAC4; AT2G38080; AtLAC5, AT2G40370; AtLAC6, AT2G46570; AtLAC7, AT3G09220; AtLAC8, AT5G01040; AtLAC9, AT5G01050; AtLAC10, AT5G01190; AtLAC11, AT5G03260; AtLAC12, AT5G05390; AtLAC13, AT5G07130; AtLAC14, AT5G09360; AtLAC15, AT5G48100; AtLAC16, AT5G58910; AtLAC17, AT5G60020; MtLAC2, Medtr4g064530; MtLAC3, Medtr5g073210; MtLAC4.1, Medtr3g462760; MtLAC4.2; Medtr4g015120; MtLAC4.3, Medtr5g069680; MtLAC4.4, Medtr5g081810; MtLAC5, Medtr5g083360; MtLAC6, Medtr8g027375; MtLAC7.1, Medtr4g019225; MtLAC7.2, Medtr7g065970; MtLAC7.3, Medtr7g065980; MtLAC11.1, Medtr5g020600; MtLAC11.2, Medtr5g020620; MtLAC12, Medtr3g071890; MtLAC14, Medtr2g008330; MtLAC15.1, Medtr3g101635; MtLAC15.2, Medtr3g101640; MtLAC17.1, Medtr7g058690; MtLAC17.2, Medtr7g060460; MtLAC17.3, Medtr7g062250; MtLAC17.4, Medtr7g062310; MtLAC17.5, Medtr7g458880; ZmLAC1, Y897208; ZmLAC2, AM086214; ZmLAC3, AM086215; ZmLAC4, AM086216; ZmLAC5, AM086217; ApLAC, AAB09228.1; TrLAC3, Q9ZQW3; TrLAC90, Q9ZP47; TrLAC110, Q9ZQW2; BdLAC5, Bradi1g66720; BdLAC6, Bradi1g74320; GaLAC1, KX822020.1; SofLAC, SCUTST3084C11; BnTT10-1, HM805058.

REFERENCES

Alejandro, S., Lee, Y., Tohge, T., Sudre, D., Osorio, S., Park, J., Bovet, L., Lee, Y., Geldner, N., Fernie, A. R. and Martinoia, E. (2012) AtABCG29 is a monolignol transporter involved in lignin biosynthesis. Curr. Biol. 22: 1207-1212.

Almagro Armenteros, J. J., Tsirigos, K. D., Sønderby, C. K., Petersen, T. N., Winther, O., Brunak, S., von Heijne, G. and Nielsen, H. (2019) SignalP 5.0 improves signal peptide predictions using deep neural networks. Nat. Biotechnol. 37: 420-423.

Annunziata, M. G. (2019). What is lignin made of? New components discovered! Plant Physiol. 180:1255-1255.

Bao, W., O'Malley, D. M., Whetten, R. and Sederoff, R. R. (1993). A laccase associated with lignification in loblolly pine xylem. Science 260:672-674.

Barros, J., Serk, H., Granlund, I. and Pesquet, E. (2015). The cell biology of lignification in higher plants. Ann. Bot. 115:1053-1074.

Barros, J., Serrani-Yarce, J. C., Chen, F., Baxter, D., Venables, B. J. and Dixon, R. A. (2016). Role of bifunctional ammonia-lyase in grass cell wall biosynthesis. Nature Plants 2: 6, DOI: 10.1038/nplants.2016.50.

Berthet, S., Demont-Caulet, N., Pollet, B., Bidzinski, P., Cezard, L., Le Bris, P., Borrega, N., Herve, J., Blondet, E., Balzergue, S., et al. (2011). Disruption of LACCASE4 and 17 results in tissue-specific alterations to lignification of Arabidopsis thaliana stems. Plant Cell 23:1124-1137.

Blum, T., Briesemeister, S. and Kohlbacher, O. (2009) MultiLoc2: integrating phylogeny and gene ontology terms improves subcellular protein localization prediction. BMC Bioinformatics 10:274.

Bryan, A. C., Jawdy, S., Gunter, L., Gjersing, E., Sykes, R., Hinchee, M. A. W., Winkeler, K. A., Collins, C. M., Engle, N., Tschaplinski, T. J., et al. (2016). Knockdown of a laccase in Populus deltoides confers altered cell wall chemistry and increased sugar release. Plant Biotechnol J. 14:2010-2020.

Cai, X. N., Davis, E. J., Ballif, J., Liang, M. X., Bushman, E., Haroldsen, V., Torabinejad, J. and Wu, Y. J. (2006). Mutant identification and characterization of the laccase gene family in Arabidopsis. J. Exp. Bot. 57:2563-2569.

Caparrós-Ruiz, D., Fornalé, S., Civardi, L., Puigdomènech, P. and Rigau, J. (2006). Isolation and characterisation of a family of laccases in maize. Plant Sci. 171:217-225.

Chen, F., Reddy, M. S. S., Temple, S., Jackson, L. and Dixon, R. A. (2006). Multi-site genetic modulation of monolignol biosynthesis suggests new routes for formation of syringyl lignin and wall-bound ferulic acid in alfalfa (Medicago sativa L.). Plant J. 48:113-124.

Chen, F., Tobimatsu, Y., Havkin-Frenkel, D., Dixon, R. A. and Ralph, J. (2012). A polymer of caffeyl alcohol in plant seeds. Proc. Natl. Acad. Sci. USA 109:1772-1777.

Chen, F., Tobimatsu, Y., Jackson, L., Nakashima, J., Ralph, J. and Dixon, R. A. (2013). Novel seed coat lignins in the Cactaceae: structure, distribution and implications for the evolution of lignin diversity. Plant J. 73:201-211.

Cheng, S., van den Bergh, E., Zeng, P., Zhong, X., Xu, J., Liu, X., Hofberger, J., de Bruijn, S., Bhide, A. S., Kuelahoglu, C., et al. (2013). The Tarenaya hassleriana genome provides insight into reproductive trait and genome evolution of crucifers. Plant Cell 25:2813-2830.

Cheng, X., Li, G., Ma, C., Abdullah, M., Zhang, J., Zhao, H., Jin, Q., Cai, Y. and Lin, Y. (2019). Comprehensive genome-wide analysis of the pear (Pyrus bretschneideri) laccase gene (PbLAC) family and functional identification of PbLAC1 involved in lignin biosynthesis. Plos One 14:e0210892.

Clough, S. J. and Bent, A. F. (1998). Floral dip: a simplified method for Agrobacterium-mediated transformation of Arabidopsis thaliana. Plant J. 16:735-743.

Cocuron, J. C., Casas, M. I., Yang, F., Grotewold, E. and Alonso, A. P. (2019). Beyond the wall: High-throughput quantification of plant soluble and cell-wall bound phenolics by liquid chromatography tandem mass spectrometry. J. Chromatogr. A 1589:93-104.

del Rio J, C., Rencoret, J., Gutierrez, A., Kim, H. and Ralph, J. (2017). Hydroxystilbenes are monomers in palm fruit endocarp lignins. Plant Physiol. 174:2072-2082.

Dixon, R. A. and Barros, J. (2019). Lignin biosynthesis: old roads revisited and new roads explored. Open Biol. 9:190215.

Do, C.-T., Pollet, B., Thevenin, J., Sibout, R., Denoue, D., Barrière, Y., Lapierre, C. and Jouanin, L. (2007). Both caffeoyl Coenzyme A 3-O-methyltransferase 1 and caffeic acid O-methyltransferase 1 are involved in redundant functions for lignin, flavonoids and sinapoyl malate biosynthesis in Arabidopsis. Planta 226:1117-1129.

Duroux, L. and Welinder, K. G. (2003). The peroxidase gene family in plants: a phylogenetic overview. J. Mol. Evol. 57:397-407.

Emsley, P. and Cowtan, K. (2004). Coot: model-building tools for molecular graphics. Acta Crystallograph D 60:2126-2132.

Goujon, T., Sibout, R., Pollet, B., Maba, B., Nussaume, L., Bechtold, N., Lu, F., Ralph, J. Mila, I., Barrière, Y., et al. (2003). A new Arabidopsis thaliana mutant deficient in the expression of O-methyltransferase impacts lignins and sinapoyl esters. Plant Mol. Biol. 51:973-989.

Ha, C. M., Fine, D., Bhatia, A., Rao, X., Martin, M. Z., Engle, N. L., Wherritt, D. J., Tschaplinski, T. J., Sumner, L. W., Dixon, R. A., et al. (2019). Ectopic defense gene expression is associated with growth defects in *Medicago truncatula* lignin pathway mutants. Plant Physiol. 181: 63-84.

He, F., Machemer-Noonan, K., Golfier, P., Unda, F., Dechert, J., Zhang, W., Hoffmann, N., Samuels, L. Mansfield, S. D., Rausch, T., et al. (2019). The in vivo impact of MsLAC1, a *Miscanthus* laccase isoform, on lignification and lignin composition contrasts with its in vitro substrate preference. BMC Plant Biol. 19: 552.

Ihssen, J., Reiss, R., Luchsinger, R., Thöny-Meyer, L. and Richteret, M. (2015). Biochemical properties and yields of diverse bacterial laccase-like multicopper oxidases expressed in *Escherichia coli*. Sci. Rep. 5:10465|DOI: 10.1038/srep10465, 2015

Kumar, S., Stecher, G. and Tamura, K. (2016). MEGA7: Molecular Evolutionary Genetics Analysis Version 7.0 for Bigger Datasets. Mol. Biol. Evol. 33:1870-1874.

Lan, W., Lu, F., Regner, M., Zhu, Y., Rencoret, J., Ralph, S. A., Zakai, U. I., Morreel, K., Boerjan, W., Ralph, J. (2015). Tricin, a flavonoid monomer in monocot lignification. Plant Physiol. 167:1284-1295.

Lapierre C, Monties B. (1986) Thioacidolysis of poplar lignins: Identification of monomeric syringyl products and characterization of guaiacyl-syringyl lignin fractions. Holzforsch. 40:113-118.

Lapierre, C., Monties, B. and Rolando, C. (1985). Thioacidolysis of lignin: comparison with acidolysis. J. Wood Chem. Technol. 5:277-292

Le Bris, P., Wang, Y., Barbereau, C., Antelme, S., Cezard, L., Legee, F., D'Orlando, A., Dalmais, M. Bendahmane, A., Schuetz, M., et al. (2019). Inactivation of LACCASE8 and LACCASE5 genes in Brachypodium distachyon leads to severe decrease in lignin content and high increase in saccharification yield without impacting plant integrity. Biotech. Biofuels 12:181. Lee, Y., Rubio Maria, C., Alassimone, J. and Geldner, N. (2013). A mechanism for localized lignin deposition in the endodermis. Cell 153:402-412.

Li, Y., Shuai, L., Kim, H., Motagamwala, A. H., Mobley, J. K., Yue, F., Tobimatsu, Y., Havkin-Frenkel, D. Chen, F., Dixon, R. A., et al. (2018). An "ideal lignin" facilitates full biomass utilization. Sci. Adv. 4:eaau2968.

Liang, M., Davis, E., Gardner, D., Cai, X. and Wu, Y. (2006). Involvement of AtLAC15 in lignin synthesis in seeds and in root elongation of *Arabidopsis*. Planta 224:1185-1196.

Liu, C., Jun, J. and Dixon, R. A. (2014). MYB5 and MYB14 play pivotal roles in seed coat polymer biosynthesis in *Medicago truncatula*. Plant Physiol. 165:1424-1439.

Maestre-Reyna, M., Liu, W. C., Jeng, W. Y., Lee, C. C., Hsu, C. A., Wen, T. N., Wang, A. H. and Shyur, L. F. (2015). Structural and functional roles of glycosylation in fungal laccase from *Lentinus* sp. PloS one 10: e0120601. https://doi.org/10.1371/journal.pone.0120601

Marita, J. M., Ralph, J., Hatfield, R. D., Guo, D., Chen, F. and Dixon, R. A. (2003). Structural and compositional modifications in lignin of transgenic alfalfa down-regulated in caffeic acid 3-O-methyltransferase and caffeoyl coenzyme A 3-O-methyltransferase. Phytochemistry 62:53-65.

Meyermans, H., Morreel, K., Lapierre, C., Pollet, B., De Bruyn, A., Busson, R., Herdewijn, P., Devreese, B., Van Beeumen, J. and Marita, J. M. (2000). Modifications in lignin and accumulation of phenolic glucosides in poplar xylem upon down-regulation of caffeoyl-coenzyme A O-methyltransferase, an enzyme involved in lignin biosynthesis. J. Biol. Chem. 275:36899-36909.

Miao, Y.-C. and Liu, C.-J. (2010). ATP-binding cassette-like transporters are involved in the transport of lignin precursors across plasma and vacuolar membranes. Proc. Natl. Acad. Sci. USA, 107: 22728-22733.

Min-Kim, S., Sug-Kim, Y., Wan-Kim, D., and Yang, J. W. (2012). Transition metal-free, NaOtBu-O2-mediated one-pot cascade oxidation of allylic alcohols to α, β-unsaturated carboxylic acids. Green Chem. 14: 2996-2998

Morreel, K., Kim, H., Lu, F., Dima, O., Akiyama, T., Vanholme, R., Niculaes, C., Goeminne, G., Inze, D., Messens, E., Ralph, J. and Boerjan, W. (2010). Mass spectrometry-based fragmentation as an identification tool in lignomics. Anal. Chem. 82:8095-8105.

Morris, G. M., Huey, R., Lindstrom, W., Sanner, M. F., Belew, R. K., Goodsell, D. S. and Olson, A. J. (2009). Autodock4 and AutoDockTools4: automated docking with selective receptor flexiblity. J. Comput. Chem. 16:2785-2791.

Nakatsubo, T., Kitamura, Y., Sakakibara, N., Mizutani, M. Hattori, T., Sakurai, N., Shibata, D., Suzuki, S. and Umezawa, T. (2008). At5g54160 gene encodes *Arabidopsis thaliana* 5-hydroxyconiferaldehyde O-methyltransferase. J. Wood Sci. 54:312-317.

Nar, M., Rizvi, H. R., Dixon, R. A., Chen, F., Kovalcik, A. and D'Souza, N. (2016). Superior plant based carbon fibers from electrospun poly-(caffeyl alcohol) lignin. Carbon 103:372-383.

Nair, R. B., Bastress, K. L., Ruegger, M. O., Denault, J. W., and Chapple, C. (2004). The *Arabidopsis thaliana* REDUCED EPIDERMAL FLUORESCENCE1 gene encodes an aldehyde dehydrogenase involved in ferulic acid and sinapic acid biosynthesis. Plant Cell 16: 544-554.

Perna, V., Agger, J. W., Holck, J. and Meyer, A. S. (2018). Multiple reaction monitoring for quantitative laccase kinetics by LC-MS. Sci. Rep. 8:8114.

Parvathi, K., Chen, F., Guo, D., Blount, J. W. and Dixon, R. A. (2001). Substrate preferences of O-methyltransferases in alfalfa suggest new pathways for 3-O-methylation of monolignols. Plant J. 25:193-202.

Pitti, T., Chen, C.-T., Lin, H.-N., Choong, W.-K., Hsu, W.-L. and Sung, T.-Y. (2019). N-GlyDE: a two-stage N-linked glycosylation site prediction incorporating gapped dipeptides and pattern-based encoding. Sci. Rep. 9: 15975.

Pourcel, L., Routaboul, J. M., Kerhoas, L., Caboche, M., Lepiniec, L. and Debeaujon, I. (2005). TRANSPARENT TESTA10 encodes a laccase-like enzyme involved in oxidative polymerization of flavonoids in *Arabidopsis* seed coat. Plant Cell 17:2966-2980.

Ragauskas, A. J., Beckham, G. T., Biddy, M. J., Chandra, R., Chen, F., Davis, M. F., Davison, B. H., Dixon, R. A., Gilna, P., Keller, M., et al. (2014). Lignin valorization: improving lignin processing in the biorefinery. Science 344:1246843.

Ralph, J., Lapierre, C.and Boerjan, W. (2019). Lignin structure and its engineering. Curr. Opin. Biotechnol. 56:240-249.

Ralph, J., Lapierre, C., Marita, J. M., Kim, H., Lu, F., Hatfield, R. D., Ralph, S., Chapple, C. Franke, R., Hemm, M. R., et al. (2001). Elucidation of new structures in lignins of CAD- and COMT-deficient plants by NMR. Phytochemistry 57:993-1003.

Ramalingam, B., Sana, B., Seayad, J., Ghadess, F. J. and Sullivan, M. B. (2017). Towards understanding of laccase-catalysed oxidative oligomerisation of dimeric lignin model compounds. RSC Adv. 7:11951-11958.

Ranasinghe, S., Rogers, M. E., Hamilton, J. G. C., Bates, P. A. and Maingon, R. D. C. (2008). A real time PCR assay to estimate *Leishmania chagasi* load in its natural sand fly vector *Lutzomyia longipalpis*. Trans. R. Soc. Trop. Med. Hyg. 102:875-882.

Rao, X., Krom, N., Tang, Y., Widiez, T., Havkin-Frenkel, D., Belanger, F. C., Dixon, R. A. and Chen, F. (2014). A deep transcriptomic analysis of pod development in the *vanilla* orchid (*Vanilla planifolia*). BMC Genomics 15:964.

Salony, Garg, N., Baranwal, R., Chhabra, M., Mishra, S., Chaudhuri, T. K. and Bisaria, V. S. (2008). Laccase of *Cyathus bulleri*: structural, catalytic characterization and expression in *Escherichia coli*. Biochim Biophys Acta—Proteins and Proteomics 1784: 259-268.

Schwede, T., Kopp, J., Guex, N. and Peitsch, M. C. (2003). SWISS-MODEL: an automated protein homology-modeling server. Nucleic Acids Res. 31:3381-3385.

Shigeto, J. and Tsutsumi, Y. (2016). Diverse functions and reactions of class III peroxidases. New Phytol. 209:1395-1402.

Simões, M. S., Carvalho, G. G., Ferreira, S. S., Hernandes-Lopes, J., de Setta, N. and Cesarino, I. (2020). Genome-wide characterization of the laccase gene family in *Setaria viridis* reveals members potentially involved in lignification. Planta 251:46.

Sterjiades, R., Dean, J. F. and Eriksson, K. E. (1992). Laccase from sycamore maple (*Acer pseudoplatanus*) polymerizes monolignols. Plant Physiol. 99:1162-1168.

Stone, M. L., Anderson, E. M., Meek, K. M., Reed, M., Katahira, R., Chen, F., Dixon, R. A., Beckham, G. T. and Román-Leshkov, Y. (2018). Reductive catalytic fractionation of C-Lignin. ACS Sust. Chem. Eng. 6:11211-11218.

Thompson, J. D., Gibson, T. J. and Higgins, D. G (2003). Multiple sequence alignment using ClustalW and ClustalX. Curr. Protocols Bioinformatics 00:2.3.1-2.3.22.

Teixeira, J., Silva, T., Benfeito, S., Gaspar, A., Garrido, E. M., Garrido J. and Borges, F. (2013). Exploring nature profits: Development of novel and potent lipophilic anti-oxidants based on galloyl-cinnamic hybrids. Eur. J. Med. Chem. 62: 289-296

Tobimatsu, Y., Chen, F., Nakashima, J., Escamilla-Trevino, L. L., Jackson, L., Dixon, R. A. and Ralph, J. (2013). Coexistence but independent biosynthesis of catechyl and guaiacyl/syringyl lignin polymers in seed coats. Plant Cell 25:2587-2600.

Tobimatsu, Y. and Schuetz, M. (2019). Lignin polymerization: how do plants manage the chemistry so well? Curr. Opin. Biotechnol. 56:75-81.

Turlapati, P. V., Kim, K. W., Davin, L. B. and Lewis, N. (2011). The laccase multigene family in *Arabidopsis thaliana*: towards addressing the mystery of their gene function(s). Planta 233:439-470.

Vanholme, R., De Meester, B., Ralph, J. and Boerjan, W. (2019). Lignin biosynthesis and its integration into metabolism. Curr. Opin. Biotechnol. 56:230-239.

Vermaas, J. V., Dixon, R. A., Chen, F., Mansfield, S. D., Boerjan, W., Ralph, J., Crowley, M. F. and Beckham, G. T. (2019). Passive membrane transport of lignin-related compounds. Proc. Natl. Acad. Sci. USA 116: 23117-23123.

Wagner, A., Tobimatsu, Y., Phillips, L., Flint, H., Torr, K., Donaldson, L., Pears, L. and Ralph, J. (2011). CCOA-OMT suppression modifies lignin composition in *Pinus radiata*. Plant J. 67:119-129.

Wang, J., Feng, J., Jia, W., Chang, S., Li, S.and Li, Y. (2015a). Lignin engineering through laccase modification: a promising field for energy plant improvement. Biotechnol. Biofuels 8:145.

Wang, S., Su, S., Xiao, L.-P., Wang, B., Sun, R.-C. and Song, G. (2020) Catechyl lignin extracted from castor seed coats using deep eutectic solvents: characterization and depolymerizatio. ACS Sust. Chem. Eng. 8:7031-7038.

Wang, Q., Li, G., Zheng, K., Zhu, X., Ma, J., Wang, D., Tang, K., Feng, X., Leng, J., Yu, H., et al. (2019). The soybean laccase gene family: evolution and possible roles in plant defense and stem strength selection. Genes 10:701.

Wang, X., Zhuo, X., Xiao, X., Wang, X., Docampo-Palacios, M., Chen, F., Dixon, R. (2020). Substrate Specificity of LACCASE8 Facilitates Polymerization of Caffeyl Alcohol for C-Lignin Biosynthesis in the Seed Coat of *Cleome hassleriana*. The Plant Cell 32:3825-3845.

Wang, Y., Bouchabke-Coussa, O., Le Bris, P., Antelme, S., Soulhat, C., Gineau, E., Dalmais, M., Bendahmane, A. Morin, H., Mouille, G., et al. (2015b). LACCASE 5 is required for lignification of the Brachypodium distachyon culm. Plant Physiol. 168:192-204.

Weng, J. K., Mo, H.and Chapple, C. (2010). Over-expression of F5H in COMT-deficient *Arabidopsis* leads to enrichment of an unusual lignin and disruption of pollen wall formation. Plant J. 64:898-911.

Xie, T., Liu, Z. and Wang, G. (2020). Structural basis for monolignol oxidation by a maize laccase. Nat. Plants 6:231-237.

Xie, D.-Y., Sharma, S. B., Paiva, N. L., Ferreira, D. and Dixon, R. A. (2003). Role of anthocyanidin reductase, encoded by BANYULS, in plant flavonoid biosynthesis. Science 299: 396-399.

Zhao, Q., Nakashima, J., Chen, F., Yin, Y. B., Fu, C. X., Yun, J. F., Shao, H., Wang, X. Q., Wang, Z. Y. and Dixon, R. A. (2013). LACCASE is necessary and nonredundant with PEROXIDASE for lignin polymerization during vascular development in *Arabidopsis*. Plant Cell 25:3976-3987.

Zhuang, Yan., Zuo, D., Tao, Y., Cai, H. and Li, L. (2020). Laccase3-based extracellular domain provides possible positional information for directing Casparian strip formation in *Arabidopsis*. Proc. Natl. Acad. Sci. USA. 117: 2020 05429. 10.1073/pnas.2005429117.

Zhou, R., Jackson, L., Shadle, G., Nakashima, J., Temple, S., Chen, F. and Dixon R. A. (2010). Distinct cinnamoyl CoA reductases involved in parallel routes to lignin in *Medicago truncatula*. Proc. Natl. Acad. Sci. USA 107:17803-17808.

Zhuo, C., Rao, X., Azad, R., Pandey, R., Xiao, X., Harkelroad, A., Wang, X., Chen, F. and Dixon, R. A. (2019). Enzymatic basis for C-lignin monomer biosynthesis in the seed coat of *Cleome hassleriana*. Plant J. 99:506-520.

30

The invention claimed is:

1. A recombinant polynucleotide comprising:
   a laccase (LAC) polynucleotide encoding a LAC polypeptide capable of polymerizing caffeyl alcohol, wherein the LAC polypeptide is a conservative variant of the LAC polypeptide of SEQ ID NO:3 having a sequence that is at least 95% identical to SEQ ID NO:3 with only conservative substitutions compared to SEQ ID NO:3, and having a glutamine residue in position 289 (Q289);
   and at least one heterologous polynucleotide sequence operatively linked to the LAC polynucleotide, wherein the at least one heterologous polynucleotide sequence comprises a regulatory polynucleotide sequence, promoter sequence, a selectable marker polynucleotide, or a combination thereof.

2. The recombinant polynucleotide of claim 1, wherein the LAC polypeptide encoded by the LAC polynucleotide further includes amino acid residues E464 and H534.

3. A vector comprising the recombinant polynucleotide of claim 1.

4. A cell comprising the recombinant polynucleotide of claim 1.

5. The cell of claim 4, wherein the cell is a plant cell, bacteria cell, yeast cell, or fungus cell.

6. The cell of claim 5, wherein the cell is a plant cell.

7. The cell of claim 6, wherein the plant cell is a plant cell selected from the group of plant cells consisting of: *Arabidopsis*, switchgrass, poplar, *eucalyptus, miscanthus*, corn, rice, wheat, barley, cotton, maize, soybean, canola and other biomass plants.

8. A transgenic plant comprising:
   a plurality of plant cells, wherein one or more of the plurality of plant cells comprises a recombinant polynucleotide of claim 1.

9. The transgenic plant of claim 8, wherein the transgenic plant expresses an increased amount of a LAC polypeptide capable of polymerizing caffeyl alcohol as compared to a corresponding non-transgenic control plant.

10. The transgenic plant of claim 8, wherein the transgenic plant is selected from the group of plants consisting of: *Arabidopsis*, switchgrass, poplar, *eucalyptus, miscanthus*, corn, rice, wheat, barley, cotton, maize, soybean, canola and other biomass plants.

11. The transgenic plant of claim 8, wherein the transgenic plant produces caffeyl alcohol.

12. The transgenic plant of claim 8, wherein the transgenic plant has increased production of C-lignin.

13. A method of increasing production of C-lignin in a plant, the method comprising:
   providing a plant having one or more cells comprising the recombinant polynucleotide of claim 1, wherein the recombinant polynucleotide is integrated into the genome of the one or more cells or housed on a vector in the one or more cells, such that the recombinant polynucleotide is expressed in the one or more plant cells; and
   growing said plant in the presence of caffeyl alcohol, wherein the recombinant polynucleotide is overexpressed in the plant relative to a wild-type plant, such that the plant produces C-lignin, wherein the caffeyl alcohol is externally provided, is synthesized by the plant, or both.

14. The method of claim 13, wherein the plant produces a greater amount of C-lignin than a corresponding wild-type plant.

15. The method of claim 13, wherein the plant is selected from the group of plants consisting of: *Arabidopsis*, switchgrass, poplar, *eucalyptus, miscanthus*, corn, rice, wheat, barley, cotton, maize, soybean, canola and other biomass plants.

* * * * *